United States Patent [19]
Elslager et al.

[11] Patent Number: 4,604,390
[45] Date of Patent: Aug. 5, 1986

[54] ANTIBACTERIAL BENZO(CHALCOGENO)[4,3,2-CD]INDAZOLES

[75] Inventors: Edward F. Elslager; Leslie M. Werbel, both of Ann Arbor; Daniel F. Ortwine, Saline; Donald F. Worth, Ann Arbor; Howard D. H. Showalter, Ann Arbor; David B. Capps, Ann Arbor; Ellen M. Berman, Ann Arbor; Vlad E. Gregor, Ann Arbor; Anthony D. Sercel, Ann Arbor, all of Mich.

[73] Assignee: Warner-Lambert Company, Morris Plains, N.J.

[21] Appl. No.: 738,195

[22] Filed: May 24, 1985

Related U.S. Application Data

[63] Continuation-in-part of Ser. No. 626,090, Jun. 29, 1984, abandoned, and a continuation-in-part of Ser. No. 626,170, Jun. 29, 1984, abandoned, and a continuation-in-part of Ser. No. 559,402, Dec. 12, 1983, abandoned, which is a continuation-in-part of Ser. No. 456,162, Jan. 6, 1983, abandoned.

[51] Int. Cl.[4] .................. A61K 31/415; A61K 31/54; C07D 491/06; C07D 517/06
[52] U.S. Cl. ..................... 514/222; 514/227; 514/231; 514/234; 514/237; 514/239; 514/255; 514/376; 544/58.7; 544/60; 544/137; 544/140; 544/369; 544/371; 548/229; 548/370
[58] Field of Search .............. 544/60, 137, 140, 369, 544/370, 58 T; 546/199; 548/229, 370; 514/222, 227, 255, 322, 376, 403, 406, 231, 234, 237, 239

[56] References Cited

U.S. PATENT DOCUMENTS 3,505,341 4/1970 Elslager et al. ............... 548/370
3,816,438 6/1974 Houlihan .................... 548/370
3,963,740 6/1976 Elslager ..................... 548/370

Primary Examiner—Richard A. Schwartz
Assistant Examiner—Kurt G. Briscoe
Attorney, Agent, or Firm—Jerry F. Janssen

[57] ABSTRACT

Substituted 2H-[1]benzopyrano[4,3,2-cd]indazoles, 2H-[1]benzothiopyrano[4,3,2-cd]indazoles, and 2H-[1]benzoselenino[4,3,2-cd]indazoles have demonstrated pharmacological activity against a broad spectrum of Gram-positive and Gram-negative bacteria, yeasts, and fungi, as well as activity against the L1210 and P388 murine leukemia cells lines.

Pharmaceutical compositions containing the compounds and methods of employing the compounds in methods of treating bacterial or fungal infections and of inhibiting the growth of neoplasms in mammals are also disclosed.

46 Claims, No Drawings

ANTIBACTERIAL BENZO(CHALCOGENO)[4,3,2-CD]INDAZOLES

CROSS-REFERENCE TO RELATED APPLICATIONS

This application is a combined continuation-in-part of application Ser. Nos. 626,090 filed June 29, 1984, now abandoned; 626,170 filed June 29, 1984, now abandoned; and Ser. No. 559,402 filed Dec. 12, 1983, now abandoned, which in turn is a continuation-in-part of application Ser. No. 456,162 filed Jan. 6, 1983, now abandoned.

TECHNICAL FIELD

The invention relates to novel substituted benzo-(chalcogeno)[4,3,2-cd]indazoles, to methods for their production, to pharmaceutical compositions comprising the compounds, and to methods of treatment using the compounds in dosage form. The compounds of the invention have pharmacological properties and are useful antibacterial agents, and antifungal agents.

BACKGROUND OF THE INVENTION

The benzopyrano[4,3,2-cd]indazole ring system is new and is illustrated by the formula

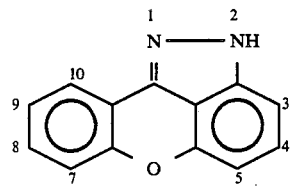

The benzothiopyrano[4,3,2-cd]indazole ring system

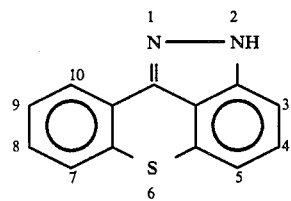

is known from F. Ullman and Otto van Glenck, Ber., 49: 2489 (1916) and from U.S. Pat. No. 3,505,341 to Elslager et al.

The benzoselenino[4,3,2-cd]indazole ring system is new and is illustrated by the formula

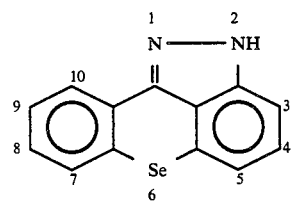

SUMMARY OF THE INVENTION

In its broadest chemical compound aspect, the present invention provides benzo(chalcogeno)[4,3,2-cd]indazole compounds having, in free base form, the structural formula 1

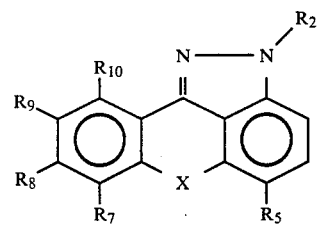

and to the pharmaceutically acceptable salts thereof, wherein X is oxygen, sulfur, or selenium; the substituents $R_7$, $R_8$, $R_9$, and $R_{10}$ are independently hydrogen, hydroxy, alkoxy of from 1 to 4 carbon atoms (hereinafter referred to as "lower alkoxy"); wherein $R_2$ is —ANR'R" wherein A is a straight or branched alkylene chain of from 2 to 5 carbon atoms optionally substituted with hydroxyl; wherein R' and R" are hydrogen or are straight or branched alkyl of from 1 to 4 carbon atoms (hereinafter referred to as "lower alkyl") optionally substituted with hydroxyl, or where R' and R" taken together also represent

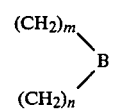

wherein m and n are each an integer of from 2 to 3 and B is a direct bond, or oxygen, sulfur, or NR''' wherein R''' is hydrogen or straight or branched alkyl of from 1 to 4 carbon atoms optionally substituted with hydroxyl; and wherein $R_5$ is nitro, $NH_2$, $NHR_2$, or NHR'''' where R'''' is

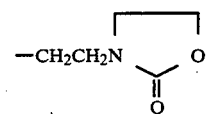

or is

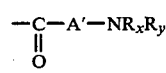

wherein A' is a straight or branched alkylene chain of from 1 to 5 carbon atoms, and $R_x$ and $R_y$ are independently hydrogen or straight or branched alkyl of from 1 to 4 carbon atoms optionally substituted with hydroxyl.

In one sub-generic chemical compound aspect, the present invention provides benzopyrano[4,3,2-cd]indazole compounds of the general formula 2

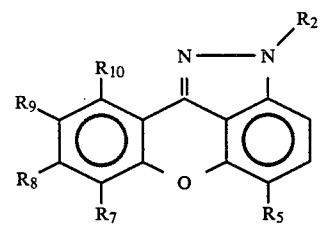

wherein $R_2$, $R_5$, $R_7$, $R_8$, $R_9$, and $R_{10}$ have the definitions given above.

In another sub-generic chemical compound aspect, the present invention provides benzothiopyrano[4,3,2-cd]indazole compounds of the general formula 3

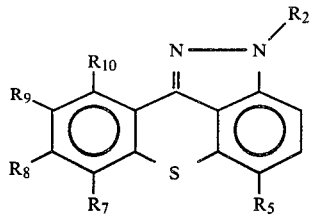

wherein $R_2$, $R_5$, $R_7$, $R_8$, $R_9$, and $R_{10}$ have the definitions given above.

In yet another sub-generic chemical compound aspect, the present invention provides benzoselenino[4,3,2-cd]-indazole compounds of the general formula 4

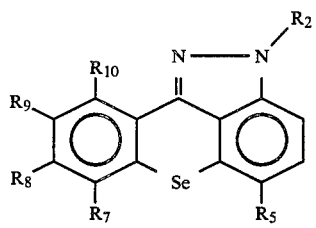

wherein $R_2$, $R_5$, $R_7$, $R_8$, $R_9$, and $R_{10}$ have the definitions given above.

In another aspect, the present invention provides pharmaceutical compositions useful for treating bacterial infections in a mammal comprising an antibacterially effective amount of a compound having structural formula 1 above wherein X is oxygen, sulfur, or selenium, and the substituents $R_2$, $R_5$, $R_7$, $R_8$, $R_9$, and $R_{10}$ are as previously defined, in combination with a pharmaceutically acceptable carrier.

In yet another aspect, the present invention comprises a method of treating bacterial infections in a mammal comprising administering to a mammal in need of such treatment an antibacterially effective amount of a compound having structural formula 1 above wherein X is oxygen, sulfur, or selenium, and the substituents $R_2$, $R_5$, $R_7$, $R_8$, $R_9$, and $R_{10}$ are as previously defined, in combination with a pharmaceutically acceptable carrier.

DETAILED DESCRIPTION

The present invention provides a class of benzo-(chalcogeno)[4,3,2-cd]indazole compounds which have demonstrated activity against a broad spectrum of Gram-negative and Gram-positive bacteria and several species of yeasts and filamentous fungi. In addition, the compounds of this invention demonstrate pharmacological activity as evidenced by their in vitro and in vivo activity against the L1210 and P388 murine leukemia cell lines.

The compounds of the invention form pharmaceutically acceptable salts with both organic and inorganic acids. Examples of suitable acids for the formation of salts in accordance with this invention include hydrochloric, sulfuric, phosphoric, acetic, citric, oxalic, malonic, salicylic, malic, fumaric, succinic, ascorbic, maleic, methanesulfonic, isethionic, lactic, gluconic, glucuronic, sulfamic, benzoic, tartaric, pamoic, and the like, The salts are prepared by contacting the free base form of the compounds with an equivalent amount of the desired acid in the conventional manner. The free base forms may be regenerated, if desired, by treating the salt with a base. For example, dilute aqueous solutions of bases such as sodium or other alkali metal hydroxide, potassium or other alkali metal carbonate or bicarbonate, ammonia, and the like are suitable for this purpose.

The salts of compounds of the present invention differ somewhat from the free base form in such physical properties as melting point and solubility in polar solvents, but they are otherwise equivalent to the free base forms for purposes of this invention.

The compounds of the invention can exist in unsolvated as well as solvated forms, including hydrated forms. In general, the solvated forms with pharmaceutically acceptable solvents such as water, ethanol, and the like are equivalent to the unsolvated forms for the purpose of this invention.

In one preferred sub-generic aspect, the present invention provides benzopyrano[4,3,2-cd]indazole compounds of structural formula 2

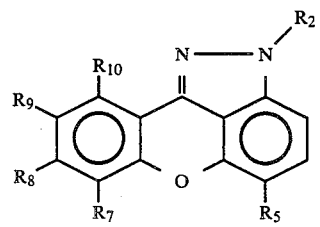

wherein the substituents $R_7$, $R_8$, $R_9$, and $R_{10}$ are independently hydrogen, hydroxy, alkoxy of from 1 to 4 carbon atoms (hereinafter referred to as "lower alkoxy"); wherein $R_2$ is —ANR'R" wherein A is a straight or branched alkylene chain of from 2 to 5 carbon atoms optionally substituted with hydroxyl; wherein R' and R" are hydrogen or are straight or branched alkyl of from 1 to 4 carbon atoms (hereinafter referred to as "lower alkyl") optionally substituted with hydroxyl, or where R' and R" taken together also represent

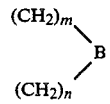

wherein m and n are each an integer of from 2 to 3 and B is a direct bond, or oxygen, sulfur, or NR''' wherein R''' is hydrogen or straight or branched alkyl of from 1 to 4 carbon atoms optionally substituted with hydroxyl; and wherein $R_5$ is nitro, $NH_2$, $NHR_2$, or NHR'''' where R'''' is

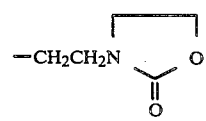

or is

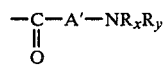

wherein A' is a straight or branched alkylene chain of from 1 to 5 carbon atoms, and $R_x$ and $R_y$ are independently hydrogen or straight or branched alkyl of from 1 to 4 carbon atoms optionally substituted with hydroxyl.

Preferred are compounds of structural formula 5

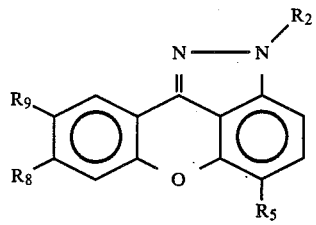

where $R_2$ and $R_5$ are as previously defined, and $R_8$ and $R_9$ are limited to hydrogen, hydroxy, and lower alkoxy, particularly where both $R_8$ and $R_9$ are hydrogen, or where either $R_8$ or $R_9$ is hydrogen and the other is hydroxy or lower alkoxy.

In another preferred aspect, compounds of the present invention include compounds of structural formula 5 where $R_8$ and $R_9$ are both hydrogen or one is hydrogen and the other is hydroxy or lower alkoxy, and $R_5$ is limited to $NHR_2$ where $R_2$ is as previously defined.

Most preferred, for their pharmacological properties, are compounds in accordance with the present invention having the names:

N-[2-[2-(Diethylamino)ethyl]-2H-[1]benzopyrano-[4,3,2-cd]indazol-5-yl]ethanediamine;

N-[2-[2-(Diethylamino)ethyl]-9-hydroxy-2H-[1]benzopyrano[4,3,2-cd]indazol-5-yl]ethanediamine;

N,N-Diethyl-9-methoxy-5-nitro-2H-[1]benzopyrano-[4,3,2-cd]indazole-2-ethanamine;

N,N-Diethyl-9-hydroxy-5-nitro-2H-[1]benzopyrano-[4,3,2-cd]indazole-2-ethanamine;

9-Methoxy-N,N-dimethyl-5-nitro-2H-[1]benzopyrano-[4,3,2-cd]indazole-2-propanamine;

2-[3-(Dimethylamino)propyl]-5-nitro-2H-[1]benzopyrano[4,3,2-cd]indazol-9-ol;

5-Amino-2-[2-(diethylamino)ethyl]-2H-[1]benzopyrano[4,3,2-cd]indazol-9-ol;

5-Amino-2-[2-[(2-hydroxyethyl)amino]ethyl]-2H-[1]benzopyrano[4,3,2-cd]indazol-9-ol;

N-[2-[2-(Diethylamino)ethyl]-9-hydroxy-2H-[1]benzopyrano[4,3,2-cd]indazol-5-yl]-2-[(2-hydroxyethyl)amino]acetamide;

2-[2-[(2-Hydroxyethyl)amino]ethyl]-5-nitro-2H-[1]benzopyrano[4,3,2-cd]indazol-9-ol;

2-[2-(Diethylamino)ethyl]-5-[[2-[(2-hydroxyethyl)-amino]ethyl]amino-2H-[1]benzopyrano[4,3,2-cd]indazol-9-ol;

2-[2-[(2-Hydroxyethyl)amino]ethyl]-9-hydroxy-2H-[1]benzopyrano[4,3,2-cd]indazol-5-yl]-2-(2-hydroxyethyl)-amino]acetamide;

2-[2-[(2-Hydroxyethyl)amino]ethyl]-5-[[2-[(2-hydroxyethyl)amino]ethyl]amino]-2H-[1]benzopyrano[4,3,2-cd]indazol-9-ol;

9-Methoxy-2-[2-(1-pyrrolidinyl)ethyl]-2H-[1]benzopyrano[4,3,2-cd]indazol-5-amine;

5-Nitro-2-[2-(1-pyrrolidinyl)ethyl]-2H-[1]benzopyrano[4,3,2-cd]indazol-9-ol; and 5-[(2-Aminoethyl)amino]-2-[2-(diethylamino)ethyl]-2H-[1]benzopyrano[4,3,2-cd]indazol-8-ol.

Certain of the compounds of the present invention are also useful as intermediates for the preparation of the preferred species; more specifically, those compounds of structure 2 above wherein $R_5$ represents $NO_2$ or $NH_2$.

The invention in another aspect also includes novel intermediate compounds of structural formula 6

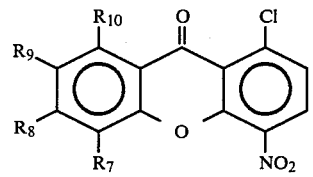

wherein the substituent groups $R_7$, $R_8$, $R_9$, and $R_{10}$ are independently hydrogen, hydroxy, or lower alkoxy. Of the compounds of formula 6, preferred intermediate compounds are those in which $R_7$ and $R_{10}$ are hydrogen.

In one method of preparing the substituted benzopyrano[4,3,2-cd]indazole compounds of this aspect of the invention having structural formula 2 above, 1-halo-4-nitro-9H-xanthen-9-one compounds of structural formula 6 above (where $R_5$, is nitro and $R_7$, $R_8$, $R_9$, and $R_{10}$ are as defined above) are reacted with hydrazines having the structure $R_2NHNH_2$ where $R_2$ is also as previously defined.

The reaction conditions can be varied widely. The reaction is usually carried out in a solvent at temperatures between about 25° C. to about 140° C. Suitable solvents for this reaction step include acetonitrile, 1,2-dichloroethane, tetrahydrofuran, methanol, or dimethylformamide.

The requisite substituted hydrazines are prepared by reaction of hydrazine with the appropriate alkyl halide $XR_2$ (where X is chlorine, bromine or iodine and $R_2$ is as previously defined) employing the method disclosed in J. Med. Chem., 7: 403 (1964), or by other methods known in the art as described below.

Compounds of structural formula 2 above wherein $R_5$ is amino are prepared by subjecting the compounds of structural formula 2 where $R_5$ is nitro to reduction. The reduction is carried out by suitable means, preferably by hydrogenation at room temperature using a palladium/charcoal catalyst in a solvent such as tetrahydrofuran, methanol, or acetic acid; tetrahydrofuran is preferred.

Compounds of formula 2 above where $R_5$ is $NHR_2$ (where $R_2$ is as previously defined) are prepared by reacting a compound of structural formula 2 (where $R_5$ is amino) with an alkyl halide of formula $XR_2$ (where X is chlorine, bromine, or iodine and $R_2$ is as previously defined). In those cases where the substituent group $R_2$ is sensitive to the conditions of alkylation, the group is protected prior to the alkylation reaction with an appropriate protecting group such as benzyl, with the protecting group being removed following such alkylation by methods known in the art such as hydrogenolysis.

The alkylation reaction between the compound of structural formula 2 (where $R_5$ is amino) and $XR_2$ is generally carried out in the absence of a solvent or in a suitable unreactive solvent such as chloroform or dimethylformamide. In the absence of a solvent, the reaction temperature may be about 150° C. When a solvent is employed, the reaction is carried out under reflux, at temperatures between about 60° C. and 150° C. A base such as triethylamine or potassium carbonate may be employed during the alkylation reaction as acid scavengers, but they are not essential.

Alternatively, compounds of structural formula 2 above (where R₅ is NHR₂) are prepared by reacting a compound of formula 2 (where R₅ is amino) with the appropriately substituted aldehyde, acetal, ketone, or ketal at reflux temperatures, for example, from about 65° C. to about 140° C. The resulting Schiff base intermediate is reduced with the appropriate reducing agent such as NaBH₄ or NaBH₃CN to produce the desired product.

The general methods detailed above for preparing compounds of this aspect of the invention are presented in schematic form in Reaction Sequence I below.

REACTION SEQUENCE I

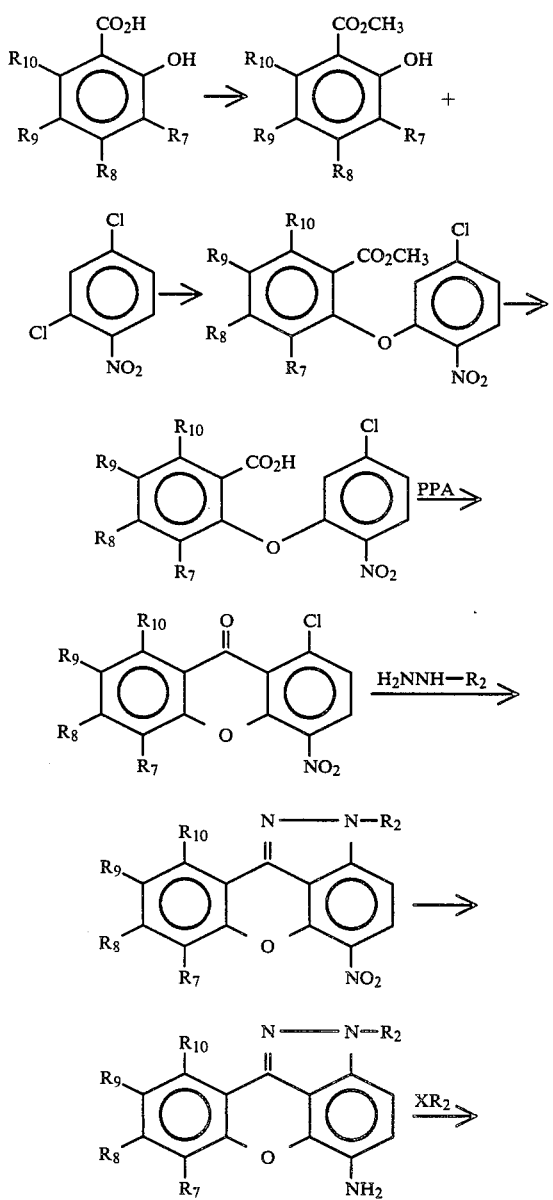

-continued
REACTION SEQUENCE I

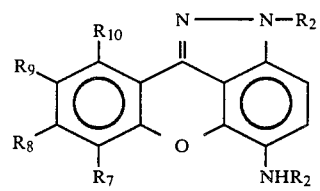

The substituted benzopyrano[4,3,2-cd]indazole compounds of this aspect of the invention range in color from beige to yellow. In the free base form they are generally crystalline solids which are stable under normal atmospheric conditions. The compounds typically have melting points in the range of about 100° C. to about 250° C.

The compounds are useful as pharmacological agents for the treatment of bacterical and fungal infections in warm-blooded animals as evidenced by their activity against a range of Gram-positive and Gram-negative bacteria and filamentous fungi. The activity of these compounds as antibacterial and antifungal agents was established by test procedures more fully set out below.

In addition to their antibacterial and antifungal activity, the substituted benzopyrano[4,3,2-cd]indazole compounds of this aspect of the invention demonstrate in vitro and in vivo activity against the L1210 and P388 murine leukemia cell lines. This antineoplastic activity is also evidenced by data collected from test procedures set out below.

In accordance with a second preferred sub-generic chemical compound aspect, the present invention provides substituted benzothiopyrano[4,3,2-cd]indazole compounds of formula 3

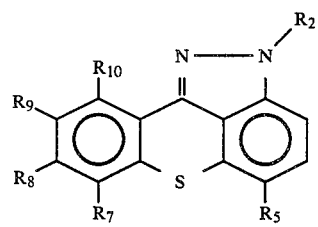

wherein the substituents R₇, R₈, R₉, and R₁₀ are independently hydrogen, hydroxy, alkoxy of from 1 to 4 carbon atoms (hereinafter referred to as "lower alkoxy"); wherein R₂ is —ANR'R" wherein A is a straight or branched alkylene chain of from 2 to 5 carbon atoms optionally substituted with hydroxyl; wherein R' and R" are hydrogen or are straight or branched alkyl of from 1 to 4 carbon atoms (hereinafter referred to as "lower alkyl") optionally substituted with hydroxyl, or where R' and R" taken together also represent

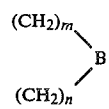

wherein m and n are each an integer of from 2 to 3 and B is a direct bond, or oxygen, sulfur, or NR‴ wherein R‴ is hydrogen or straight or branched alkyl of from 1 to 4 carbon atoms optionally substituted with hydroxyl;

and wherein $R_5$ is nitro, $NH_2$, $NHR_2$, or $NHR''''$ where $R''''$ is

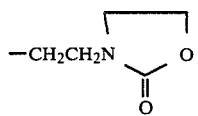

or is

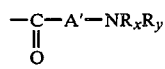

wherein A' is a straight or branched alkylene chain of from 1 to 5 carbon atoms, and $R_x$ and $R_y$ are independently hydrogen or straight or branched alkyl of from 1 to 4 carbon atoms optionally substituted with hydroxyl.

Preferred compounds within this sub-generic class of substituted benzothiopyrano[4,3,2-cd]indazole compounds, are compounds of structural formula 3 above where $R_7$, $R_8$, $R_9$, and $R_{10}$ are hydrogen. Within this group of preferred compounds are those where $R_5$ is nitro, and $R_2$ is as previously defined. Further, within this group, particularly preferred compounds are those where $R_7$, $R_8$, $R_9$, and $R_{10}$ are hydrogen, $R_5$ is nitro, and $R_2$ is —ANR'R'' where A is a straight or branched alkylene chain of from 2 to 5 carbon atoms optionally substituted with hydroxyl and where R' and R'' are straight or branched lower alkyl optionally substituted with hydroxyl.

Also preferred are compounds of structural formula 3 above where $R_7$, $R_8$, $R_9$, and $R_{10}$ are hydrogen, and $R_5$ is $NH_2$, $NHR_2$, or $NHR''''$ where $R''''$ is

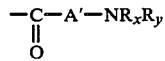

where A' is a straight or branched alkylene chain of from 2 to 5 carbon atoms optionally substituted with hydroxyl, and $R_x$ and $R_y$ are independently hydrogen or straight or branched alkyl of from 1 to 4 carbon atoms optionally substituted with hydroxyl.

Other preferred compounds within this sub-generic class of substituted benzothiopyrano[4,3,2-cd]indazole compounds, are compounds of structural formula 8

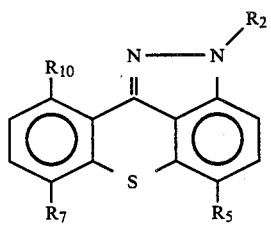

where $R_2$ and $R_5$ are as previously defined and $R_7$ and $R_{10}$ are hydrogen, hydroxy, or lower alkoxy, at least one of $R_7$ or $R_{10}$ being hydroxy or lower alkoxy. Within this preferred group of compounds, are compounds where $R_5$ is nitro, amino, or $NHR_2$ where $R_2$ is as previously defined.

Another preferred group of substituted benzothiopyrano[4,3,2-cd]indazole compounds of this sub-generic aspect of the invention are compounds of structural formula 9

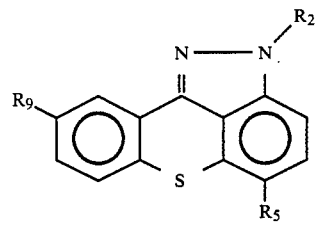

where $R_2$ and $R_5$ are as previously defined, $R_7$, $R_8$, and $R_{10}$ are hydrogen, and $R_9$ is hydroxy or lower alkoxy. Particularly preferred are those compounds where $R_9$ is hydroxy.

Within this group of preferred compounds are those where $R_5$ is nitro, amino, or $NHR_2$ where $R_2$ is as previously defined.

Most preferred, for their pharmacological properties, are compounds in accordance with the present invention having the names:

2-[[2-[[2-[2-(Diethylamino)ethyl]-2H-[1]benzothiopyrano[4,3,2-cd]indazol-5-yl]amino]ethyl]amino]ethanol;

2-[[2-[5-[[2-[(2-Hydroxyethyl)amino]ethyl]amino]-2H-[1]benzothiopyrano[4,3,2-cd]indazol-2-yl]ethyl]amino]-ethanol;

N-[2-[2-(Diethylamino)ethyl]-2H-[1]benzothiopyrano-[4,3,2-cd]indazol-5-yl]-1,2-ethanediamine;

N,N-Diethyl-5-nitro-2H-[1]bensothiopyrano[4,3,2-cd]-indazole-2-ethanamine;

5-Nitro-2H-[1]benzothiopyrano[4,3,2-cd]indazole-2-ethanamine;

2-[[2-(5-Nitro-2H-[1]benzothiopyrano[4,3,2-cd]-indazol-2-yl)ethyl]amino]ethanol;

5-Amino-N,N-diethyl-2H-[1]benzothiopyrano[4,3,2-cd]-indazole-2-ethanamine;

N,N-Diethyl-9-methoxy-5-nitro-2H-[1]benzothiopyrano-[4,3,2-cd]indazole-2-ethanamine;

N-[2-[2-(Diethylamino)ethyl]-2H-[1]benzothiopyrano-[4,3,2-cd]indazol-5-yl]-1,3-propanediamine;

5-Amino-N,N-dimethyl-2H-[1]benzothiopyrano[4,3,2-cd]-indazole-2-propanamine;

N,N-Dimethyl-5-nitro-2H-[1]benzothiopyrano[4,3,2-cd]-indazole-2-propanamine;

2-[[2-(5-Amino-2H-[1]benzothiopyrano[4,3,2-cd]indazol-2-yl)ethyl]amino]ethanol;

2-[[2-[5-[[2-(Diethylaminoethyl]amino]-2H-[1]benzothiopyrano[4,3,2-cd]indazol-2-yl]ethyl]amino]ethanol;

2-[[2-[[2-(2-Aminoethyl)-2H-[1]benzothiopyrano-[4,3,2-cd]indazol-5-yl]amino]ethyl]amino]ethanol;

5-Amino-2-[2-(diethylamino)ethyl]-2H-[1]benzothiopyrano[4,3,2-cd]indazol-9-ol;

2-[2-(Diethylamino)ethyl]-5-[[2-[(2-hydroxyethyl)-amino]ethyl]amino]-2H-[1]benzothiopyrano[4,3,2-cd]indazol-9-ol;

N-[2-[3-(Dimethylamino)propyl]-2H-[1]benzothiopyrano-[4,3,2-cd]indazol-5-yl]-1,2-ethanediamine;

N,N-Diethyl-7-methoxy-5-nitro-2H-[1]benzothiopyrano-[4,3,2-cd]indazol-2-ethanamine;

5-Amino-N,N-diethyl-7-methoxy-2H-[1]benzothiopyrano-[4,3,2-cd]indazol-2-ethanamine;

5-[2-(Aminoethyl)amino]-2-[2-(diethylamino)ethyl]-2H-[1]benzothiopyrano[4,3,2-cd]indazol-7-ol, hydrobromide salt;

5-Amino-2-[2-(diethylamino)ethyl]-2H-[1]benzothi-
opyrano[4,3,2-cd]indazol-7-ol;
N,N-Diethyl-8-methoxy-5-nitro-2H-[1]benzothi-
opyrano-[4,3,2-cd]indazole-2-ethanamine;
5-Amino-N,N-diethyl-8-methoxy-2H-[1]benzothi-
opyrano-[4,3,2-cd]indazole-2-ethanamine;
N-[2-[2-(Diethylamino)ethyl]-8-methoxy-2H-[1]benzo-
thiopyrano[4,3,2-cd]indazol-5-yl]-1,2-ethanediamine,
hydrobromide salt;
5-[2-(Aminoethyl)amino]-2-[2-(diethylamino)ethyl]-2H-
[1]benzothiopyrano[4,3,2-cd]indazol-8-ol, hydrobro-
mide salt;
5-Amino-2-[2-(diethylamino)ethyl]-2H-[1]benzothi-
opyrano[4,3,2-cd]indazol-8-ol;
5-[(2-Aminoethyl)amino]-2-[2-(diethylamino)ethyl]-2H-
[1]benzothiopyrano[4,3,2-cd]indazol-8-ol, hydrochlo-
ride salt;
N,N-Diethyl-10-methoxy-5-nitro-2H-[1]benzothi-
opyrano[4,3,2-cd]indazole-2-ethanamine;
5-Amino-N,N-diethyl-10-methoxy-2H-[1]benzothi-
opyrano-[4,3,2-cd]indazole-2-ethanamine;
5-[2-(Aminoethyl)amino]-2-[2-(diethylamino)ethyl]-2H-
[1]-benzothiopyrano[4,3,2-cd]indazol-10-ol, hydro-
bromide salt;
5-Amino-2-[2-(diethylamino)ethyl]-2H-[1]benzothi-
opyrano[4,3,2-cd]indazol-10-ol;
2-[2-(Diethylamino)ethyl]-5-nitro-2H-[1]benzothi-
opyrano[4,3,2-cd]indazol-9-ol;
5-Amino-2-[2-(diethylamino)ethyl]-2H-[1]benzothi-
opyrano[4,3,2-cd]indazol-9-ol; and
5-[(2-Aminoethyl)amino]-2-[2-(diethylamino)ethyl]-2H-
[1]benzothiopyrano[4,3,2-cd]indazol-9-ol;
2-Amino-N-[2-[2-(diethylamino)ethyl]-2H-[1]benzothi-
opyrano[4,3,2-cd]indazol-5-yl]acetamide;
and the pharmaceutically acceptable salts thereof.

Certain of the compounds of the present invention are also useful as intermediates for the preparation of the preferred species; more specifically, those compounds are useful as intermediates which have structural formula 3 above where $R_5$ represents $NO_2$ or $NH_2$ and such compounds where reactive or sensitive functional groups such as hydroxyl or amino are protected by protecting groups such as benzyl or acyl.

In one method of preparing the substituted benzothiopyrano[4,3,2-cd]indazole compounds of this sub-generic aspect of the present invention, 1-halo-4-nitro-9H-thioxanthen-9-ones of structural formula 10 [see S. Archer et al., *J. Am. Chem. Soc.*, 74: 4296 (1952)]

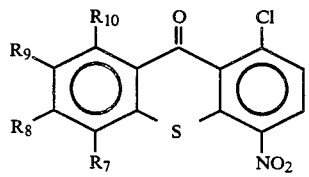

where $R_7$, $R_8$, $R_9$, and $R_{10}$ are as defined above, are reacted with hydrazines having the structural formula $R_2NHNH_2$ where $R_2$ is also as previously defined. The reaction conditions can be varied widely. The reaction is usually carried out in a solvent at temperatures of between about 25° C. and 140° C. Suitable solvents for this purpose are xylene, pyridine, or dimethylformamide.

The requisite hydrazines are prepared by reaction of hydrazine with the appropriate alkyl halide $XR_2$ (where X is chlorine, bromine, or iodine, and $R_2$ is as previously defined) employing the method disclosed in *J. Med. Chem.*, 7: 403 (1964), or by other methods known in the art as described in the Examples below.

Compounds of structural formula 3 above where $R_5$ is amino are prepared by subjecting the compounds of structural formula 3 where $R_5$ is nitro to reduction. The reduction is carried out by suitable means, preferably by hydrogenation at room temperature using a palladium/charcoal catalyst in a solvent such as tetrahydrofuran, methanol, or acetic acid; acetic acid is preferred.

Compounds of formula 3 above where $R_5$ is $NHR_2$ (where $R_2$ is as previously defined) are prepared by reacting a compound of structural formula 3 (where $R_5$ is amino) with an alkyl halide of formula $XR_2$ (where X is chlorine, bromine, or iodine and $R_2$ is as previously defined). In those cases where the substituent group $R_2$ is sensitive to the conditions of alkylation, the group is protected prior to the alkylation reaction with an appropriate protecting group such as benzyl, with the protecting group being removed following such alkylation by methods known in the art such as hydrogenolysis.

The alkylation reaction between the compound of structural formula 3 (where $R_5$ is amino) and $XR_2$ is generally carried out in the absence of a solvent or in a suitable unreactive solvent such as chloroform or dimethylformamide. In the absence of a solvent, the reaction temperature may be about 150° C. When a solvent is employed, the reaction is carried out under reflux, at temperatures between about 60° C. and 150° C. A base such as triethylamine or potassium carbonate may be employed during the alkylation reaction as acid scavengers, but they are not essential.

Alternatively, compounds of structural formula 3 above (where $R_5$ is $NHR_2$) are prepared by reacting a compound of formula 3 (where $R_5$ is amino) with the appropriately substituted aldehyde, acetal, ketone, or ketal at reflux temperatures, for example, from about 65° C. to about 140° C. The resulting Schiff base intermediate is reduced with the appropriate reducing agent such as $NaBH_4$ or $NaBH_3CN$ to produce the desired product.

Compounds of structural formula 3 above where $R_5$ is

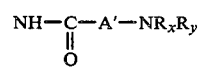

where A', $R_x$ and $R_y$ are as previously defined, are prepared by reacting a compound of structural formula 3 where $R_5$ is $NH_2$ with a reactive derivative of the appropriate carboxylic acid, the appropriate acid halide, or the anhydride. In those instances where $R_x$ and/or $R_y$ contain a functional group sensitive to the acylation reaction, such groups are protected in the conventional manner prior to the acylation reaction by protective groups such as benzyl which are removed later by techniques well known in the art such as hydrogenolysis.

The acylation reaction is carried out in the conventional manner, for example by reacting the compounds in a solvent such as pyridine at a temperature of between about 25° C. to about 115° C.

The starting materials for preparing the substituted benzothiopyrano[4,3,2-cd]indazole compounds of this aspect of the invention where $R_8$ and $R_9$ are hydrogen and $R_7$ and $R_{10}$ are hydroxy or lower alkoxy are prepared by the methods illustrated schematically in Reaction Sequence II.

The intermediate compound, 11, prepared by known procedures [see, for example, P. K. Bannerjee et al., J. Indian, Chem. Soc., 86: 257 (1959)] is diazotized by treatment with sodium nitrite, and then reacted with the potassium salt of ethylxanthic acid, and hydrolyzed to give compound 12. Reaction of 12 with 2,4-dichloronitrobenzene affords compound 13. Compound 13 is ring-closed to a compound 14 by the action of a mixture of trifluoroacetic acid/trifluoroacetic acid anhydride.

Alternatively, compound 13 is reacted with thionyl chloride and subsequently ring-closed by the action of anhydrous aluminum chloride in nitrobenzene at 70° C. to give the intermediate 15.

Compounds of structural formula 16 are further converted, if desired, to compounds where the 5-nitro group is reduced to amino, or compounds where the 5-amino group is alkylated or acylated by methods described above and well known in the art.

An alternative route for preparing compounds of structural formula 16 is shown schematically in Reaction Sequence III. The method comprises converting 2,5-dimethoxybenzenamine 17 to the corresponding sulfhydryl compound 18 through the diazonium intermediate in a manner analogous to that described above. Compound 18 is reacted with 2,6-dichloro-3-nitrobenzoic acid [Lehmstadt et al., Ber., 70b: 1526 (1937)] to

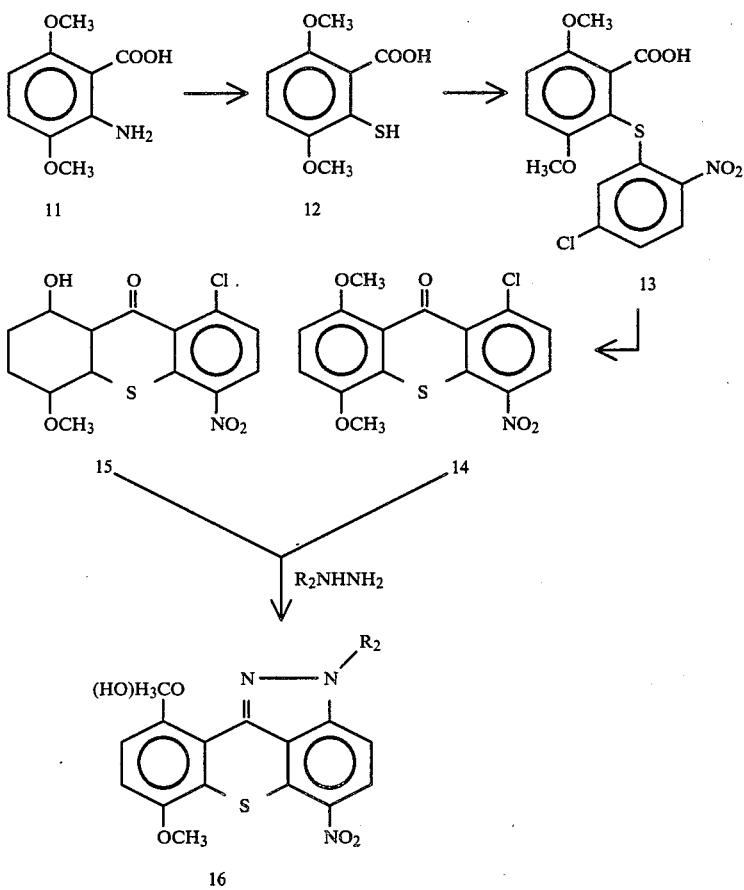

REACTION SEQUENCE II

Compound 14 or 15 is then reacted with the substituted hydrazine to produce compounds of structural formula 16.

To prepare compounds analogous to compound 14, but where $R_7$ and $R_{10}$ are alkoxy of from 2 to 4 carbon atoms, 2,5-dihydroxybenzoic acid is alkylated, subsequently nitrated, and then reduced by conventional methods to give 2-amino-3,6-dialkoxybenzoic acid. The resulting intermediate compound is further converted to a compound analogous to compound 14 by the methods described above and shown schematically in Reaction Sequence II.

obtain compound 19. Compound 19 is ring closed in a manner analogous to that described above to obtain compound 14 which further reacted as detailed in Reaction Sequence II to obtain compound 16.

In a method of preparing compounds of structural formula 9 above (where $R_2$ is as previously defined, $R_5$ is nitro, $R_7$, $R_8$, and $R_{10}$ are hydrogen, and $R_9$ is hydroxy or lower alkoxy), 5-(lower)alkoxy-2-aminobenzoic acid 20 [prepared by known methods, N. B. Chapman et al., J. Chem. Soc., 890 (1947) and German Pat. No. 2,525,050] is diazotized, treated with the potassium salt of ethylxanthic acid, and hydrolyzed to produce compound 21. Reaction of 21 with 2,4-dichloronitrobenzene affords compound 22 which is

REACTION SEQUENCE III

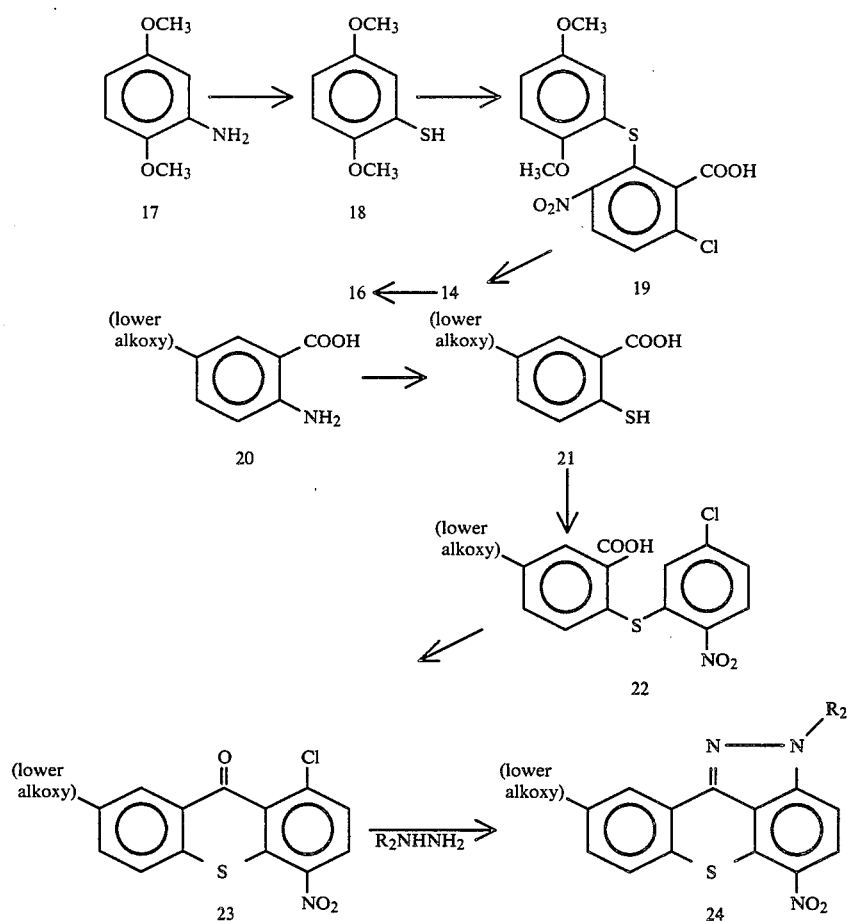

chlorinated with thionyl chloride and ring closed by the action of anhydrous aluminum chloride in nitrobenzene at 70° C. to give the intermediate 23. Reaction of 23 with the appropriate substituted hydrazine compound affords compounds of structure 24.

Compounds of structure 24 where $R_5$ is nitro can be subsequently reduced to the corresponding amine compounds by methods described above. The amine compounds are subsequently converted, if desired, to the alkylated or acylated amine compounds by methods previously described.

Compounds of structural formula 9 where $R_9$ is hydroxy are prepared by first preparing the corresponding compounds where $R_9$ is benzyloxy and $R_5$ is nitro. The sequence of reactions described above is then employed to obtain compounds where $R_5$ is amino, $NHR_2$ (where $R_2$ is as previously described) and ultimately removing the protecting benzyl group in the conventional manner to yield compounds where $R_9$ is hydroxy.

The substituted benzothiopyrano[4,3,2-cd]indazole compounds of this aspect of the invention range in color from beige to orange. In the free base form they are generally crystalline solids which are stable under normal atmospheric conditions. The compounds typically have melting points in the range of about 100° C. to about 250° C.

The compounds are useful as pharmocological agents for the treatment of bacterical and fungal infections in warm-blooded animals as evidenced by their activity against a range of Gram-positive and Gram-negative bacteria and filamentous fungi. The activity of these compounds as antibacterial and antifungal agents was established by test procedures more fully set out below.

In addition to their antibacterial and antifungal activity, the substituted benzothiopyrano[4,3,2-cd]indazole compounds of this aspect of the invention demonstrate in vitro and in vivo activity against the L1210 and P388 murine leukemia cell lines. This antineoplastic activity is also evidenced by data collected from test procedures set out below.

In accordance with a third preferred sub-generic chemical compound aspect, the present invention provides substituted benzoselenino[4,3,2-cd]indazole compounds of structural formula 4

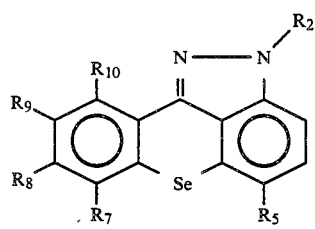

where the substituents $R_7$, $R_8$, $R_9$, and $R_{10}$ are independently hydrogen, hydroxy, alkoxy of from 1 to 4 carbon atoms where $R_2$ is $-ANR'R''$ wherein A is a straight or branched alkylene chain of from 2 to 5 carbon atoms optionally substituted with hydroxyl; where R' and R" are hydrogen or are straight or branched alkyl of from 1 to 4 carbon atoms optionally substituted with hydroxyl, or where R' and R" taken together also represent

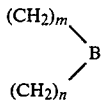

where m and n are each an integer of from 2 to 3 and B is a direct bond, or oxygen, sulfur, or NR''' where R''' is hydrogen or straight or branched alkyl of from 1 to 4 carbon atoms optionally substituted with hydroxyl; and where $R_5$ is nitro, $NH_2$, $NHR_2$, or NHR'''' where R'''' is

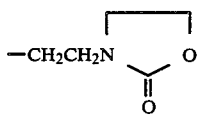

or is

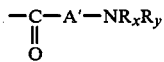

where A' is a straight or branched alkylene chain of from 1 to 5 carbon atoms, and $R_x$ and $R_y$ are independently hydrogen or straight or branched alkyl of from 1 to 4 carbon atoms optionally substituted with hydroxyl.

Preferred compounds within this sub-generic class of substituted benzoselenino[4,3,2-cd]indazole compounds, are compounds of structural formula 4 above where $R_7$, $R_8$, $R_9$, and $R_{10}$ are hydrogen and $R_5$ is nitro, amino, or $NHR_2$ where $R_2$ is as previously defined.

Other preferred compounds include compounds of structural formula 4 above where $R_7$, $R_8$, and $R_{10}$ are hydrogen, $R_{10}$ is hydroxy or lower alkoxy, and $R_2$ and $R_5$ are as previously defined, particularly where $R_5$ is nitro, amino, or $NHR_2$.

In another preferred aspect, benzoselenino[4,3,2-cd]indazole compounds of the invention include compounds having structural formula 4 above where $R_7$, $R_9$, and $R_{10}$ are hydrogen, $R_8$ is hydroxy or lower alkoxy, and $R_2$ and $R_5$ are as previously defined, particularly where $R_5$ is nitro, amino, or $NHR_2$.

Most preferred, for their pharmacological properties, are substituted benzoselenino[4,3,2-cd]indazole compounds of this sub-generic aspect of the invention having the names:

N,N-Diethyl-5-nitro-2H-[1]benzoselenino[4,3,2-cd]-indazole-2-ethanamine;

5-Amino-N,N-diethyl-2H-[1]benzoselenino[4,3,2-cd]indazole-2-ethanamine;

N-[2-[2-(Diethylamino)ethyl]-2H-[1]benzoselenino[4,3,2-cd]indazol-5-yl]-1,2-ethanediamine;

N-[2-[2-(Diethylamino)ethyl]-9-methoxy-2H-[1]benzoselenino[4,3,2-cd]indazol-5-yl]ethanediamine;

2-[[2-[[2-[2-(Diethylamino)ethyl]2H-[1]-benzoselenino-[4,3,2-cd]indazol-5-yl]amino]ethyl]amino]ethanol;

2-[[2-[5-[[2-[(2-Hydroxyethyl)amino]ethyl]amino]-2H-[1]benzoselenino[4,3,2-cd]indazol-2-yl]ethyl]amino]ethanol;

N,N-Diethyl-5-[[2-(diethylamino)ethyl]amino]-2H-[1]benzoselenino[4,3,2-cd]indazole-2-ethanamine;

N-[2-[2-(Diethylamino)ethyl]-2H-[1]benzoselenino-[4,3,2-cd]indazol-5-yl]-1,3-propanediamine;

5-[(2-Aminoethyl)amino]-2-[2-(1-pyrrolidinyl)ethyl]-2H-[1]benzoselenino[4,3,2-cd]indazole;

2-[2-(Diethylamino)ethyl]-5-nitro-2H-[1]benzoselenino[4,3,2-cd]indazol-9-ol;

2-[2-(Diethylamino)ethyl]-5-nitro-2H-[1]benzoselenino[4,3,2-cd]indazol-8-ol;

5-[(2-Aminoethyl)amino]-2-[2-(diethylamino)ethyl]-2H-[1]benzoselenino[4,3,2-cd]indazol-9-ol;

5-[(2-Aminoethyl)amino]-2-[2-(diethylamino)ethyl]-2H-[1]benzoselenino[4,3,2-cd]indazol-8-ol;

2-[2-(Diethylamino)ethyl]-5-[[2-[(2-hydroxyethyl)amino]ethyl]amino]-2H-[1]benzoselenino[4,3,2-cd]indazol-8-ol;

2-[2-(Diethylamino)ethyl]-5-[[2-[2-hydroxyethyl)amino]ethyl]-2H-[1]benzoselenino[4,3,2-cd]indazol-8-ol;

2-[2-[(2-Hydroxyethyl)amino]ethyl]-5-[[2-[(2-hydroxyethyl)amino]ethyl]amino]-2H-[1]benzoselenino[4,3,2-cd]-indazol-8-ol;

2-[2-(Diethylamino)ethyl]-5-[[2-[(2-hydroxyethyl)amino]ethyl]amino]-2H-[1]benzoselenino[4,3,2-cd]indazol-9-ol;

2-[2-[(2-Hydroxyethyl)amino]ethyl]-5-[[2-[(2-hydroxyethyl)amino]ethyl]amino]-2H-[1]benzoselenino[4,3,2-cd]-indazol-9-ol;

5-[(3-Aminopropyl)amino]-2-(diethylamino)ethyl]-2H-[1]benzoselenino[4,3,2-cd]indazol-9-ol;

5-[(Aminoethyl)amino]-2-[2-(diethylamino)ethyl]-2H-[1]benzoselenino[4,3,2-cd]indazol-10-ol;

2-[2-(Diethylamino)ethyl]-5-[[2-[(2-hydroxyethyl)amino]ethyl]amino]-2H-[1]benzoselenino[4,3,2-cd]indazol-10-ol;

2-[2-[(2-Hydroxyethyl)amino]ethyl-5-[[2-(2-hydroxyethyl)amino]ethyl]amino]-2H-[1]benzoselenino[4,3,2-cd]-indazol-10-ol;

5-[(2-Aminoethyl)amino]-2-[2-(diethylamino)ethyl]-2H-[1]benzoselenino[4,3,2-cd]indazol-7,8-diol;

2-[2-(Diethylamino)ethyl]-5-[[2-[(2-hydroxyethyl)amino]ethyl]amino]-2H-[1]benzoselenino[4,3,2-cd]indazol-7,8-diol;

2-[2-[(2-Hydroxyethyl)amino]ethyl]-5-[[2-[(2-hydroxyethyl)amino]ethyl]amino]-2H-[1]benzoselenino-[4,3,2-cd]indazol-7,8-diol;

5-[(2-Aminoethyl)amino]-2-[2-diethylamino)ethyl]-2H-[1]benzoselenino[4,3,2-cd]indazol-8,10-diol;

2-[2-(Diethylamino)ethyl]-5-[[2-[(2-hydroxyethyl)amino]ethyl]amino]-2H-[1]benzoselenino[4,3,2-cd]indazol-8,10-diol;

and the pharmaceutically acceptable salts thereof.

The invention in another aspect also includes novel intermediate compounds of structural formula 23

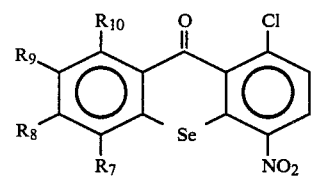

wherein the substituent groups $R_7$, $R_8$, $R_9$, and $R_{10}$ are independently hydrogen, hydroxy, or lower alkoxy. Of the compounds of formula 23, preferred intermediate compounds are those in which $R_7$, $R_8$ and $R_{10}$ are hydrogen and $R_9$ is hydroxy or lower alkoxy, particularly hydroxy.

In one method of preparing the substituted benzoselenino[4,3,2-cd]indazole compounds of this aspect of the invention having structural formula 4 above, substituted 1-halo-4-nitro-9H-selenoxanthen-9-one compounds of structural formula 23 above (where the substituent groups $R_7$, $R_8$, $R_9$, and $R_{10}$ are as defined above) are reacted with hydrazines having the structure $R_2NHNH_2$ where $R_2$ is as previously defined.

The reaction conditions can be varied widely. The reaction is usually carried out in a solvent at temperatures between about 25° C. to about 140° C. Suitable solvents for this reaction step include xylene, pyridine or dimethylformamide.

The requisite substituted hydrazines are prepared by reaction of hydrazine with the appropriate alkyl halide $XR_2$ (where X is chlorine, bromine or iodine and $R_2$ is as previously defined) employing the method disclosed in *J. Med. Chem.*, 7: 403 (1964), or by other methods known in the art as described below.

The 1-halo-4-nitro-9H-selenoxanthen-9-ones are prepared by cyclization of the corresponding 2-[(5-chloro-2-nitrophenyl)seleno]benzoic acids 26 preferably with methanesulfonic acid or, alternatively, with phosphorus pentoxide and hexamethyldisiloxane.

The requisite benzoic acids are prepared by the reaction of an o-selenocyanobenzoic acid 24 with a 2,4-dichloro-nitrobenzene 25. The process is depicted schematically in Reaction Sequence IV.

REACTION SEQUENCE IV

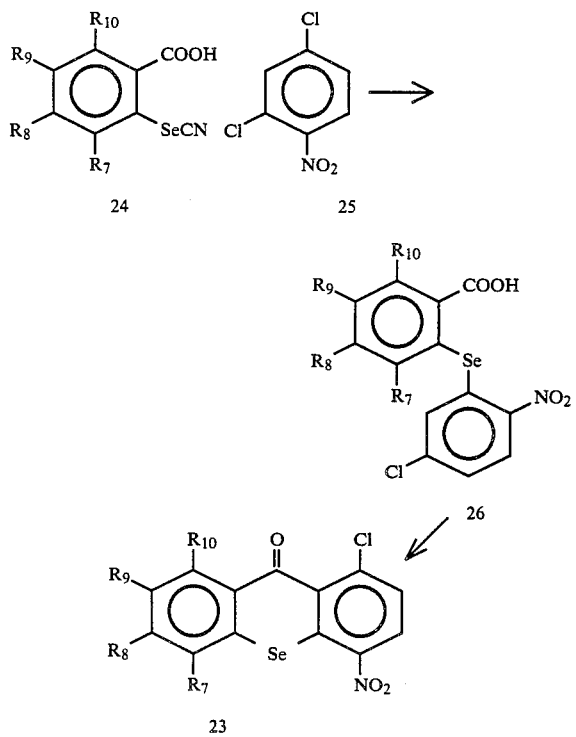

Compounds of structural formula 4 above where $R_5$ is amino are prepared by subjecting the compounds of structural formula 4 where $R_5$ is nitro to reduction. The reduction is carried out by suitable means, preferably by hydrogenation at room temperature using a palladium/-charcoal catalyst in a solvent such as tetrahydrofuran, methanol, or acetic acid; acetic acid is preferred.

Compounds of formula 4 above where $R_5$ is $NHR_2$ (where $R_2$ is as previously defined) are prepared by reacting a compound of structural formula 4 (where $R_5$ is amino) with an alkyl halide of formula $XR_2$ (where X is chlorine, bromine, or iodine and $R_2$ is as previously defined). In those cases where the substituent group $R_2$ is sensitive to the conditions of alkylation, the group is protected prior to the alkylation reaction with an appropriate protecting group such as benzyl, with the protecting group being removed following such alkylation by methods known in the art such as hydrogenolysis.

The alkylation reaction between the compound of structural formula 4 (where $R_5$ is amino) and $XR_2$ is generally carried out in the absence of a solvent or in a suitable unreactive solvent such as chloroform or dimethylformamide. In the absence of a solvent, the reaction temperature may be about 150° C. When a solvent is employed, the reaction is carried out under reflux, at temperatures between about 60° C. and 150° C. A base such as triethylamine or potassium carbonate may be employed during the alkylation reaction as an acid scavenger, but such is not essential.

Alternatively, compounds of structural formula 4 above (where $R_5$ is $NHR_2$) are prepared by reacting a compound of formula 4 (where $R_5$ is amino) with the appropriately substituted aldehyde, acetal, ketone, or ketal at reflux temperatures, for example, from about 65° C. to about 140° C. The resulting Schiff base intermediate is reduced with the appropriate reducing agent such as $NaBH_4$ or $NaBH_3CN$ to produce the desired product.

Compounds of structural formula 4 above where $R_5$ is

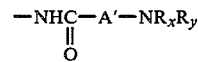

where A', $R_x$ and $R_y$ are as previously defined, are prepared by reacting a compound of structural formula 4 where $R_5$ is $NH_2$ with a reactive derivative of the approriate carboxylic acid, the appropriate acid halide, or the anhydride. In those instances where $R_x$ and/or $R_y$ contain a functional group sensitive to the acylation reaction, such groups are protected in the conventional manner prior to the acylation reaction by protective groups such as benzyl which are removed later by techniques well known in the art such as hydrogenolysis.

The acylation reaction is carried out in the conventional manner, for example by reacting the compounds in a solvent such as pyridine at a temperature of between about 25° C. to about 115° C.

The substituted benzoselenino[4,3,2-cd]indazole compounds of this aspect of the invention range in color from beige to yellow. They are generally stable under normal atmospheric conditions and typically have melting points between about 100° C. and 250° C.

The substituted compounds are useful as pharmacological agents for the treatment of bacterial and fungal infections in warm-blooded animals as evidenced by their activity against a range of gram-positive and gram-negative bacteria and filamentous fungi. The activity of these compounds as antibacterial and antifungal agents was established by test procedures more fully set out below.

In addition to their antibacterial and antifungal activity, the substituted benzoselenino[4,3,2-cd]indazole compounds of this aspect of the invention demonstrate in vitro and in vivo activity against the L1210 and P388 murine leukemia cell lines. This antineoplastic activity is also evidenced by data collected from test procedures set out below.

TEST PROTOCOLS

Antibacterial/antifungal Test Protocol

In one antibacterial/antifungal test (designated ABF), the activities of selected compounds of the present invention having structural formula 1 above (where X is oxygen, sulfur, or selenium, and $R_2$, $R_5$, $R_7$, $R_8$, $R_9$, and $R_{10}$ are as previously described), were determined in an in vitro antibacterial/antifungal test which employs the standard agar-disk diffusion assay. Paper discs impregnated with the test compounds are placed on a suitable agar nutrient medium which has been inoculated with a given microorganism. After incubation of each culture with the test compound, the zone of inhibition of growth of the microorganism is measured. The zone diameter (in millimeters) of compounds ranges from a minimum of 13.5 mm to a high of 60 mm, with greater diameters reflecting higher activity. In the data Tables below, for convenience, values are reported for two Gram-negative bacteria (*Aerobacter aerogenes* 0126, and *Escherichia coli* 04863), two Gram-positive bacteria (*Bacillus subtilis* 04555, and *Streptococcus faecalis* 05045 utilizing AM-09 culture medium), and one mycelia fungus (*Penicillium avellaneum* M2988).

A second antibacterial/antifungal test (designated ABMF), employed to determine the activity of representative compounds of the present invention is a recognized standard microdilution susceptibility procedure in Mueller-Hinton broth against Gram-positive and Gram-negative bacterial and fungal organisms. The procedure is a modification of the procedure reported in *Manual of Clinical Microbiology*, E. H. Lennetts, Ed., American Society for Microbiology, Washington, D.C., 1980 at pages 463–474.

In the test, a given bacterial culture is used to inoculate several wells of a microdilution tray containing growth medium and test compounds. The test compound resides in the wells at serial dilution concentrations of 1000, 333, 111, 37, 12, 4, 1.4, and 0.46 micrograms/milliliter.

The inolculated trays are sealed, incubated with blank controls at 37° C. for 16–24 hours, and then read to determine the minimum inhibitory concentration (MIC) required to completely inhibit the growth of the microorganism. MIC values lower than 333 micrograms/milliliter are considered indicative of antibacterial or antifungal activity.

The test is typically run with a number of species of Gram-positive and Gram-negative bacteria, yeasts, and filamentous fungi. However, in the Tables that follow, for convenience, the values relating to inhibition of *E. coli*, Corynebacterium Sp. ATCC 21698, *S. typhimurium*, *S. pneumoniae*, and *R. aurantiaca* are reported.

In Vitro Antineoplastic Test Protocol

The activities of several representative compounds of the present invention having structural formula 1 above (where X is oxygen, sulfur, or selenium, and $R_2$, $R_5$, $R_7$, $R_8$, $R_9$, and $R_{10}$ are as previously described), were tested against the L1210 murine leukemia cell line in vitro.

A cell culture of the L1210 murine leukemia cell line is grown in RPMI 1640 culture medium supplemented with 5% fetal bovine serum containing gentamicin (50 micrograms per milliliter). Dilutions of the test compound are prepared in the appropriate solvent and 20 microliters of each dilution are added to a 24-well Linbro tissue culture plate, followed by the addition of 2.0 ml of cell suspension containing $3 \times 10^4$ cells/milliliter. Solvent and medium controls are included in each test.

After incubation at 37° C. for three days in 5% $CO_2$, the contents of each well are removed and the cells are counted in a ZBI Coulter counter. The percent growth is calculated relative to the controls and the levels of drug activity are expressed as $ID_{50}$ (the concentration required to inhibit cell growth by 50%) in terms of moles/liter.

In Vivo Antineoplastic Test Protocol

The activities of several representative compounds of the present invention having structural formula 1 above (where X is oxygen, sulfur, or selenium, and $R_2$, $R_5$, $R_7$, $R_8$, $R_9$, and $R_{10}$ are as previously described), were tested against the P388 murine leukemia cell line in vivo. This protocol tests the effectiveness of a given compound to inhibit the growth of the transplanted P388 murine leukemia cell line in male and female $CD_2F_1$ mice. Each test included a group of six or seven mice. The test is described in detail in *Cancer Chemotherapy Reports*, Part 3, Volume 3, page 1-ff (1972).

The tumor cell line is transplanted into the test animals by intraperitoneal injection of ascitic fluid containing the cell line. The test compounds are administered to the test animals intraperitoneally once daily for five consecutive days at various doses following tumor inoculation. The animals are weighed, and survivors are recorded on a regular basis for thirty days.

A compound is designated "toxic" if, at a given dose, no animal survives after four days following first injection of the test compound. A ratio of survival time for treated (T) animals relative to control (C) animals is calculated for each non-toxic dose. A criterion for efficacy is a ratio of $(T/C) \times 100$ equal to or greater than 125.

The results of these tests for representative examples of the substituted benzo pyrano[4,3,2-cd]indazole, benzothio-pyrano[4,3,2-cd]indazole, and benzoselenino-[4,3,2-cd]indazole of the present invention appear in Tables 1, 2, and 3, respectively.

TABLE 1A

Antitumor, Antibacterial, and Antifungal Data on
2,5-Disubstituted 2H—[1]benzopyrano[4,3,2-cd]indazoles

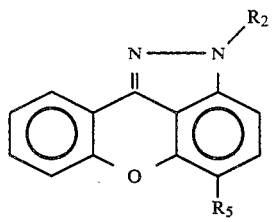

| $R_2$ | $R_5$ | L1210 in vitro $ID_{50}$ (M) | HCA-4 in vitro $ID_{50}$ (M) | P388 in vivo Dose (mg/kg) | P388 in vivo T/C × 100 | ABF Zone Diameter (Conc. in mg/ml) A. Aero- genes | B. E. Coli | S. Sub- tilis | P. Fae- calis | Avell- aneum |
|---|---|---|---|---|---|---|---|---|---|---|
| $CH_2CH_2NEt_2$ | $NO_2$ | $1.9 \times 10^{-6}$ | $1 \times 10^{-6}$ | 200 | 211 | — | — | 14 (.5) | 15 (.5) | 0 (3) |
|  |  |  |  | 100 | 138 |  |  |  |  |  |
| $CH_2CH_2NHCH_2CH_2OH$ | $NO_2$ | $4 \times 10^{-7}$ | $5 \times 10^{-7}$ | 50 | 141 | — | — | 17 (.1) | 17 (.5) | 19 (.1) |
| $CH_2CH_2NEt_2$ | $NH_2$ | $1.3 \times 10^{-6}$ | $2.4 \times 10^{-6}$ |  |  |  |  |  |  |  |
| $CH_2CH_2NEt_2$ | $NHCH_2CH_2NH_2$ | $8 \times 10^{-8}$ | $1.6 \times 10^{-7}$ | 25 | 216 | — | — | 14 (.5) | 16 (3) | 0 (3) |
|  |  |  |  | 12.5 | 174 |  |  |  |  |  |

TABLE 1B

Antitumor, Antibacterial, and Antifungal Data on
2,5,8-Trisubstituted 2H—[1]benzopyrano[4,3,2-cd]indazoles

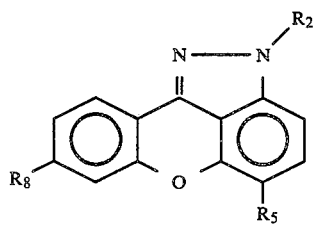

| $R_8$ | $R_2$ | $R_5$ | L1210 in vitro $ID_{50}$ (M) | ABMF Minimal Inhibitory Concentration (μ/ml) | | | | |
|---|---|---|---|---|---|---|---|---|
|  |  |  |  | E. coli | S. typhimurium | Corynebacterium sp. | S. pneumoniae | R. aurantiaca |
| $CH_3O$ | $CH_2CH_2N(Et)_2$ | $NO_2$ | $2.2 \times 10^{-6}$ | <0.46 | 37 | <0.46 | <0.46 | 333 |
| HO | $CH_2CH_2N(Et)_2$ | $NO_2$ | $8.7 \times 10^{-7}$ | 1.4 | 12.3 | <0.46 | <0.46 | >1000 |

TABLE 1C

Antitumor, Antibacterial, and Antifungal Data on
2,5,9-Trisubstituted 2H—[1]benzopyrano[4,3,2-cd]indazoles

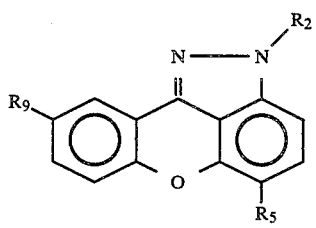

| $R_9$ | $R_2$ | $R_5$ | L1210 in vitro $ID_{50}$ (M) | P388 in vivo Dose (mg/kg) | P388 in vivo T/C × 100 | ABMF Minimal Inhibitory Concentration (μ/ml) E. coli | S. typh. | Coryn. sp. | S. pneum. | R. aurant. |
|---|---|---|---|---|---|---|---|---|---|---|
| $CH_3O$ | $CH_2CH_2NEt_2$ | $NO_2$ | $9.2 \times 10^{-7}$ | 100 | 192 | <0.46 | 111.0 | <0.46 | <0.46 | 111.0 |
|  |  |  |  | 50 | 148 |  |  |  |  |  |
|  |  |  |  | 25 | 126 |  |  |  |  |  |
| $CH_3O$ | $CH_2CH_2NEt_2$ | $NHCH_2CH_2NH_2$ | $1.1 \times 10^{-6}$ | 25 | 145 | 111.0 | 111.0 | 4.1 | 12.3 | 333.0 |
|  |  |  |  | 12.5 | 154 |  |  |  |  |  |
| $CH_3O$ | $CH_2CH_2CH_2NMe_2$ | $NO_2$ | $5.8 \times 10^{-7}$ | 200 | 218 | 4.1 | 111.0 | <0.46 | <0.46 | 1000 |
|  |  |  |  | 100 | 159 |  |  |  |  |  |
|  |  |  |  | 50 | 134 |  |  |  |  |  |

TABLE 1C-continued
Antitumor, Antibacterial, and Antifungal Data on 2,5,9-Trisubstituted 2H—[1]benzopyrano[4,3,2-cd]indazoles

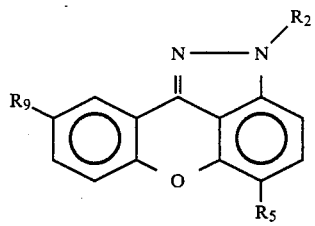

| R9 | R2 | R5 | L1210 in vitro ID$_{50}$ (M) | P388 in vivo Dose (mg/kg) | T/C × 100 | ABMF Minimal Inhibitory Concentration (μ/ml) E. coli | S. typh. | Coryn. sp. | S. pneum. | R. aurant. |
|---|---|---|---|---|---|---|---|---|---|---|
| CH$_3$O | CH$_2$CH$_2$N(CH$_2$)$_4$ | NO$_2$ | 2.0 × 10$^{-6}$ | | | >1000 | 37.0 | <0.46 | <0.46 | 111.0 |
| CH$_3$O | CH$_2$CH$_2$N(CH$_2$)$_4$ | NH$_2$ | 3.6 × 10$^{-7}$ | | | 12.3 | 111.0 | 4.1 | 4.1 | 333 |
| HO | CH$_2$CH$_2$N(CH$_2$)$_4$ | NO$_2$ | 3.5 × 10$^{-9}$ | | | >1000 | 1.4 | <0.46 | <0.46 | 1000 |
| HO | CH$_2$CH$_2$CH$_2$NMe$_2$ | NO$_2$ | 1.5 × 10$^{-8}$ | 25 / 12.5 / 6.25 | 226 / 200 / 150 | <0.46 | 12.3 | <0.46 | <0.46 | 1000 |
| HO | CH$_2$CH$_2$NEt$_2$ | NH$_2$ | 7.1 × 10$^{-8}$ | 25 / 12.5 / 6.25 | 192 / 201 / 167 | 111.0 | 111.0 | 12.3 | 12.3 | >1000 |
| HO | CH$_2$CH$_2$NEt$_2$ | NHC(O)CH$_2$NHCH$_2$CH$_2$OH | 5.7 × 10$^{-9}$ | 100 / 50 / 25 | 272 / 227 / 198 | 111.0 | >1000 | 333.0 | 333.0 | >1000 |
| HO | CH$_2$CH$_2$NEt$_2$ | NHCH$_2$CH$_2$NHCH$_2$CH$_2$OH | 4.8 × 10$^{-8}$ | 12.5 / 6.25 | 272 / 236 | 11.0 | >33.0 | 33.0 | 11.0 | >33.0 |
| HO | CH$_2$CH$_2$NHCH$_2$CH$_2$OH | NO$_2$ | 1.5 × 10$^{-8}$ | 50 / 25 / 12.5 | 230 / 218 / 190 | <0.46 | 12.3 | 1.4 | 1.4 | 1000 |
| HO | CH$_2$CH$_2$NHCH$_2$CH$_2$OH | NH$_2$ | 1.2 × 10$^{-7}$ | 25 / 12.5 / 6.25 | 260 / 200 / 165 | 4.1 | 37.0 | 12.3 | 37.0 | >1000 |
| HO | CH$_2$CH$_2$NHCH$_2$CH$_2$OH | NHC(O)CH$_2$NHCH$_2$CH$_2$OH | 1.7 × 10$^{-6}$ | 240 / 120 / 60 | 184 / 142 / 134 | 1000 | >1000 | 333.0 | >1000 | 1000 |
| HO | CH$_2$CH$_2$NHCH$_2$CH$_2$OH | NHCH$_2$CH$_2$NHCH$_2$CH$_2$OH | 1.3 × 10$^{-7}$ | 25 / 12.5 / 6.25 | 236 / 236 / 173 | 111.0 | 1000 | 37.0 | 333.0 | >1000 |

TABLE 2

Chemical, Antitumor, Antibacterial, and Antifungal Data on 2,5-(Disubstituted)-2H[1]benzothiopyrano[4,3,2-cd]indazoles

| $R_2$ | $R_5$ | $R_7$–$R_{10}$ | Formula | mp, °C. | L1210 in vitro $ID_{50}$ (M) | HCA-3 in vitro $ID_{50}$ (M) | Dose (mg/kg) | P388 in vivo T/C × 100 | A. Aerogenes | E. Coli | B. Subtilis | S. Faecalis | P. Avellaneum |
|---|---|---|---|---|---|---|---|---|---|---|---|---|---|
| $CH_2CH_2N(C_2H_5)_2$ | $NO_2$ | | $C_{19}H_{20}N_4O_2S$ | 150-152 | $5.6 \times 10^{-8}$ | $2.0 \times 10^{-7}$ | 50.00 / 25.00 | 170 / 138 | 0 (3) | 14 (1) | 14 (3) | 14 (3) | 15 (3) |
| $CH_2CH_2N(C_2H_5)_2$ | $NH_2$ | | $C_{19}H_{22}N_4S$ | 100-102 | $1.3 \times 10^{-7}$ | $1.1 \times 10^{-6}$ | 25.00 / 12.50 | 162 / 144 | 0 (3) | 0 (3) | 0 (3) | 14 (1) | 14 (1) |
| $CH_2CH_2N(C_2H_5)_2$ | $NHCOCH_3$ | | $C_{21}H_{24}N_4OS$ .HCl.$1H_2O$ | 208-211 | $2.4 \times 10^{-7}$ | $6.0 \times 10^{-6}$ | 12.50 | 170 | 16 (3) | 16 (3) | 16 (.5) | 15 (3) | 0 (3) |
| $CH_2CH_2N(C_2H_5)_2$ | $N=CHN(CH_3)_2$ | | $C_{22}H_{27}N_5S$ | 108-109 | $1.0 \times 10^{-7}$ | $2.4 \times 10^{-7}$ | 50.00 / 25.00 | 206 / 145 | 0 (3) | 0 (3) | 16 (1) | 0 (3) | 16 (3) |
| $CH_2CH_2N(C_2H_5)_2$ | $NHCH_2CH_2N(C_2H_5)_2$ | | $C_{25}H_{35}N_5S$ .2HCl | 234-236 | $1.4 \times 10^{-7}$ | $4.5 \times 10^{-7}$ | 25.00 | 155 | 14 (.5) | 18 (.1) | 15 (.1) | 15 (3) | 17 (3) |
| $CH_2CH_2NHCH_2CH_2OH$ | $NO_2$ | | $C_{17}H_{16}N_4O_3S$.HCl | 293-295 dec | $2.0 \times 10^{-8}$ | $1.0 \times 10^{-7}$ | 25.00 / 12.50 / 6.25 | 197 / 150 / 148 | 16 (.1) | 16 (.1) | 18 (.5) | 15 (3) | 0 (3) |
| $CH_2CH_2NHCH_2CH_2OH$ | $NH_2$ | | $C_{17}H_{18}N_4OS$ .1.6HCl.$0.2H_2O$ | 285 dec | $1.7 \times 10^{-7}$ | $5.8 \times 10^{-7}$ | 25.00 / 12.50 / 6.25 / 3.12 | 194 / 159 / 143 / 135 | 16 (.5) | 17 (.5) | 18 (.5) | 20 (1) | 15 (3) |
| $CH_2CH_2N(C_2H_5)_2$ | $CH_2CH_2N$〈pyrrolidinone ring〉 | | $C_{24}H_{29}N_5O_2S$ .$0.2H_2O$ | 90-94 | $9.5 \times 10^{-7}$ | $1.8 \times 10^{-6}$ | 100.00 / 84.38 / 63.28 / 50.00 / 47.45 | 218 / 193 / 165 / 140 / 141 | 0 (3) | 0 (3) | 14 (3) | 14 (.5) | 0 (3) |
| $CH_2CH_2NHCH_2CH_2OH$ | $NHCH_2CH_2NHCH_2CH_2OH$ | | $C_{23}H_{31}N_5OS$ .2.7HCl.$0.7H_2O$ | 223-228 | $8.2 \times 10^{-8}$ | $2.0 \times 10^{-7}$ | 12.50 / 6.25 / 3.12 | 280 Cures / 219 / 209 Cures | 15 (.1) | 26 (.5) | 18 (.5) | 16 (.5) | 0 (3) |
| $CH_2CH_2NHCH_2CH_2OH$ | $NHCH_2CH_2N(C_2H_5)_2$ | | $C_{23}H_{31}N_5OS$ .2.9HCl.$1.9H_2O$ | 208-212 | $2.4 \times 10^{-7}$ | $4.5 \times 10^{-7}$ | 25.00 / 12.50 / 6.25 / 3.12 | 147 / 135 / 137 / 134 | — | — | — | — | — |
| $CH_2CH_2NHCH_2CH_2OH$ | $NHCH_2CH_2NHCH_2CH_2OH$ | | $C_{21}H_{27}N_5O_2S$ .2.9HCl.$0.5H_2O$ | 222-225 | $4.0 \times 10^{-7}$ | $4.8 \times 10^{-7}$ | 12.50 / 12.00 / 6.25 / 6.00 / 3.12 / 3.00 / 1.56 | 271 Cures / 270 Cures / 195 Cures / 218 / 176 / 187 / 180 | 14 (.5) | 14 (.5) | 15 (.5) | 0 (3) | 0 (3) |

TABLE 2-continued

Chemical, Antitumor, Antibacterial, and Antifungal Data on 2,5-(Disubstituted)-2H[1]benzothiopyrano[4,3,2-cd]indazoles

| $R_2$ | $R_5$ | $R_7$–$R_{10}$ | Formula | mp, °C. | L1210 in vitro $ID_{50}$ (M) | HCA-3 in vitro $ID_{50}$ (M) | P388 in vivo Dose (mg/kg) | P388 in vivo T/C × 100 | A. Aerogenes | E. Coli | B. Subtilis | S. Faecalis | P. Avellaneum |
|---|---|---|---|---|---|---|---|---|---|---|---|---|---|
| $CH_2CH_2NHCH_2CH_2OH$ | 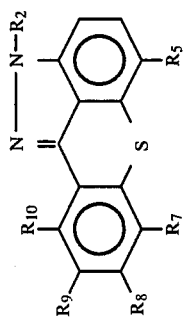 | | $C_{22}H_{25}N_5O_3S$ .HCl.0.5$H_2O$ | 180–182 | $5.7 \times 10^{-7}$ | $1.4 \times 10^{-6}$ | 1.50<br>0.78<br>0.75 | 155<br>153<br>146 | — | — | — | — | — |
| $CH_2CH_2N(CH_3)_2$ | $NO_2$ | | $C_{17}H_{16}N_4O_2S$ .$CH_3SO_3H$ | 266 dec | $7.9 \times 10^{-8}$ | $9.7 \times 10^{-8}$ | 12.50 | 158 | 14 (1) | 15 (.1) | 16 (1) | 17 (1) | 0 (3) |
| $CH_2CH_2CH_2N(CH_3)_2$ | $NO_2$ | | $C_{18}H_{18}N_4O_2S$ .HCl.0.3$H_2O$ | 309 dec | $1.9 \times 10^{-7}$ | $2.1 \times 10^{-7}$ | 100.00<br>50.00<br>25.00<br>50.00<br>25.00 | 143<br>135<br>174<br>121<br>153<br>126 | 15 (1) | 14 (.1) | 15 (3) | 15 (3) | 15 (.1) |
| $CH_2CH_2N(CH_3)_2$ | $NH_2$ | | $C_{17}H_{18}N_4S$ .2HCl.1.1$H_2O$ | 273 dec | $8.0 \times 10^{-8}$ | $2.8 \times 10^{-7}$ | 12.50<br>6.25 | 160<br>126 | 14 (.1) | 16 (.5) | 15 (.5) | 20 (1) | 17 (.5) |
| $CH_2CH_2CH_2N(CH_3)_2$ | $NH_2$ | | $C_{18}N_{20}N_4S$ .2HCl.1.1$H_2O$ | 264 dec | $2.0 \times 10^{-6}$ | $1.8 \times 10^{-6}$ | 200.00<br>100.00<br>100.00<br>50.00 | 169<br>182<br>121<br>197<br>129 | 16 (.5) | 15 (3) | 0 (3) | 15 (3) | 16 (3) |
| $CH_2CH_2NH_2$<br>$CH_2CH_2NH_2$ | $NO_2$<br>$NO_2$ | | $C_{15}H_{12}N_4O_2S$<br>$C_{15}H_{12}N_4O_2S$ .HCl.0.4$H_2O$ | 199–203<br>>300 | | $2.0 \times 10^{-7}$<br>— | —<br>25.00<br>12.50 | 187<br>136 | 18 (.1) | 15 (.1) | 17 (.1) | 0 (3) | 0 (3) |
| $CH_2CH_2N(C_2H_5)_2$ | $NHCOCH_2Cl$ | | $C_{21}H_{23}ClN_4OS$ | 204 dec | $1.9 \times 10^{-7}$ | $3.8 \times 10^{-7}$ | 50.00<br>25.00 | 165<br>124 | | | | | |
| $CH_2CH_2NH_2$ | $NH_2$ | | $C_{15}H_{14}N_4S$.2HCl | >300 | $1.1 \times 10^{-7}$ | $3.2 \times 10^{-7}$ | 12.50<br>6.25<br>3.12 | 160<br>133<br>125 | 17 (.1) | 19 (.5) | 18 (1) | 15 (1) | 14 (3) |
| $CH_2CH_2N(C_2H_5)_2$ | $NHCH_2CH_2NH_2$ | | $C_{21}H_{27}N_5S$.3HBr | 263 dec | $4.6 \times 10^{-8}$ | $9.7 \times 10^{-8}$ | 25.00<br>12.50<br>6.25<br>3.12 | 148 Cures<br>297 Cures<br>215<br>178 | 19 (.5) | 0 (3) | 20 (.5) | 15 (1) | 0 (3) |

TABLE 2-continued

Chemical, Antitumor, Antibacterial, and Antifungal Data on 2,5-(Disubstituted)-2H[1]benzothiopyrano[4,3,2-cd]indazoles

| $R_2$ | $R_5$ | $R_7$–$R_{10}$ | Formula | mp. °C. | L1210 in vitro $ID_{50}$ (M) | HCA-3 in vitro $ID_{50}$ (M) | Dose (mg/kg) | P388 in vivo T/C × 100 | A. Aerogenes | E. Coli | B. Subtilis | S. Faecalis | P. Avellaneum |
|---|---|---|---|---|---|---|---|---|---|---|---|---|---|
| $CH_2CH_2N(C_2H_5)_2$ | $NHCH_2CH_2NHCH_2CH_2OH$ | | $C_{19}H_{23}N_5OS.3HCl$ | 264 dec | $2.4 \times 10^{-8}$ | $8.8 \times 10^{-8}$ | 25.00 | 169 | 15 (.5) | 0 (3) | 15 (.5) | 0 (3) | 0 (3) |
| $CH_2CH_2N(C_2H_5)_2$ | $NHCH_2CH_2NH_2$ | | $C_{22}H_{29}N_5S.3HCl.2.1H_2O$ | 222 dec | $2.9 \times 10^{-7}$ | $8.8 \times 10^{-7}$ | 12.50 | 154 | | | | | |
| | | | | | | | 6.25 | 142 | | | | | |
| | | | | | | | 3.12 | 132 | | | | | |
| $CH_2CH_2NHCH_2H_5$ | $NO_2$ | | $C_{17}H_{16}N_4O_2S.HCl$ | | $2.4 \times 10^{-8}$ | $1.4 \times 10^{-7}$ | 12.5 | 187 | | | | | |
| $CH_2CH_2NHCH_2H_5$ | $NH_2$ | | $C_{17}H_{18}N_4S.2HCl$ | | $7.1 \times 10^{-8}$ | $3.0 \times 10^{-7}$ | 12.5 | 188 | | | | | |
| $(CH_2)_3N(CH_3)_2$ | $NHCH_2CH_2NH_2$ | | $C_{20}H_{25}N_5S.3HCl$ | | $2.9 \times 10^{-8}$ | $1.3 \times 10^{-7}$ | 12.5 | 298 | | | | | |
| | | | | | | | 6.25 | 185 | | | | | |
| $CH_2CH_2N(C_2H_5)_2$ | $NO_2$ | 7-OCH$_3$, 10-OH | $C_{20}H_{22}N_4O_4S.HCl$ | 267–270 | $1.0 \times 10^{-6}$ | $4.2 \times 10^{-7}$ | | | | | | | |
| $CH_2CH_2N(C_2H_5)_2$ | $NO_2$ | 7,10-(OCH$_3$)$_2$ | $C_{21}H_{24}N_4O_4S.0.1C_3H_7NO$ | 188–190 | $1.3 \times 10^{-6}$ | $5.0 \times 10^{-7}$ | | | | | | | |
| $CH_2CH_2N(C_2H_5)_2$ | $NO_2$ | 7,10-(OH)$_2$ | $C_{19}H_{20}N_4O_4S.HBr.0.2H_2O$ | 283 dec | $1.7 \times 10^{-6}$ | | | | | | | | |
| $CH_2CH_2N(C_2H_5)_2$ | $NH_2$ | 7,10-(OH)$_2$ | $C_{19}H_{22}N_4O_2S.HBr$ | 229–223 | $>2.2 \times 10^{-6}$ | $>2.2 \times 10^{6}$ | 50.00 | 138 | 0 (3) | 0 (3) | 0 (3) | 19 (3) | 0 |
| $CH_2CH_2N(C_2H_5)_2$ | $NHCH_2CH_2NHCH_2CH_2OH$ | 7,10-(OH)$_2$ | $C_{23}H_{31}N_5O_3S.2.4HBr.0.4H_2O$ | 243–245 | $>1.5 \times 10^{-6}$ | $>1.5 \times 10^{6}$ | 25.00 | 121 | 14 (3) | 0 (3) | 0 (3) | 15 (.5) | 0 |
| | | | | | | | 12.50 | 118 | | | | | |
| | | | | | | | 6.25 | 123 | | | | | |
| $CH_2CH_2NHCH_2CH_2OH$ | $NO_2$ | | $C_{20}H_{22}N_4O_3S$ | | $6.4 \times 10^{-7}$ | | | 25.00 | 209 | | | | |
| $CH_2CH_2NHCH_2CH_2OH$ | $NH_2$ | 9-OCH$_3$ | $.CH_3SO_3H$ $C_{20}H_{24}N_4OS.2HCl$ | 275 dec | | $1.6 \times 10^{-6}$ | 12.50 | 142 | 154 | | | | |
| | | | | | | | | 50.00 | | | | | |
| $CH_2CH_2N(C_2H_5)_2$ | NHCH$_2$CH$_2$N (pyrrolidinone) | 9-OCH$_3$ | $C_{25}H_{31}N_5O_3S$ 2HCl | | | $1.0 \times 10^{-6}$ | 100.00 | 220 | — | — | — | — | — |
| $CH_2CH_2N(C_2H_5)_2$ | $NH_2$ | 9-OH | $C_{19}H_{22}N_4OS.2HCl$ | | $1.2 \times 10^{-8}$ | $2.8 \times 10^{-8}$ | 6.25 | 238 | — | — | — | — | — |
| $CH_2CH_2N(C_2H_5)_2$ | $NHCH_2CH_2NHCH_2CH_2OH$ | 9-OCH$_3$ | $C_{24}H_{33}N_5O_2S3HCl$ | | $2.0 \times 10^{-7}$ | $2.3 \times 10^{-7}$ | 25.00 | 177 | — | — | — | — | — |
| $CH_2CH_2N(C_2H_5)_2$ | $NHCH_2CH_2NH_2$ | 9-OCH$_3$ | $C_{22}H_{29}N_5OS.3HCl$ | | $2.1 \times 10^{-7}$ | $2.9 \times 10^{-7}$ | 12.5 | 177 | — | — | — | — | — |

TABLE 2-continued

Chemical, Antitumor, Antibacterial, and Antifungal Data on 2,5-(Disubstituted)-2H[1]benzothiopyrano[4,3,2-cd]indazoles

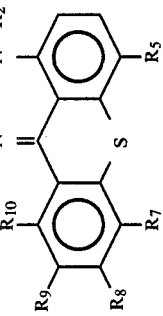

| R$_2$ | R$_5$ | R$_7$–R$_{10}$ | Formula | mp, °C. | L1210 in vitro ID$_{50}$ (M) | HCA-3 in vitro ID$_{50}$ (M) | P388 in vivo Dose (mg/kg) | P388 in vivo T/C × 100 | ABF Zone Diameter (Conc. in mg/ml) A. Aerogenes | E. Coli | B. Subtilis | S. Faecalis | P. Avellaneum |
|---|---|---|---|---|---|---|---|---|---|---|---|---|---|
| CH$_2$CH$_2$N(C$_2$H$_5$)$_2$ | NHCH$_2$CH$_2$N (pyrrolidinone) | 9-OH | C$_{24}$H$_{29}$N$_5$O$_3$S·2HCl | | 5.5 × 10$^{-9}$ | 2.4 × 10$^{-8}$ | 12.5 | 175 | — | — | — | — | — |

TABLE 3

Chemical, Antitumor, Antibacterial, and Antifungal Data on 2,5-(Disubstituted)-2H—[1]benzoselenino[4,3,2-cd]indazoles

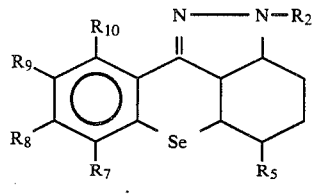

| $R_2$ | $R_5$ | $R_7$-$R_{10}$ | Formula | mp °C. | L1210 in vitro $ID_{50}$ (M) | P388 in vivo Dose (mg/kg) | $T/C \times 100$ | S. Typhimurium | E. Coli | S. Pneumoniae | S. Faecalis | B. Catarrhalis |
|---|---|---|---|---|---|---|---|---|---|---|---|---|
| $CH_2CH_2NEt_2$ | $NHCH_2CH_2CH_2NH_2$ | H | $C_{22}H_{29}N_5Se$ . 2.9 HBr. 1.9 $H_2O$ | 255–256 | $1.6 \times 10^{-7}$ | | | 37.0 | 111.0 | 4.1 | 111.0 | 37.0 |
| $CH_2CH_2N$ | $NHCH_2CH_2NH_2$ | H | $C_{21}H_{25}N_5Se$ . 2.7 HCl. 0.6 $H_2O$ | 265–272 dec | | | | | | | | |
| $CH_2CH_2NEt_2$ | $NHCH_2CH_2NH_2$ | 9-OH | $C_{21}H_{27}N_5O_{23}$ 3.0 HCl. 0.3 $H_2O$ | >260 dec | $2.4 \times 10^{-9}$ | 3.12 | 198 | 37.0 | 1.4 | 4.1 | 37.0 | 4.0 |
| $CH_2CH_2NEt_2$ | $NO_2$ | H | $C_{19}H_{20}N_4O_2Se$ . 0.9 HCl. 0.4 $H_2O$ | 273–274 dec | $1.4 \times 10^{-7}$ | | | | | | | |
| $CH_2CH_2NEt_2$ | $NO_2$ | 9-OH | $C_{19}H_{20}N_4O_3Se$ 0.5 HCl. 0.7 $H_2O$ | 247–249 dec | $4.1 \times 10^{-9}$ | | | | | | | |
| $CH_2CH_2NEt_2$ | $NO_2$ | 8-OH | $C_{19}H_{20}N_4O_3Se$ 1.0 HCl | 248–252 dec | | | | | | | | |
| $CH_2CH_2NEt_2$ | $NH_2$ | H | $C_{19}H_{22}N_4Se$ 2.0 HCl | | $1.3 \times 10^{-7}$ | | | 111.0 | 37.0 | 12.3 | 37.0 | 12.3 |
| $CH_2CH_2N$ | $NH_2$ | H | | | | | | | | | | |
| $CH_2CH_2NEt_2$ | $NHCH_2CH_2NH_2$ | H | $C_{21}H_{27}N_5Se$ . 2.8 HCl. 1.4 $H_2O$ | 255–158 dec | $3.3 \times 10^{-8}$ | 12.50 6.25 | 270 (cures) 205 | 12.3 | 12.3 | 4.1 | 12.3 | 12.3 |
| $CH_2CH_2NEt_2$ | $NHCH_2CH_2NEt_2$ | H | $C_{25}H_{35}N_5Se$ . 2.0 HBr. 0.2 $H_2O$ | 243–244 | $2.5 \times 10^{-7}$ | 50.0 25.0 | 174 127 | | | | | |

PREPARATION OF PHARMACEUTICAL COMPOSITIONS

When being utilized as antibiotic and antifungal agents, the compounds of the invention can be prepared and administered in a wide variety of topical, oral, and parenteral dosage forms. It will be clear to those skilled in the art that the following dosage forms may comprise as the active component, one or more compounds of formula 1, a corresponding pharmaceutically acceptable salt of any of said compounds, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Topical preparations include creams, lotions, gels, and sprays. These various topical preparations may be formulated by well-known procedures. See, for example, Remington's Pharmaceutical Sciences, Chapter 43, 14th Ed., 1970, Mack Publishing Co., Easton, Pa. 18042, USA.

Preferably, the pharmaceutical preparation is in unit dosage form. In such form, the preparation is subdivided into unit doses containing appropriate quantities of the active component. The unit dosage form can be packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 50 mg to 500 mg according to the particular application and the potency of the active ingredient.

In therapeutic use as antibiotic and antifungal agents, the compounds utilized in the pharmaceutical method of this invention are administered at the initial dosage of about 0.1 mg to about 50 mg per kilogram. A dose range of about 0.5 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like, N,N-dimethylacetamide, suitable mixtures thereof and vegetable oils. The proper fluidity can be maintained, for example, by the used of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredients plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage. Unit dosage form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel unit dosage forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in unit dosage form as hereinbefore disclosed. A unit dosage form can, for example, contain the principal active compound in amounts ranging from about 0.1 to about 500 mg, with from about 0.5 to about 250 mg being preferred. Expressed in proportions, the active compound is generally present in from about 0.1 to about 500 mg/ml of carrier. In the case of compositions containing supplementary active ingredients, the dosages are determined by reference to the usual dose and the manner of administration of the said ingredients. The daily parenteral doses for mammalian subjects to be treated ranges from 0.1 mg/kg to 100 mg/kg. The preferred daily dosage range is 0.3 mg/kg to 10 mg/kg.

The invention and the best mode of practicing the same are illustrated by the following examples of preferred embodiments of selected compounds and their preparation.

EXAMPLE 1

N,N-Diethyl-5-nitro-2H[1]benzopyrano[4,3,2-cd]-indazole-2-ethanamine

A solution of 0.83 g of crude 1-chloro-4-nitro-9H-xanthen-9-one and 1.0 g of [2-(diethylamino)ethyl]-hydrazine in 15 ml of tetrahydrofuran was stirred at room temperature for four hours. The mixture was evaporated to dryness and the residue was triturated with water, collected, and recrystallized from ethyl acetate to provide the product mp 158°–160° C. The methanesulfonic acid salt mp 179°–180° C. crystallized from a solution of the base in a mixture of methanol and diethylether containing an equivalent of methanesulfonic acid.

The 1-chloro-4-nitro-9H-xanthen-9-one was prepared as follows: Crude 2-(5'-chloro-2-nitrophenoxy)-benzoic acid (50 g) was added to 200 g of concentrated sulfuric acid. The mixture was held at 75° C. for 4.5 hours, and added to a stirred mixture of 1.5 l of chloroform and water containing ice as needed to maintain the temperature below 35° C. The chloroform layer was separated, washed with 5% sodium bicarbonate, evaporated to dryness and the residue was crystallized from 200 ml of toluene and 30 ml of cyclohexane to provide the product mp 175°–186° C.

The 2-(5'-chloro-2-nitrophenoxy)benzoic acid was prepared as follows: Crude 2-(5-chloro-2-nitrophenoxy)benzaldehyde was heated under reflux with 200 ml of diethylether, 120 ml of water, 41.1 g of $Na_2Cr_2O_7 \cdot 2H_2O$ and 6.0 g of a 40% tetra-n-butylammonium hydroxide solution, and to it was added 63 ml of 9M $H_2SO_4$ over three hours. Heating was continued for an additional two hours, and the aqueous layer was extracted with ether and evaporated to dryness to provide the product.

The 2-(5-chloro-2-nitrophenoxy)benzaldehyde was prepared as follows: To 16.2 g of 2,4-dichloronitrobenzene stirred at 170° was added 7.1 g of the potassium salt of salicylaldehyde, monohydrate, in portions over 1.5 hours. The mixture was stirred at 170° C. for two hours, triturated with 150 ml of $CH_2Cl_2$ and filtered. The filtrate was evaporated to a red oil and the excess dichloronitrobenzene was removed by steam distillation to leave the product.

EXAMPLE 2

2-[[2-(5-Nitro-2H-[1]benzopyrano[4,3,2-cd]-indazol-2-yl)ethyl]amino]ethanol, monohydrochloride A suspension of 2.76 g of 1-chloro-4-nitro-9H-xanthen-9-one, 30 ml of THF, 15 ml of methanol and 1.40 g of 2-[(hydrazinoethyl)amino]-ethanol was stirred at room temperature for three days. The precipitate was collected, washed with THF and dried, providing the title compound, mp 262°–64° C. (decomp.).

EXAMPLE 3

5-Amino-N,N-diethyl-2H-[1]benzopyrano[4,3,2-cd]-indazol-2-ethanamine

A solution of 8.9 g (0.026 mole) of N,N-diethyl-5-nitro-2H-[1]benzopyrano[4,3,2-cd]indazole-2-ethanamine in 100 ml of tetrahydrofuran was hydrogenated over 1 g of 10% palladium on carbon at ambient temperature and a hydrogen pressure of 46.3–52.3 psi. The mixture was filtered and the solvent removed in vacuo. The oily residue was triturated with petroleum ether and recrystallized from n-hexane to give the product, mp 78°–80° C.

EXAMPLE 4

N-[2-[2-(Diethylamino)ethyl]-2H-[1]benzopyrano-[4,3,2-cd]indazol-5-yl]ethanediamine, trihydrobromide, dihydrate A solution of 2.47 g of N,N-diethyl-5-nitro-2H-[1]benzopyrano[4,3,2-cd]indazole-2-ethanamine in 45 ml of THF was hydrogenated in the presence of 10% palladium on carbon hydrogenation catalyst to 5-amino-N,N-diethyl-2H-[1]benzopyrano[4,3,2-cd]indazol-2-ethamine. The catalyst was removed, the solvent replaced with 35 ml of absolute ethanol, 4.4 g of 2-bromoethylamine hydrobromide added, and the mixture heated three days under reflux. The mixture was filtered, evaporated to dryness, and the residue crystallized from ethanol, providing the title compound, mp 235°–48° C. (decomp.).

EXAMPLE 5

N,N-Diethyl-9-methoxy-5-nitro-2H-[1]benzopyrano-[4,3,2-cd]indazole-2-ethanamine, methanesulfonate (1:1)

A mixture of 25 g of 1-chloro-7-methoxy-4-nitro-9H-xanthen-9-one, and 21.48 g of [2-(diethylamino)-ethyl]hydrazine in 500 ml DMF was stirred at room temperature for 45 minutes. The mixture was evaporated to dryness, and the residue was triturated with isopropyl alcohol and the yellow crystals collected at the title compound free base, mp 162°–165° C.

The title salt, mp 227°–229° C., crystallized from a methanol solution of the base and an equivalent of methanesulfonic acid.

EXAMPLE 6

1-[2-[2-(Diethylamino)ethyl]-9-methoxy-2H-[1]benzopyrano[4,3,2,-cd]indazol-5-yl]-1,2-ethanediamine, trihydrobromide A mixture of 5 g of N,N-diethyl-9-methoxy-5-nitro-2H-[1]-benzopyrano[4,3,2-cd]indazole-2-ethanamine, and 0.940 g of 10% palladium on carbon, in 250 ml of tetrahydrofuran was stirred under hydrogen atmosphere for 18 hours, filtered, and the filtrate concentrated to give 5-amino-N,N-diethyl-9-methoxy-2H-[1]benzopyrano[4,3,2-cd]indazole-2-ethanamine.

A mixture of 4.9 g of 5-amino-N,N-diethyl-9-methoxy-2H-[1]benzopyrano[4,3,2,-cd]indazole-2-ethanamine and 8.7 g of bromoethylamine hydrobromide in 150 ml of ethyl alcohol was heated under reflux for 100 hours, cooled to room temperature and filtered affording the title compound, mp 272°–275° C.

EXAMPLE 7

9-Methoxy-N,N-dimethyl-5-nitro-2H-[1]benzopyrano[4,3,2-cd]indazole-2-propanamine, methanesulfonate (1:1.17)

A mixture of 2 g of 1-chloro-7-methoxy-4-nitro-9H-xanthen-9-one and 1.53 g of [3-(dimethylamino)-propyl]hydrazine in 40 ml of D.M.F. was stirred at room temperature for 16 hours, and then evaporated to dryness. The residue was triturated with isopropyl alcohol, and the yellow solid collected as the title compound free base.

The title salt, mp 119°–121° C., crystallized from a methanol solution of the base and 1.25 equivalents of methanesulfonic acid.

EXAMPLE 8

9-Methoxy-5-nitro-2-[2-(1-pyrrolidinyl)ethyl]-2H-[1]-benzopyrano[4,3,2-cd]indazole, monohydrochloride A mixture of 12.2 g of 1-chloro-7-methoxy-4-nitro-9H-xanthen-9-one and 11.0 g of 1-(2-hydrazinoethyl)-pyrrolidine in 200 ml of THF was stirred 20 hours at room temperature. The orange liquor was decanted, freed of solvent under reduced pressure, and the residue, in chloroform, was chromatographed over silica gel, eluting with chloroform-methanol (25:1 by volume). The desired fractions yielded the free base of the title compound, mp 140°–142° C.

The hydrochloride salt, mp 251°–254° C. (decomp.) crystallized from a solution of the base in aqueous methanolic hydrochloric acid upon addition of ethyl acetate.

EXAMPLE 9

9-Methoxy-2-[2-(1-pyrrolidinyl)ethyl]-2H-[1]benzopyrano[4,3,2,-cd]indazol-5-amine, monohydrochloride In 50 ml of THF 3.8 g of 9-methoxy-5-nitro-2-[2-(1-pyrrolidinyl)ethyl]-2H-[1]benzopyrano[4,3,2-cd]-indazole was hydrogenated at atmospheric pressure and room temperature in the presence of 1.0 g of 10% palladium on carbon hydrogenation catalyst over a period of four hours. The mixture was filtered, the filtrate freed of solvent under reduced pressure and the residue converted to the title salt, mp 218°–221° C. (decomp.) in ethyl acetate containing an equivalent of 1N methanolic hydrogen chloride.

EXAMPLE 10

5-Nitro-2[2-(1-pyrrolidinyl)ethyl]-2H-[1]benzopyrano[4,3,2-cd]-indazol-9-ol, methansulfonate A solution of 10 g of 1-chloro-7-hydroxy-4-nitro-9H-xanthen-9-one and 9 g of 1-(2-hydrazinoethyl)pyrrolidine in 200 ml of N,N-dimethylformamide was stirred 18 h at room temperature and then the solvent was removed in vacuo. The residue was triturated in 450 ml of 2-propanol to provide 10.32 g of the free base, mp 225°–229° C. A slurry of 2.5 g of the base in 100 ml of methanol was treated with 0.5 ml of methanesulfonic acid. After a few drops of water was added to effect solution, the mixture was filtered over Celite and the filtrate was diluted with 100 ml of ethyl acetate. Upon concentrating the volume in vacuo to 100 ml, yellow crystals formed which were collected by filtration and washed with ethanol to provide the title salt, mp 251°–252° C.

EXAMPLE 11

9-Hydroxy-N,N-dimethyl-5-nitro-2H-[1]benzopyrano[4,3,2-cd]indazole-2-propanamine, methanesulfonate (1:1)

A mixture of 2 g of 1-chloro-7-hydroxy-4-nitro-9H-xanthen-9-one and 1.61 g of [3-(dimethylamino)-propyl]hydrazine in 40 ml of D.M.F. was stirred for ten minutes at room temperature and then evaporated to dryness. The solid residue was triturated with isopropyl alcohol, and the yellow crystals collected to afford the title compound as the free base.

The title salt, mp 269°–272° C. (decomp.), crystallized from a methanol solution of the base and an equivalent of methanesulfonic acid.

EXAMPLE 12

5-Amino-N,N-diethyl-9-hydroxy-2H-[1]benzopyrano-[4,3,2-cd]indazole-2-ethanamine, dihydrochloride A mixture of 1.25 g of 1-chloro-7-hydroxy-4-nitro-9H-xanthen-9-one, and 1.12 g of [2-(diethylamino)ethyl]hydrazine in 25 ml of DMF was stirred at room temperature for 45 minutes, and then evaporated to dryness. The residue was triturated with isopropyl alcohol providing yellow crystals of N,N-diethyl-9-hydroxy-5-nitro-2H-[1]benzopyrano-[4,3,2-cd]indazole-2-ethanamine.

A mixture of N,N-diethyl-9-hydroxy-5-nitro-2H-[1]benzopyrano[4,3,2-cd]indazole-2-ethanamine, and 450 mg of 20% palladium on carbon, in 250 ml of tetrahydrofuran was stirred under a hydrogen atmosphere for 18 hours, filtered, and the filtrate concentrated in vacuo to give the title compound as the free base.

The title salt, crystallized from a 2-propanol solution of the base and two equivalents of hydrochloric acid, mp >300° C.

EXAMPLE 13

N-[2-[2-(Diethylamino)ethyl]-9-hydroxy-2H-[1]benzopyrano[4,3,2-cd]indazole-5-yl]-2-[(2-hydroxyethyl)-amino]-acetamide, hydrochloride To a solution of 0.46 g of 2-[2-(diethylamino)-ethyl]-5-amino-2H-[1]benzopyrano[4,3,2-cd]indazol-9-ol in 25 ml N,N-dimethylformamide was added 0.31 g of N'-(ethyl carbonimidoyl)-N,N-dimethyl-1,3-propanediamine monohydrochloride, and 1.03 g of N-[2-(phenylmethoxy)ethyl]-N-(phenylmethyl)glycine.

After 1.5 hours, the reaction was poured into 20 ml of aqueous saturated sodium bicarbonate solution and extracted with dichloromethane. The extracts were dried and concentrated in vacuo. The resulting solid was chromatographed on silica gel with a solution of 5% methanol in dichloromethane as eluent to afford N-[2-[2-(diethylamino)ethyl]-9-hydroxy-2H-[1]benzopyrano[4,3,2-cd]indazol-5-yl]-2-[[2-(phenylmethoxy)-ethyl](phenylmethyl)amino]acetamide, mp 165°–168° C.

A mixture of 1.3 g of the above acetamide and 0.10 g of 20% palladium hydroxide on carbon in 50 ml of glacial acetic acid stirred under hydrogen at atmospheric pressure until the hydrogen uptake measured 100 ml. The reaction mixture was filtered and coevaporated several times with methanol. The residue was dissolved in methanol and acidified with a solution of hydrogen chloride in 2-propanol. Further dilution with 2-propanol and cooling caused precipitation of a crystalline solid. The solid was isolated and dried to give 0.976 g of the product as a yellow crystalline solid with 2.5 equivalents of hydrogen chloride and 1.5 equivalents of water, mp 285° C. with decomposition.

EXAMPLE 14

2-[2-(Diethylamino)ethyl]-5-[[2-[(2-hydroxyethyl)-amino]ethyl]amino-2H-[1]benzopyrano[4,3,2-cd]indazol-9-ol, hydrochloride (1:3.5)

To a mixture of 2.45 g of N-[2-[2-(diethylamino)-ethyl]-9-hydroxy-2H-[1]benzopyrano[4,3,2-cd]indazol-5-yl]-2-[[2-(phenylmethoxy)ethyl](phenylmethyl-)amino]acetamide in 80 ml of dry tetrahydrofuran under argon was added 40 ml of 1M solution of borane tetrahydrofuran complex in tetrahydrofuran. After 24 hours at 50° C., an additional 3 ml of borane tetrahydrofuran complex was added and the reaction continued for another three hours at 50° C. The mixture was poured into 150 ml of methanol, heated under reflux overnight, evaporated to dryness, and the residue of crystallized from diethyl ether to afford 1.36 g of 2-[2-diethylamino)ethyl]-5-[[2-(phenylmethoxy)ethyl](phenylmethyl)amino]ethyl]amino]-2H-[1]benzopyrano[4,3,2-cd]indazol-9-ol.

A mixture of 1.3 g of the above material was debenzylated in 50 ml of glacial acetic acid in an atmosphere of hydrogen at atmospheric pressure in the presence of 0.2 g of 20% palladium on carbon over a period of 48 hours. The mixture was filtered, concentrated under reduced pressure, and reevaporated several times from methanol. The residue in 2-propanol was acidified with hydrogen chloride in 2-propanol, providing the title compound.

EXAMPLE 15

2-[2-[(2-Hydroxyethyl)amino]ethyl]-5-nitro-2H-[1]-benzopyrano[4,3,2-cd]indazol-9-ol, hydrochloride A mixture of 3 g of 1-chloro-7-hydroxy-4-nitro-9H-xanthen-9-one, 2.7 g of 2-[(hydrazinoethyl)amino]-ethanol, and 2 ml of diisopropylethylamine in 60 ml of N,N-dimethylformamide was stirred under an argon atmosphere for one hour. The solution was concentrated in vacuo and the residue was triturated with 2-propanol to leave a yellow crystalline solid. The solid was dissolved in minimal hot N,N-dimethylformamide and then acidified with a solution of hydrogen chloride in 2-propanol to give 3.28 g of produce as a salt with 0.98 equivalents of hydrogen chloride, mp>300° C.

EXAMPLE 16

5-Amino-2-[2-(2-hydroxyethyl)amino]ethyl]-2H-[1]-benzopyrano[4,3,2-cd]indazol-9-ol, hydrochloride A mixture of 3.7 g of 2-[2-[(2-hydroxyethyl)-amino]ethyl]-5-nitro-2H-[1]benzopyrano[4,3,2-cd]-indazol-9-ol, hydrochloride and 0.25 g of 20% palladium on carbon in 300 ml of anhydrous methanol was stirred under hydrogen at atmospheric pressure until the hydrogen uptake measured 650 ml. The mixture was filtered and the filtrate concentrated in vacuo to dryness. The residue was dissolved in 100 ml of boiling methanol and the solution acidified with hydrogen chloride in 2-propanol. The solid was collected, washed with 2-propanol, and dried in vacuo at 60° C. to give 2.1 g of product as a salt with 1.8 equivalents of hydrogen chloride and 0.88 equivalent of water, mp 315° C. with decomposition.

EXAMPLE 17

2-[2-[(2-Hydroxyethyl)amino]ethyl]-9-hydroxy-2H-[1]benzopyrano[4,3,2-cd]indazol-5-yl]-2-[(2-hydroxyethyl)amino]acetamide, hydrochloride A mixture of 10 g of 1-chloro-7-hydroxy-4-nitro-9H-xanthen-9-one, 20.1 g of N-(2-hydrazinoethyl)-N-[2-(phenylmethoxy)ethyl]benzenemethanamine and 6.0 ml of diisopropylethylamine in 200 ml of N,N-dimethylformamide was stirred under an argon atmosphere for two hours. The reaction was concentrated in vacuo to an oil which crystallized on standing. Trituration of the solid with 2-propanol, filtration, and drying at 60° C. afforded 15.4 g of product. Recrystallization from methanol gave 5-nitro-2-[2-[[2-phenylmethoxy)ethyl](phenylmethyl)-amino]ethyl]-2H-[1]benzopyrano[4,3,2-cd]indazol-9-ol, mp 155°-156° C. after recrystallization from acetone.

A mixture of 10 g of 5-nitro-2-[2-[[2-(phenylmethoxy)ethyl](phenylmethyl)amino]ethyl]-2H-[1]benzopyrano[4,3,2-cd]indazol-9-ol and 5 g of Raney nickel in 150 ml N,N-dimethylformamide was stirred at atmospheric pressure under hydrogen overnight. The mixture was filtered and the filtrate was concentrated in vacuo to a thick oil. The 5-amino-2-[2-[[2-(phenylmethoxy)ethyl](phenylmethyl)amino]ethyl]-2H-[1]benzopyrano[4,3,2-cd]indazol-9-ol so obtained was used without further processing.

To a solution of 9.44 g of the above oil in 220 ml of dry tetrahydrofuran was added 14.2 g of N-[2-(phenylmethoxy)ethyl]-N-(phenylmethyl)glycine and 4.3 g of N'-(ethylcarbonimidoyl)-N,N-dimethyl-1,3-propanediamine, monohydrochloride. The mixture was stirred under argon at 25° C. for three hours. The reaction mixture was poured into 200 ml of aqueous saturated sodium bicarbonate solution and then extracted into dichloromethane. The extracts were concentrated in vacuo and the residue was triturated with acetone. The resulting solid was recrystallized from acetone to afford N-[9-hydroxy-2-[2-[[2-(phenylmethoxy)ethyl](-phenylmethyl)amino]ethyl]-2H-[1]-benzopyrano[4,3,2-cd]indazol-5-yl]-2-[[2-(phenylmethoxy)ethyl](phenylmethyl)amino]acetamide, mp 106°-110° C.

A mixture of 2.5 g of the above acetamide and 0.20 g of 20% palladium hydroxide on carbon in 50 ml of glacial acetic acid was stirred under a hydrogen atmosphere at atmospheric pressure for 24 hours. The mixture was filtered through a celite pad and the filtrate was evaporated to an oily residue. The residue was dissolved in minimal methanol and then acidified with a solution of hydrogen chloride in 2-propanol. The precipitate was collected and dried in vacuo to give 2-[2-[(2-hydroxyethyl)amino]-ethyl]-9-hydroxy-2H-[1]benzopyrano[4,3,2-cd]indazol-5-yl]-2-[(2-hydroxyethyl)amino]acetamide, hydrochloride, having 2.44 equivalents of hydrogen chloride and 2.61 equivalents of water, mp 223° C. with decomposition.

EXAMPLE 18

2-[2-[(2-Hydroxyethyl)amino]ethyl]-5-[[2-[(2-hydroxyethyl)amino]ethyl]amino-2H-[1]benzopyrano[4,3,2-cd]-indazol-9-ol, hydrochloride A solution of 3.0 g of N-[9-hydroxy-2-[2-[[2-(phenylmethoxy)ethyl] (phenylmethyl)amino]ethyl]-2H-[1]-benzopyrano[4,3,2-cd]indazol-5-yl]-2-[[2-(phenylmethoxy)-ethyl](phenylmethyl)amino]acetamide in 25 ml of tetrahydrofuran was treated with 15 ml of a 1M solution of lithium tetrahydroaluminate in tetrahydrofuran. The reaction was heated under reflux for five hours and then cooled to 5° C. Saturated aqueous ammonium chloride (20 ml) was carefully added and the mixture stirred at 25° C. overnight. The mixture was filtered, extracted with ethyl acetate, and the extract passed through a short column of silica gel with dichloromethane, affording a clear oil on evaporation. The oil crystallized from cold ether providing 2-[2-[[2-(phenylmethoxy)ethyl](phenylmethyl)amino]ethyl-5-[[2-[[2-(phenylmethoxy)ethyl]-(phenylmethyl)amino]ethyl]amino]-2H-[1]benzopyrano[4,3,2-cd]indazol-9-ol, mp 94°-96° C.

A mixture of 2.0 g of the above product and 0.3 g of 20% palladium hydroxide on carbon in 50 ml of glacial acetic acid was stirred under hydrogen at atmospheric pressure for 24 hours. The mixture was filtered and the filtrate concentrated in vacuo to an oil. The oil was dissolved in 2-propanol and and acidified with a solution of hydrogen chloride in 2-propanol. The resulting precipitate was collected and dried in vacuo at 56° C. to give the title salt, containing 2.94 equivalents of hydrogen chloride and 0.35 equivalents of water, 0.79 equivalents of 2-propanol, mp 335° C. with decomposition.

EXAMPLE 19

5-Nitro-2-[2-(diethylamino)ethyl]-8-methoxy-2H-[1]-benzopyrano[4,3,2-cd]indazol, hydrochloride A mixture of 5.0 g of 1-chloro-6-methoxy-4-nitro-9H-xanthen-9-one, 2.58 g of [2-(diethylamino)ethyl]-hydrazine, and 3.43 ml of diisopropylethylamine in 100 ml of N,N-dimethylformamide was stirred for two hours. The mixture was evaporated to dryness and the residue was triturated with 2-propanol. The solid was collected, washed with diethylether, and dried at 60° C. in vacuo to afford the title compound, a salt with 1.0 equivalent of hydrogen chloride, mp 285°–288° C.

EXAMPLE 20

5-Nitro-2-[2-(diethylamino)ethyl]-2H-[1]benzopyrano-[4,3,2-cd]indazol-8-ol, hydrochloride A mixture of 6.0 g of 1-chloro-6-hydroxy-4-nitro-9H-xanthen-9-one and 5.4 g of [2-(diethylamino)ethyl]-hydrazine and 3.9 ml of diisopropylethylamine in 100 ml of N,N-dimethylformamide was stirred at 25° C. for three hours. The mixture was evaporated and the residue crystallized from 2-propanol to afford the title compound, a salt with one equivalent of hydrogen chloride, mp 285° C. (decomposition).

EXAMPLE 21

5-Amino-2-[2-(diethylamino)ethyl]-2H-[1-]benzopyrano[4,3,2-cd]-indazol-8-ol

A solution of 5.0 g of 5-nitro-2-[2-(diethylamino)-ethyl]-2H-[1]benzopyrano[4,3,2-cd]indazol-8-ol in 200 ml of DMF with 0.2 g of 20% palladium hydroxide on carbon was stirred under a hydrogen atmosphere for 24 hours. The mixture was filtered and the filtrate was evaporated in vacuo to leave the product 5-amino-2-[2-(diethylamino)-ethyl]-2H-[1]benzopyrano[4,3,2-cd]indazol-8-ol as an oily solid.

PREPARATION OF STARTING MATERIALS

EXAMPLE 22

1-Chloro-7-methoxy-4-nitro-9H-xanthen-9-one 2-(5-Chloro-2-nitrophenoxy)-5-methoxybenzoic acid, 50 g, was added to 400 g of polyphosphoric acid, and the mixture stirred at 110° C. for 24 hours. The mixture was poured into 2 liters of water, and the resulting precipitate filtered to afford a light green solid. Recrystallization from dimethylformamide gave the title compound as green needles, mo 249°–251° C.

EXAMPLE 23

2-(5-Chloro-2-nitrophenoxy)-5-methoxybenzoic acid

To a stirred suspension of 65 g of 2-(5-chloro-2-nitrophenoxy)-5-methoxybenzoic acid, methyl ester, in 600 ml of methanol, was added 97.5 ml of 6M KOH solution. This suspension was stirred for 18 hours and the solution which resulted was neutralized with 200 ml of 10% HCl solution. The precipitated crude acid product was collected by filtration and, after recrystallization from acetonitrile, yielded the title compound, mp 232°–234° C.

EXAMPLE 24

2-(5-chloro-2-nitrophenoxy)-5-methoxybenzoic acid, methyl ester

To a solution of 61.8 g of 2-hydroxy-5-methoxybenzoic acid, methyl ester in 700 ml DMF was added 14.96 g of a 60% suspension of sodium hydride in mineral oil. This was followed by addition of 50.88 g of sodium iodide, 64.64 g of copper(I)iodide, and 2.16 g of finely powdered copper metal. The mixture was heated to 85° C., for 15 minutes, then 71.7 g of 2,4-dichloronitrobenzene was added, and the reaction was stirred at 85° C. for 16 hours. The mixture was filtered, and the filtrate concentrated to an oily residue. Sodium thiosulfate, 400 ml of a 20% solution was added, followed by extraction with ethyl acetate (3×400 ml). The combined ethyl acetate extracts were washed with water (2×325 ml), dried over anhydrous sodium sulfate, then evaporated to afford a pale yellow solid, which was triturated with cyclohexane and filtered giving the title compound, mp 114°–116° C.

EXAMPLE 25

2-Hydroxy-5-methoxybenzoic acid, methyl ester

A mixture of 73 g of 5-methoxysalicylic acid, and 95 ml of concentrated hydrochloric acid in 700 ml of methanol was heated under reflux for 48 hours. Potassium carbonate (10 g) was added, and the mixture concentrated to an oily residue which was dissolved in 250 ml of ethyl acetate. This solution was washed with two 100 ml portions of 10% sodium bicarbonate solution, then dried over anhydrous sodium sulfate. Evaporation of solvent afforded the title compound as an amber oil.

EXAMPLE 26

1-chloro-7-hydroxy-4-nitro-9H-xanthen-9-one

A mixture of 10 g of 1-chloro-7-methoxy-4-nitro-9H-xanthen-9-one and 84 ml of a 1M solution of boron tribromide in dichloromethane in 280 ml of dichloromethane was stirred at room temperature under an argon atmosphere for 16 hours, and then it was treated with 100 ml of methanol, and stirred for three hours. The mixture was filtered to give a light green solid. Recrystallization from chloroformmethanol afforded the title compound, mp 290°–292° C.

EXAMPLE 27

2-(5-Chloro-2-nitrophenoxy)-4-methoxybenzoic acid, methyl ester

To a stirred solution of 15 g of methyl 2-hydroxy-4-methoxy-benzoate in 185 ml of dimethylformamide under argon was added 3.63 g of a 60% dispersion of sodium hydride in oil. To this slurry was added 12.35 g of sodium iodide, 15.69 g of copper(I)-iodide, and 0.525 g of copper powder. The mixture was heated for 15 minutes at 85° C. and 17.4 g of 2,4-dichloronitrobenzene was added. After 48 hours at 85° C., the reaction was cooled to 25° C. and methanol was added. The reaction was filtered and the filtrate was concentrated in vacuo to about 50 ml then diluted with 150 ml of ethylacetate. The solution was washed with a 20% aqueous solution of sodium thiosulfate and the organic portion was separated and dried over sodium sulfate. The solvent was evaporated to leave a tan solid. Recrystallization from ethyl acetate gave the title compound, mp 121°–123° C.

EXAMPLE 28

1-Chloro-6-methoxy-4-nitro-9H-xanthen-9-one

To 500 g of polyphosphoric acid stirred at 110° C. was added 62.9 g of 2-(5-chloro-2-nitrophenoxy)-4-methoxybenzoic acid, methyl ester. After 18 hours, the hot solution was poured into water, and the resulting precipitate collected. The solid was washed with water and isopropyl alcohol to give 57.9 g of the title compound, mp 211°–213° C. after recrystallization from DMF.

EXAMPLE 29

1-Chloro-6-hydroxy-4-nitro-9H-xanthen-9-one

A mixture of 20.0 g of 1-chloro-6-methoxy-4-nitro-9H-xanthen-9-one and 27.04 g of anhydrous powdered aluminum chloride was heated under reflux in 400 ml of 1,2-dichloroethane under an argon atmosphere for three hours. The liquid portion of the reaction mixture was decanted and evaporated to a dark residue. Both residues were combined and treated with 200 ml of concentrated hydrochloric acid for one hour. The solid was collected and washed with water and 2-propanol. The grey solid was dried in vacuo at room temperature to afford the title compound, mp 179°–182° C.

EXAMPLE 30

1-(2-Hydrazinoethyl)pyrrolidine

A mixture of 200 g of 85% hydrazine hydrate, 200 ml of water, 170 g of N-chloroethylpyrrolidine hydrochloride, and 70 g of potassium carbonate was boiled under reflux for seven hours. Sodium hydroxide (390 g) was added and the mixture was extracted with ether. The ethereal extract, dried and distilled, yielded the title compound, bp 107°–111° C. (18.5 mm).

EXAMPLE 31

N-[2-(Phenylmethoxy)ethyl]-N-(phenylmethyl)glycine, hydrobromide

A mixture of 13.8 g of bromoacetic acid, 200 ml of acetonitrile, 19.0 ml. of N,N-diisopropylethylamine, anmd 26.3 g of N,O-dibenzylethanolamine was heated for 24 hours under reflux. An additional portion of bromoacetic acid (3.5 g) was added, and heating continued for an additional 24 hours. Refrigeration of the resulting mixture caused the precipitation of the title compound as white needles of mp 115°–117° C. after recrystallization from ethyl acetate.

EXAMPLE 32

N-(2-Hydazinoethyl)-N-[2-phenylmethoxy)ethyl]benzenemethanamine

A solution of 10.0 g (0.033 mole) of N-(2-chloroethyl)-N-[2-(phenylmethoxy)ethyl]benzenemethanamine ]Nador et al., Acta Chim. Acad. Sci. Hung., 2:152 (1952)], 52.7 g (1.65 mol) of anhydrous hydrazine, and 210 ml of absolute ethanol was stirred at 25° C. for 18 hours. The mixture was poured into cold water and the solution thrice extracted with 500-ml portions of ether. The combined ether extracts were dried over anhydrous magnesium sulfate and concentrated at a temperature below 35° C. to give 7.2 g of the product as an unstable oil.

EXAMPLE 33

N,N-Diethyl-5-nitro-2H[1]benzothiopyrano[4,3,2-cd]-indazole-2-ethanamine

A mixture of 70.0 g (0.24 mol) of 1-chloro-4-nitro-9H-thioxanthen-9-one [J. Am. Chem. Soc., 74, 4296 (1952)], 39.4 g (0.30 mol) of 2-diethylaminoethyl)hydrazine [J. Med. Chem., 7, 493 (1964)], 41.5 g (0.30 mol) of $K_2CO_3$, and 1000 ml of xylene was heated under reflux for 1.5 hours, filtered to remove inorganic material, and allowed to cool to ambient temperature. The precipitate that accumulated was filtered and dried in vacuo to provide 65.7 g of product, mp 150°–152° C.

EXAMPLE 34

5-Nitro-2H[1]benzothiopyrano[4,3,2-cd]indazole-2-ethanamine

A solution of 26.1 g (0.35 mol) of 2-aminoethyl)hydrazine [British Pat. No. 880,332] in 1.4 l of DMF at 25° C. was treated portionwise with 81.7 g (0.28 mol) of 1-chloro-4-nitro-9H-thioxanthen-9-one over a 4.5 hour span. The precipitate that accumulated was collected, washed with MeOH, and taken up in 2.5 l of boiling $H_2O$. The insoluble material was removed by filtration and the filtrate was allowed to cool to room temperature and treated with 100 ml of 2N $NH_4OH$ to produce 39.3 g of orange solid, mp 199°–203° C.

EXAMPLE 35

2-[[2-(5-Nitro-2H[1]benzothiopyrano[4,3,2-cd]indazol-2-yl)ethyl]amino]ethanol, hydrochloride salt A suspension of 42.3 g (0.4 mol) of 1-chloro-4-nitro-9H-thioxanthen-9-one in 350 ml of pyridine was treated dropwise with 20.7 g (0.17 mol) of 2-[(hydrazinoethyl)amino]ethanol over a five minute span, keeping the temperature less than 30° C. The mixture was stirred overnight at 25° C. and the precipitate was collected. The filtrate was treated with an excess of i-PrOH saturated with gaseous HCL to precipitate a second crop of product. The two crops were combined and recrystallized from DMSO to give 31.1 g of product, mp 293°–295° C. dec.

Other 5-nitro-2-(substituted)-2H[1]benzothiopyrano[4,3,2-cd]indazoles, prepared in the manner of Examples 33–35, are as follows:

N,N-dimethyl-5-nitro-2H[1]benzothiopyrano[4,3,2-cd]-indazole-2-ethanamine, mp 184°–189° C., methanesulfonic acid salt, mp 266° C. dec.

N,N-dimethyl-5-nitro-2H[1]benzothiopyrano[4,3,2-cd]-indazole-2-propanamine, mp 132°–135° C., hydrochloride salt, mp 309° C. dec.

2-[(Hydrazinoethyl)amino]ethanol may be prepared by reaction of hydrazine with N-(2-hydroxyethyl)aziridine in an aqueous medium at reflux temperature. It is isolated by standard procedures as a clear liquid which has bp 120° C. at 0.035 mmHg.

EXAMPLE 36

5-Amino-N,N-diethyl-2H[1]benzothiopyrano[4,3,2-cd]-indazole-2-ethanamine

A mixture of 54.0 g (0.15 mol) of N,N-diethyl-5-nitro-2H[1]benzothiopyrano[4,3,2-cd]indazole-2-ethanamine, 1.0 g of 20% Pd/C, and 600 ml of HOAc was hydrogenated in a Parr shaker at 25° C. and an initial pressure of 50.0 psi. the mixture was filtered and the filtrate was concentrated in vacuo to a small volume, treated with 1

1 of H₂O, made basic (pH 6.5) with 50% aqueous NaOH, and extracted three times with CHCl₃. The extracts were combined, dried (MgSO₄), and concentrated to dryness in vacuo. Crystallization of the residue from CH₃CH gave 40.0 g of the product, mp 100°–102° C.

Other 5-amino-2-(substituted)-2H[1]benzothiopyrano[4,3,2-cd]indazoles, prepared in like manner, are as follows:

2-[[2-(5-amino-2H[1]benzothiopyrano[4,3,2-cd]indazol-2-yl)ethyl]amino]ethanol, hydrochloride salt, mp greater than 285° C. dec.

5-amino-N,N-dimethyl-2H[1]benzothiopyrano[4,3,2-cd]-indazole-2-ethanamine, mp 131°–134° C., hydrochloride salt, mp 273° C. dec.

5-amino-N,N-dimethyl-2H[1]benzothiopyrano[4,3,2-cd]-indazole-2-propanamine, hydrochloride salt, mp 264° C. dec.

5-amino-2H[1]benzothiopyrano[4,3,2-cd]indazole-2-ethanamine, mp 131°–140° C., hydrochloride salt, mp greater than 300° C. N-[2-(5-amino-2H[1]benzothiopyrano[4,3,2-cd]indazol-2-yl)ethyl]acetamide, mp 213°–216° C., hydrochloride salt, mp 287° C. dec.

EXAMPLE 37

5-[[2-(Diethylamino)ethyl]amino]-N,N-diethyl-2H[1]-benzothiopyrano[4,3,2-cd]indazole-2-ethanamine, hydrochloride salt A mixture of 3.0 g (0.0089 mol) of 5-amino-N,N-diethyl-2H[1]benzothiopyrano[4,3,2-cd]indazole-2-ethan amine, 3.5 g (0.013 mol) of 2-(diethylamino)-ethylbromide, hydrobromide, and 4.6 g (0.034 mol) of K₂CO₃ in 120 ml of toluene was heated under reflux for eight hours, allowed to cool to room temperature overnight, and filtered. The solid was triturated in boiling CH₃CN, filtered to remove insoluble inorganics, and concentrated to dryness in vacuo. The residue was dissolved in acetone and treated with an excess of iPrOH saturated with gaseous HCl. The precipitate that accumulated was collected and recrystallized fom CH₃CH/EtOH mixture to give 2.4 g of product, mp 234°–236° C.

EXAMPLE 38

N-[2-[2-(Diethylamino)ethyl]-2H[1]benzothiopyrano[4,3,2-cd]indazol-5-yl]-1,2-ethanediamine, hydrobromide salt A solution of 5.0 g (0.015 mol) of 5-amino-N,N-diethyl-2H[1]benzothiopyrano[4,3,2-cd]indazole-2-ethanamine and 9.2 g (0.045 mol) of 2-bromoethylamine, hydrochloride in 50 ml of EtOH was heated under reflux for four days and allowed to cool to room temperature. The solid was collected and recrystallized from MeOH to give 2.6 g of product, mp 263° C. dec.

EXAMPLE 39

N-[2-[2-(Diethylamino)ethyl]-2H[1]-benzothiopyrano-[4,3,2-cd]indazol-5-yl]acetamide, hydrochloride salt A solution of 3.0 g (0.0089 mol) of 5-amino-N,N-diethyl-2H[1]benzothiopyrano[4,3,2-cd]indazole-2-ethanamine in 30 ml of pyridine was treated dropwise with 0.9 g (0.011 mol) of acetyl chloride, stirred at 25° C. for 30 minutes, and filtered. The solid was recrystallized from EtOH to provide 2.6 g of product, mp 208°–211° C.

The free base, mp 151°–154° C., may be prepared by dissolving the above product in a minimum amount of hot EtOH followed by treatment with an excess of 1N NaOH.

EXAMPLE 40

2L-Chloro-N-[2-[2-(diethylamino)ethyl]-2H[1]benzothiopyrano[4,3,2-cd]indazol-5-yl]acetamide A mixture of 10.2 g (0.030 mol) of 5-amino-N,N-diethyl-2H[1]benzothiopyrano[4,3,2-cd]indazole-2-ethanamine and 8.3 ml (0.060 mol) of Et₃N in 90 ml of CHCl₃ was treated dropwise with a solution of 3.6 ml (0.045 mol) of chloroacetyl chloride in 20 ml of CHCl₃ over ten minutes. The reaction mixture was stirred at room temperature for three hours, treated with an additional 1.2 ml (0.015 mol) of chloroacetyl chloride in 50 ml of CHCl₃, and concentrated to dryness in vacuo. The residue was triturated three times with cold MeOH to give 8.3 g of product, mp 204°–205° C. dec.

EXAMPLE 41

N'-[2-[2-(Diethylamino)ethyl]-2H[1]benzothiopyrano-[4,3,2-cd]indazol-5-yl]-N,N-dimethyl-methanimidamide A solution of 3.0 g (0.089 mol) of 5-amino-N,N-diethyl-2H[1]bezothiolyrano[4,3,2-cd]indazole-2-ethanamine in 100 ml of DMF was treated with 1.3 g (0.011 mol) of N,N-dimethylformamide, dimethyl acetal. The reaction mixture was heated at 90° C. for 18 hours, treated with an additional 0.6 g (0.0052 mol) of N,N-dimethylformamide, dimethyl acetal, stirred at 90° C. for an additional 18 hours, and poured into 1 l of H₂O. The solid that accumulated was collected and recrystallized from cyclohexane to give 2.8 g of product, mp 108°–109° C.

EXAMPLE 42

3-[2-[[2-[2-(Diethylamino)ethyl]-2H[1]benzothiopyrano-[4,3,2-cd]indazol-5-yl]amino]ethyl]-2-oxazolidinone A mixture of 5.8 g 0.017 mol) of 5-amino-N,N-diethyl-2H[1]benzothiopyrano[4,3,2-cd]indazole-2-ethanamine and 5.1 g (0.034 mol) of 3-(2-chloroethyl)-2-oxazolidinone was stirred at 150° C. for two hours, dissolved in 100 ml of CHCl₃ and washed twice with 2N NaOH. The solution was dried (MgSO₄) and concentrated in vacuo to dryness. The residue was flash chromatographed over silica gel, eluting with a CHCl₃/MeOH (4/1) mixture. The appropriate fractions were combined and concentrated to dryness in vacuo. The residue was treated with 20 ml of acetone and the resulting suspension was treated with 150 ml of Et₂O. The resulting precipitate was collected and dried to give 4.9 g of product, mp 90°–94° C.

EXAMPLE 43

N,N-Diethyl-5-[[2-(dimethylamino)ethyl]amino]-2H-[1]benzothiopyrano[4,3,2-cd]indazole-2-ethanamine A mixture of 5.0 g (0.015 mol) of 5-amino-N,N-diethyl-2H[1]benzothiopyrano[4,3,2-cd]indazole-2-ethanamine, 2.4 g (0.015 mol) of 2,2-diethoxy-N,N-dimethyl ethanamine, and 0.001 g of p-toluenesulfonic acid in 100 ml of 2-propanol was heated under reflux for four hours, allowed to cool to room temperature, and treated portionwise with 1.0 g (0.026 mol) of NaBH₄ over a two hour period. The mixture was stirred at room temperature for 16 hours and poured into 1 l of H₂O. The precipitate that formed was collected, washed with H₂O, dried, and recrystallized to give the product.

An example of another 5-(monoalkylated or acylated)-2-(substituted)benzothiopyrano[4,3,2-cd]-indazole, prepared in the manner of Examples 5–11, is as follows: N-[2-[2-(diethylamino)ethyl]-2H[1]benzothiopyrano[4,3,2-cd]indazol-5-yl]-1,3-propanediamine, hydrochloride salt, mp 222° C. dec.

EXAMPLE 44

N-[2-(Acetyloxy)ethyl]-N-[2-(5-nitro-2H[1]benzothiopyrano[4,3,2-cd]indazole-2-yl)ethyl]acetamide A mixture of 1.0 g (0.0025 mol) of 2-[[2-(5-nitro-2H[1]benzothiopyrano[4,3,2-cd]indazol-2-yl)-ethyl]amino]ethanol and 0.5 g (0.0053 mol) of sodium acetate in 50 ml of Ac₂O was stirred at 25° C. for 24 hours and poured into 500 ml of H₂O. The precipitate that accumulated was collected and dried to give 1.0 g of product, mp 113°–116° C.

EXAMPLE 45

5-Nitro-N-[2-(phenylmethoxy)ethyl]-N-(phenylmethyl)-2H[1]benzothiopyrano[4,3,2-cd]indazole-2-ethanamine, hydrochloride

Method A

A mixture of 5.0 g (0.017 mol) of 1-chloro-4-nitro-9H-thioxanthen-9-one, 6.0 g (0.020 mol) of 2-[N-[2-(phenylmethoxy)ethyl]-N-(phenylmethyl)aminoethyl]hydrazine, 5 ml of triethylamine, and 100 ml of DMF was stirred at 25° C. for one hour, then at 80° C. for 15 minutes. The mixture was poured into water and the solution was extracted with dichloromethane. The dired dichloromethane layer was chromatographed on silica gel, eluting first with dichloromethane then 9:1 dichloromethane-methanol to give the product as an oil. The oil was dissolved in 20 ml of dichloromethane and treated with 2-propanol:ether saturated with gaseous HCl. The solid was collected and dried in vacuo to give 6.6 g of product, mp 210°–214° C.

N-(2-hydrazinoethyl)-N-[2-(phenylmethoxy)ethyl]-benzenementhanamine is prepared as follows: A solution of 10.0 g (0.033 g) of N-(2-chloroethyl)-N-[2-(phenylmethoxy)ethyl]benzenemethanamine [Nador, Kovatsits, and Gyermek, *Acta. Chim. Acad. Sci. Hung.* 2, 153 (1952)], 52.7 g (1.65 mol) of anhydrous hydrazine, and 210 ml of absolute ethanol was stirred at 25° C. for 18 hours. The mixture was poured into cold water and the solution was extracted with ether (3×250 ml). The combined ether layers were dried (Na₂SO₄) and concentrated at less than 35° C. to give 7.2 g of the product as an unstable oil.

Method B

A mixture of 1.0 g (0.0025 mol) of 2-[(2-5-nitro-2H[1]benzothiopyrano[4,3,2-cd]indazol-2-yl)-ethyl]amino]ethanol in 50 ml of DMF at 25° C. was treated with a suspension of 0.12 g (0.005 mol) of NaH in 20 ml of DMF, stirred at 25° C. for 15 minutes, and treated with 0.9 g (0.0053 mol) of benzyl bromide. The mixture was stirred at 60° C. for two hours and poured into 300 ml of H₂O. Workup as in Method A gave the product.

EXAMPLE 46

3-[2-(5-Nitro-2H[1]benzothiopyrano[4,3,2-cd]indazol-2-yl)ethyl]-2-oxazolidinone

A mixture of 1.0 g (0.0025 mol) of 2-[[2-(5-nitro-2H[1]benzothiopyrano[4,3,2-cd]indazol-2-yl)-ethyl]amino]ethanol, 10.0 g (0.045 mol) of diphenyl carbonate, 0.3 g (0.0036 mol) of NaOAc and 10.0 g of phenol was treated at 110° C. for 16 hours, allowed to cool to room temperature, and triturated twice in a small amount of acetone. The insoluble material was recrystallized to give the product.

An example of another 5-nitro-2-(substituted)-2H[1]benzothiopyrano[4,3,2-cd]indazole where the 2-substituent contains one or more reactive groups such as NH, NH₂, or OH, prepared as described in Examples 12 through 14 to protect these functionalities, is as follows:

N-[2-(5-nitro-2H[1]benzothiopyrano[4,3,2-cd]indazol-2-yl)ethyl]acetamide, mp 259° C. dec.

These derivatized compounds are in turn reduced to the 5-amino compounds as described in Example 36 above, except when a benzyl group is used as the protecting group. In this instance, the reductions are carried out in MeOH, THF, or MeOH/THF mixtures using Raney Nickel as the catalyst.

EXAMPLE 47

2-[[2-[5-[[2-(Diethylamino)ethyl]amino]-2H[1]benzothiopyrano[4,3,2-cd]indazol-2-yl]ethyl]amino]ethanol, hydrochloride salt A mixture of 3.3 g (0.008 mol) of N-[2-(acetyloxy)ethyl]-N-[2-(5-amino-2H[1]benzothiopyrano-[4,3,2-cd]indazol-2-yl)ethyl]acetamide, 3.2 g (0.012 mol) of 2-(diethylamino)ethyl bromide, hydrobromide and 2.5 g (0.018 mol) of K₂CO₃ in 250 ml of toluene was heated under reflux for four hours, allowed to cool to room temperature overnight, and filtered. The filtrate was concentrated in vacuo to dryness and the residue was flash chromatographed over 200 g of silica gel, eluting with a CH₂Cl₂/MeOH (6/1) mixture. The appropriate fractions were combined and concentrated to dryness in vacuo to give N-[2-(acetyloxy)ethyl]-N-[2-[5-[(2-diethylamino)-ethyl]-2H[1]benzothiopyrano[4,3,2-cd]indazol-2-yl]-ethyl]acetamide as an oil. This material was treated with treated with 150 ml of 2N HCl, heated under reflux for one hour, and allowed to cool to room temperature overnight. The reaction mixture was made basic with 50% aq NaOH and the precipitate that formed was collected, dried in vacuo, and dissolved in 200 ml of acetone. the solution was treated dropwise with i-PrOH saturated with gaseous HCl until precipitation was complete. The solid was collected and dried in vacuo to give 0.75 g of product, mp 208°–212° C.

EXAMPLE 48

2-[[2-[[2-[2-(Diethylamino)ethyl]-2H[1]benzothiopyrano[4,3,2-cd]indazol-5-yl]amino]ethyl]amino]-ethanol, hydrochloride salt A mixture of 2.2 g (0.0049 mol) of 3-[2-[[2-[2-(diethylamino)ethyl]-2H[1]benzothiopyrano[4,3,2-cd]-indazol-5-yl]amino]ethyl]-2-oxazolidinone, 20 ml of 2N KOH in MeOH, 10 ml of H₂O, and 10 ml of THF was heated under reflux under a N₂ atmosphere for 14 hours and poured into 250 ml of H₂O. The mixture was extracted three times with CH₂Cl₂ and the CH₂Cl₂ extracts were combined, dried (MgSO₄), and concentrated to dryness in vacuo. The residue was dissolved in 125 ml of i-PrOH and treated dropwise with i-PrOH saturated with gaseous HCl until precipitation was complete. The solid was collected and triturated in a boiling EtOH/i-PrOH (1/1) mixture to give 2.1 g of product, mp 202°–210° C.

EXAMPLE 49

2-[[2-[5-[[2-(Diethylamino)ethyl]amino]-2H[1]benzothiopyrano[4,3,2-cd]indazol-2-yl]ethyl]amino]ethanol, hydrochloride salt A mixture of 5.0 g (0.0082 mol) of 5-[[2-diethylamino)ethyl]amino]-N-[2-(phenylmethoxy)ethyl]-N-(phenylmethyl)-2H[1]benzothiopyrano[4,3,2-cd]indazole-2-ethanamine, 0.2 g of 20% Pd/C, and 100 ml of HOAc was hydrogenated in a Parr shaker at 25° C. and an initial pressure of 50 psi. The mixture was filtered and the filtrate was concentrated in vacuo to a small volume, treated with 300 ml of H₂O, made basic with 50% aqueous NaOH, and extracted three times with CHCl₃. The extracts were combined, dried (MgSO₄), and concentrated in vacuo to dryness. The residue was dissolved in a minimum amount of acetone and treated with i-PrOH saturated with gaseous HCl until precipitation was complete. The solid was collected and recrystallized to give the product, mp 208°–212° C.

EXAMPLE 50

2-[[2-[5-[[2-[(2-Hydroxyethyl)amino]ethyl]amino]-2H[1]benzothiopyrano[4,3,2-cd]indazol-2-yl]ethyl]amino]ethanol, hydrochloride salt A mixture of 5.1 g (0.012 mol) of N-[2-(acetyloxy)ethyl]-N-[2-(5-amino-2H[1]benzothiopyrano[4,3,2-cd]indazol-2-yl)ethyl]acetamide, hydrochloride salt and 11.6 g (0.077 mol) of 3-(β-chloroethyl)-2-oxazolidinone was stirred at 150° C. for 2 hours, dissolved in 20 ml of a CH₂Cl₂/MeOH (20/1) mixture, and flash chromatographed over silica gel, eluting with a CH₂Cl₂/MeOH (20/1) mixture. The appropriate fractions were combined and concentrated to dryness in vacuo. The residue was treated with 20 ml of 2N KOH in MeOH, 10 ml of H₂O, and 10 ml of THF, and the mixture was heated under reflux under a N₂ atmosphere for 16 hours. The mixture was treated with 100 ml of H₂O and 100 ml of CH₂Cl₂ and the layers were separated. The aqueous phase was extracted twice with CH₂Cl₂ and the Ch₂Cl₂ extracts were combined, dried (MgSO₄), and concentrated to dryness in vacuo. The residue was dissolved in 50 ml of EtOH and treated with an excess of i-PrOH saturated with gaseous HCl. The precipitate was collected and recrystallized from MeOH to give 6.0 g of product, mp 222°–225° C.

Other 5-(substituted amino)-2-(substituted)-2H[1]benzothiopyrano[4,3,2-cd]indazoles where the 2-substituent contains reactive groups such as NH, NH₂, or OH which have been protected, prepared in the manner of Examples 47–51, are as follows:

3-[2-[[2-[2-[(2-hydroxyethyl)amino]ethyl]-2H[1]benzothiopyrano[4,3,2-cd]indazol-5-yl]amino]ethyl]-2-oxazolidinone, hydrochloride salt, mp 180°–182° C.

N-[2-[5-[[2-(2-oxo-3-oxazolidinyl)ethyl]amino]-2H[1]benzothiopyrano[4,3,2-cd]indazol-2-yl]ethyl]-acetamide, mp 145°–147° C.

2-[[2-[[2-(2-aminoethyl)-2H[1]benzothiopyrano[4,3,2-cd]indazol-5-yl]amino]ethyl]amino]ethanol, hydrochloride salt, mp 264° C. dec.

EXAMPLE 51

N-[2-(Diethylamino)ethyl]-N-[2-[2-(diethylaminoethyl]-2H[1]benzothiopyrano[4,3,2-cd]indazol-5-yl]-acetamide A solution of 5.0 g (0.011 mol) of 5-[[(2-diethylamino)ethyl]amino]-N,N-diethyl-2H[1]benzothiopyrano[4,3,2-cd]indazole-2-ethanamine in 100 ml of pyridine was treated with 1.2 g (0.015 mol) of acetyl chloride, heated under reflux for two hours, and poured into 1 l of H₂O. The precipitate that formed was collected, dried, and recrystallized to give the product.

Other 5-(monosubstituted amino)-2-(substituted)-2H[1]benzothiopyrano[4,3,2-cd]indazoles are acylated at N₅ in like manner.

EXAMPLE 52

5-[[N'-[2-(Diethylamino)ethyl]-N-ethyl]amino]-N,N-diethyl-2H[1]benzothiopyrano[4,3,2-cd]indazole-2-ethanamine Twenty-five milliliters of a 1M solution of LiAlH₄ (0.025 mol) in THF at 25° C. was treated dropwise with a solution of 5.0 g (0.01 mol) of N-[2-diethylamino)ethyl]-N-[2-[2(diethylamino)ethyl]-2H[1]-benzothiopyrano[4,3,2-cd]indazol-5-yl]acetamide in 25 ml of THF over a 30 minute period. The mixture was heated under reflux for two hours, allowed to cool to room temperature, and treated dropwise with H₂O until the excess LiAlH₄ was decomposed. The mixture was treated with 10 g of MgSO₄, stirred for 30 minutes and filtered. The insoluble material was washed with THF three times and the filtrates were combined and concentrated in vacuo to dryness. The residue was crystallized and dried to give the product.

Other 5-(dialkylamino)-2-(substituted)-2H[1]-benzothiopyrano[4,3,2-cd]indazoles were prepared from the corresponding acylated intermediates in like manner.

EXAMPLE 53

N,N-Diethyl-7,10-dimethoxy-5-nitro-2H[1]benzothiopyrano[4,3,2-cd]indazole-2-ethanamine A mixture of 16.2 g (0.046 mol) of 1-chloro-5,8-dimethoxy-4-nitro-9H-thioxanthen-9-one and 9.1 g (0.069 mol) of 2-(diethylaminoethyl)hydrazine in 400 ml of DMF was stirred at 25° C. for six hours. The precipitate that accumulated was collected and dried to give 14.8 g of product, mp 188°–190° C.

1-Chloro-5,8-dimethoxy-4-nitro-9H-thioxanthen-9-one is prepared as follows: A solution of 9.5 g (0.048 mol) of 2-amino-3,6-dimethoxybenzoic acid [P. K. Bannerjee and D. N. Chaudhury, *J. Indian Chem. Soc.*, 86 (4), 257 (1959)], 4.6 ml (0.11 mol) of 50% aqueous NaOH, 60 ml of H₂O, and 3.3 g (0.048 mol) of NaNO₂ was added slowly to a mixture of 15 ml of concentrated HCl and 20 g of ice chips which had been previously cooled in a salt-ice bath to −5° C. Good stirring was maintained throughout the addition and the temperature was kept below 5° C. After the addition was complete, the mixture was stirred to 0° C. for one hour, neutralized (pH 5.5) with potassium acetate, and added while cold in a thin stream to an 80° C. solution of 22.2 g (0.15 mol) of potassium ethyl xanthate in 75 ml of H₂O under N₂. Copious N₂ evolution (foaming) occurred during the addition, and heat was applied as needed to maintain the temperature at 75°–80° C. The reaction mixture, under N₂, was cooled to 20° C. and acidified (pH 3) with concentrated HCl. The oily material which separated was extracted into CH₂Cl₂ (2X), keeping contact with air to a minimum. The extracts were combined, dried under N₂ (MgSO₄), and concentrated on a steam bath to a brown oil using a stream of N₂. The crude 2,5-dimethoxy-6-thiobenzoic acid was immediately dissolved in 40 ml of hot anhydrous EtOH and added to a premixed, 25° C. mixture of 9.2 g (0.048 mol)

of 2,4-dichloronitrobenzene in sodium ethoxide [2.2 g (0.096 g atom) of sodium spheres dissolved in 90 ml of anhydrous EtOH]. The resulting suspension was heated under reflux for 16 hours, concentrated to dryness in vacuo and taken up in 250 ml of ether and 250 ml of H$_2$O. The layers were separated and the aqueous layer was extracted twice with ether to remove organic soluble impurities, and made acidic (pH 1) with concentrated HCl. The solid which formed was collected, dried, and recrystallized from EtOH to give a first crop of product. The mother liquor was concentrated to dryness in vacuo and the residue was crystallized from CH$_3$CN to give a second crop of product. The mother liquor was concentrated to dryness in vacuo and the residue was flash chromatographed over 500 g of silica gel, eluting with CH$_2$Cl$_2$/MeOH (15/1). Combination of the appropriate fractions, concentration to dryness in vacuo, and crystallization of the residue from acetonitrile provided a third crop of product. All crops were combined to give 7.8 g of 2-[(5-chloro-2-nitrophenyl)-thio]-3,6-dimethoxybenzoic acid, mp 218°–220° C.

A mixture of 19.7 g (0.053 mol) of the above benzoic acid, 600 ml of trifluoroacetic acid, and 300 ml of trifluoroacetic anhydride was stirred at 50° C. for four hours, treated with an additional 70 ml of trifluoroacetic anhydride, and stirred at 50° C. for 20 hours. The reaction mixture was poured into 9 l of H$_2$O and the precipitate that accumulated was collected and dried to give 16.4 g of 1-chloro-5,8-dimethoxy-4-nitro-9H-thioxanthen-9-one, mp 222°–228° C.

Other 10-hydroxy-7-methoxy-, 10-methoxy-7-hydroxy-, and 7,10-dimethoxy-5-nitro-2-(substituted)-2H[1]benzothiopyrano[4,3,2-cd]indazoles can be prepared in the manner of Examples 33 through 35 and 54. One such compound is 2-[2-(diethylamino)-ethyl]-7-methoxy-5-nitro-2H[1]benzothiopyrano[4,3,2-cd]indazol-10-ol, hydrochloride salt, mp 267°–270° C. The latter compound is prepared from 1-chloro-5-methoxy-8-hydroxy-4-nitro-9H-thioxanthen-9-one which in turn is prepared as follows: A suspension of 5.8 g (0.016 mol) of 2-[(5-chloro-2-nitrophenyl)thio]-3,6-dimethoxybenzoic acid, 50 ml of toluene, and 3.8 g (0.032 mol) of thionyl chloride was heated under reflux for two hours, concentrated to dryness in vacuo, and dissolved in 50 ml of nitrobenzene. The solution was treated portionwise with 3.6 g (0.026 mol) of AlCl$_3$, keeping the temperature below 35° C. during the addition. The mixture was stirred for two hours at 70° C., chilled in a refrigerator overnight, and poured into 400 ml of ice-cold H$_2$O. The mixture was extracted four times with CH$_2$Cl$_2$ and the extracts were combined, dried (MgSO$_4$), and concentrated in vacuo to dryness. The residue was triturated successively in petroleum ether and hot MeOH, and recrystallized from DMF to give 1.2 g of product, 272°–273° C.

EXAMPLE 54

5-Amino-N,N-diethyl-7,10-dimethoxy-2H[1]benzothiopyrano[4,3,2-cd]indazole-2-ethanamine 3.1 g of N,N-diethyl-7,10-dimethoxy-5-nitro2H[1]benzothiopyrano[4,3,2-cd]-indazole-2-ethanamine was hydrogenated and the product was isolated as described in Example 36 to give 2.3 g, mp 134°–139° C.

Other 5-amino-7,10-(dimethoxy, hydroxymethoxy, and dihydroxy)-2-(substituted)-2H[1]benzothiopyrano[4,3,2-cd]indazoles can be prepared from the appropriate 7 and/or 10-methoxy-2-(substituted)-5-nitro-2H[1]benzothiopyrano[4,3,2-cd]indazoles in the manner of Example 36. One such compound is 5-amino-2-[2-(diethylamino)ethyl]-2H[1]-benzothiopyrano-[4,3,2-cd]indazole-7,10-diol, hydrochloride salt, mp 229√-233° C.

EXAMPLE 55

3-[2-[[2-[2-(Diethylamino)ethyl]-7,10-dimethoxy-2H-[1]benzothiopyrano[4,3,2-cd]indazol-5-yl]amino]-ethyl]-2-oxazolidinone A mixture of 2.2 g (0.0055 mol) of 5-amino-N,N-diethyl-7,10-dimethoxy-2H[1]benzothiopyrano[4,3,2-cd]indazole-2-ethanamine and 1.6 g (0.011 mole) of 3-(β-chloroethyl)-2-oxazolidinone was treated in the manner described in Example 42 to furnish 1.6 g of the title compound, mp greater than 250° C. dec.

Other 7,10-dimethoxy-5-(alkylamino or acylamino)-2-(substituted)-2H[1]benzothiopyrano[4,3,2-cd]-indazoles are prepared in the manner of Examples 37 through 43, with the exception of those compounds which contain side chains with reactive groups such as NH, NH$_2$, or OH. In such cases, the reactive groups must first be protected as described in Examples 44 through 46.

These derivatized compounds are in turn reduced to the 5-amino compounds as described in Example 36, except when benzyl groups are used as the protecting groups. In this instance, the reductions are carried out in MeOH, THF, or MeOH/THF mixtures using Raney nickel as the catalyst. The 5-amino compounds are then derivatized in the manner of Examples 37, 39, 40, 41, 42 and 47 to provide 7,10-dimethoxy-5-(monoalkylated or acylated)-2-(substituted)-2H[1]benzothiopyrano[4,3,2-cd]indazoles.

7,10-Dimethoxy-5-(monoalkylamino or acylamino-2-(substituted)-2H[1]benzothiopyrano[4,3,2-cd]indazoles may be acylated at N$_5$ in the manner of Example 50 and the acyl derivatives are reduced using LiAlH$_4$ in the manner of Example 50 to provide 7,10-dimethoxy-5-(disubstituted amino)-2-(substituted)-2H[1]benzothiopyrano[4,3,2-cd]indazoles.

EXAMPLE 56

2-[[2-[[2-[2-(Diethylamino)ethyl]-7,10-dimethoxy-2H-[1]benzothiopyrano[4,3,2-cd]indazole-5-yl]amino]-ethyl]amino]ethanol A mixture of 5.9 g (0.012 mol) of 3-[2-[[2-[2-diethylamino)ethyl]-7,10-dimethoxy-2H[1]benzothiopyrano[4,3,2-cd]indazol-5-yl]amino]ethyl]-2-oxazolidinone, 70 ml of 2N KOH in MeOH, 50 ml of THF, and 35 ml of H$_2$O was treated and the product isolated as described in Example 48 with the following exception: after concentrating the CHCl$_3$ extracts in vacuo to dryness, the residue was crystallized from CH$_3$CN to give 1.9 g of product, mp 119°–123° C.

Other 7,10-dimethoxy-2,5-(disubstituted)-2H-[1]benzothiopyrano[4,3,2-cd]indazoles are prepared in the manner of Examples 47–50.

EXAMPLE 57

2-[2-(Diethylamino)ethyl]-5-[[2-[(2-hydroxyethyl)-amino]ethyl]amino]-2H[1]benzothiopyrano[4,3,2-cd]-indazole-7,10-diol, hydrobromide salt A suspension of 1.9 g (0.0039 mol) of 2-[[2-[[2-[2-(diethylamino)ethyl]-7,10-dimethoxy-2H[1]benzothiopyrano[4,3,2-cd]indazol-5-yl]amino]ethyl]amino]-ethanol in 100 ml of ethylene dichloride was treated via syringe with 4.5 ml (12 mg, 0.047 mol) of boron tribromide, stirred at 25° C. for two days, treated with an additional 2.0 ml (5.2 g, 0.021 mol) of boron tribromide, and heated at 50° C. for two hours. The reaction mixture was cooled to 5° C., treated dropwise with 100 ml of MeOH, and evaporated to 50 ml using a stream of air. The precipitate was collected and recrystallized from MeOH to give, in two crops, 2.0 g of product, mp 243°–245° C.

Other 2,5-(disubstituted)-2H[1]benzothiopyrano[4,3,2-cd]indazole-7,10-diols, are prepared from the corresponding 7,10-dimethoxy precursors in the manner of Example 25. One such compound is 2-[2-(diethylamino)ethyl]-5-nitro-2H[1]benzothiopyrano[4,3,2-cd]indazole-7,10-diol, hydrobromide salt, mp 283° C. dec.

EXAMPLE 58

N,N-Diethyl-9-methoxy-5-nitro-2H[1]benzothiopyrano[4,3,2-cd]indazole-2-ethanamine A mixture of 1.2 g (0.0091 mol) of 2-(diethylaminoethyl)hydrazine, 2.0 g (0.0069 mol) of 1-chloro-7-methoxy-4-nitro-9H-thioxanthen-9-one, and 0.97 g (0.0069 mol) of powdered $K_2CO_3$ in 30 ml of xylene was heated at 70° C. for 1.5 hours, chilled in an ice bath, and filtered. The solid was triturated in $H_2O$ and dried to give 1.4 g of product, mp 154°–156° C. The product was taken up in 30 ml of boiling EtOH, treated with 4.0 ml (0.004 mol) of 1N methanesulfonic acid in EtOH, and chilled. The resulting precipitate was collected and dried to give 1.8 g of product as the methanesulfonic acid salt, mp 240°–244° C.

Dissolution of 1.0 g of the product in EtOH followed by treatment with an excess of i-PrOH saturated with gaseous HCl provided 0.8 g of the product as the hydrochloride salt, mp 275° C. dec.

1-Chloro-7-methoxy-4-nitro-9H-thioxanthen-9-one is prepared as follows:

Route A

A solution of 27.6 g (0.16 mol) of 2-amino-5-methoxybenzoic acid [N. B. Chapman, G. M. Gibson, and F. G. Mann, *J. Chem. Soc.*, 890 (1947)], 16.0 ml (0.38 mol) of 50% aqueous NaOH, 220 ml of $H_2O$, and 11.4 g (0.16 mol) of $NaNO_2$ was added slowly to a mixture of 50 ml of concentrated HCl and 65 g of ice chips which had been previously cooled in a salt-ice bath to −5° C. Good stirring was maintained throughout the addition and the temperature was kept below 5° C. After the addition was complete, the mixture was stirred at 0° C. for one hour, neutralized (pH 5.1) with potassium acetate, and added while cold in a thin stream to an 80° C. solution of 76.9 g (0.48 mol) of potassium ethyl xanthate in 275 ml of $H_2O$ under $N_2$. Copious $N_2$ evolution (foaming) occurred during the addition, and heat was applied as needed to maintain the temperature at 75°–80° C. The reaction mixture, under $N_2$, was cooled to 20° C. and acidified (pH 3) with concentrated HCl. The mixture was treated with 200 ml of $CH_2Cl_2$, shaken, and filtered to remove an insoluble solid. The layers were separated and the aqueous phase was extracted with a second 200 ml portion of $CH_2Cl_2$, keeping contact with air to a minimum. The extracts were combined, dried under $N_2$ ($MgSO_4$), and concentrated in vacuo to dryness.

The crude 5-methoxy-2-thiobenzoic acid was immediately dissolved in 140 ml of hot anhydrous EtOH and added to a premixed, 25° C. mixture of 31.7 g (0.16 mol) of 2,4-dichloronitrobenzene in sodium ethoxide [7.6 g (0.33 g-atom) of sodium spheres dissolved in 330 ml of anhydrous EtOH]. The resulting suspension was heated under reflux for one hour, concentrated to dryness in vacuo and taken up in 400 ml of ether and 1 l of $H_2O$. The layers were separated and the aqueous layer was extracted twice with ether to remove organic soluble impurities and made acidic (pH 1) with concentrated HCl. The solid which formed was collected, dried, and recrystallized from EtOH to give, in two crops, 19.8 g of 2-[(5-chloro-2-nitrophenyl)-thio]-5-methoxybenzoic acid, mp 184°–186° C.

A mixture of 17.6 g (0.058 mol) of the above benzoic acid, 90 ml of toluene, and 4.6 ml (0.064 mol) of thionyl chloride was heated under reflux for two hours, concentrated to dryness in vacuo, and dissolved in 140 ml of nitrobenzene. The solution was treated portionwise with 7.7 g (0.058 mol) of $AlCl_3$, keeping the temperature below 35° C. during the addition. The mixture was stirred at room temperature for 20 hours and poured into 800 ml of ice-cold $H_2O$. The mixture was stirred for one hour and the $H_2O$ was decanted from the tarry residue. The mass was washed with $H_2O$ and triturated in boiling MeOH to give 8.2 g of product, mp 235°–238° C. Other 1-chloro-4-nitro-9H-thioxanthen-9-ones containing an alkoxy or benzyloxy substituent at positions 5, 6, 7, or 8 may be prepared in an analogous manner starting from appropriately substituted benzoic acids.

Route B

An ice-cooled suspension of 3.0 g (0.125 mol) of oil-free sodium hydride in 100 ml of tetrahydrofuran was treated portionwise during ten minutes with 12.2 g (0.052 mol) of 2,6-dichloro-3-nitrobenzoic acid [Lehmstedt and Schrader, Ber. 70B, 1526 (1937)]. After stirring for ten minutes, the suspension was treated dropwise with 7.0 g (0.05 mol) of 4-methoxybenzenethiol [C. M. Suter and H. L. Hansen, *J. Am. Chem. Soc.*, 54, 4100 (1934)] in 50 ml of tetrahydrofuran. After stirring for 30 minutes at 0° C., the cooling bath was removed and the mixture was maintained at 25° C. for 12 hours. The mixture was acidified with 150 ml of 10% aqueous HCl, then treated with 200 ml of ethyl acetate. The organic layer was separated and the aqueous phase was extracted with 100 ml of ethyl acetate. The combined organic phases were dried ($MgSO_4$), and concentrated to a yellow solid which was purified by flash chromatography on silica gel, utilizing dichloromethane:methanol (8:1) as eluting solvent, to give 11.9 g of 6-chloro-2-[(4-methoxyphenyl)thio]-3-nitrobenzoic acid, mp 154°–157° C., following crystallization from toluene.

A mixture of 10.2 g (0.03 mol) of the above benzoic acid, 360 ml of trifluoroacetic acid, and 180 ml of trifluoroacetic anhydride was stirred at room temperature for 12 hours. The solution was concentrated and the residual solid was triturated from methanol to give 9.2 g of product, mp 234°–237° C. Other 1-chloro-4-nitro-9H-thioxanthen-9-ones containing an alkoxy or benzyloxy substituent at positions 5,6,7, or 8 may be prepared in an analogous manner starting from appropriately substituted benzenethiols.

EXAMPLE 59

N,N-Diethyl-5-nitro-9-phenylmethoxy-2H[1]benzothiopyrano[4,3,2-cd]indazole-2-ethanamine A mixture of 1.2 g (0.0091 mol) of 2-(diethylaminoethyl)hydrazine, 2.7 g (0.0069 mol) of 1-chloro-4-nitro-7-phenylmethoxy-9H-thioxanthen-9-one, and 0.97 g (0.0069 mol) of powdered $K_2CO_3$ in 30 ml of xylene was reacted and 2.0 g of the product was isolated as described in Example 58.

Other 9-(methoxy, phenylmethoxy, or p-halo- or p-methoxy-substituted phenylmethoxy)-5-nitro-2-(substituted)-2H[1]benzothiopyrano[4,3,2-cd]indazoles are prepared in the manner of Examples 33 through 35, 53, 58, and 59.

EXAMPLE 60

5-Amino-N,N-diethyl-9-methoxy-2H[1]-benzothiopyrano[4,3,2-cd]indazole-2-ethanamine 3.0 g of N,N-diethyl-9-methoxy-5-nitro-2H[1]-benzothiopyrano[4,3,2-cd]indazole-2-ethanamine was hydrogenated and the product was isolated as described in Example 36 to give 1.8 g of product, mp 152°–153° C.

Other 5-amino-9-methoxy-2-(substituted)-2H[1]-benzothiopyrano[4,3,2-cd]indazoles are prepared from the appropriate 9-methoxy-2-(substituted)-5-nitro-2H[1]benzothiopyrano[4,3,2-cd]indazoles in the manner of Example 36.

EXAMPLE 61

5-Amino-N,N-diethyl-9-phenylmethoxy-2H[1]benzothiopyrano[4,3,2-cd]indazole-2-ethanamine A mixture of 0.47 g (0.001 mol) of N,N-diethyl-5-nitro-9-phenylmethoxy-2H[1]benzothiopyrano[4,3,2-cd]indazole-2-ethanamine, 0.5 of Raney nickel, and 100 ml of MeOH was hydrogenated in a Parr shaker at 25° C. and an initial pressure of 50.0 psi. The mixture was filtered and the filtrate was concentrated to dryness. Crystallization of the residue from the appropriate solvent furnished the product.

Other 5-amino-9-(phenyl or substituted phenyl)-methoxy-2-(substituted)-2H[1]benzothiopyrano[4,3,2-cd]indazoles are prepared from the appropriate 5-nitro-9-phenylmethoxy-2-(substituted)-2H[1]benzothiopyrano[4,3,2-cd]indazoles in the manner of Example 61.

EXAMPLE 62

3-[2-[[2-[2-(Diethylamino)ethyl]-9-methoxy-2H[1]-benzothiopyrano[4,3,2-cd]indazol-5-yl]amino]ethyl]-2-oxazolidinone A mixture of 16.0 g (0.043 mol) 5-amino-N,N-diethyl-9-methoxy-2H[1]benzothiopyrano[4,3,2-cd]indazole-2-ethanamine and 32.0 g (0.21 mol) of 3-(β-chloroethyl)-2-oxazolidinone was reacted and the product was isolated to furnish 15.2 g, mp 135°–138° C. The reaction was as described in Example 42, with the following exception: The reaction was run at 100° C. for 13 hours instead of 150° C. for 2 hours.

The product was dissolved in a minimum amount of hot EtOH and treated with i-PrOH saturated with gaseous HCl until precipitation was complete. The solid was collected and recrystallized from EtOH to give 1.1 g of the product as the hydrochloride salt, mp 212° C. dec.

Other 7-, 8-, 9-, 10-(methoxy, phenylmethoxy, p-halo or p-methoxy substituted phenylmethoxy)-5-(monoalkylated or acylated)-2-(substituted)-2H[1]-benzothiopyrano-[4,3,2-cd]indazoles are prepared in the manner of Examples 37 through 43, with the exception of those compounds which contain side chains with reactive groups such as NH, $NH_2$, or OH. In such cases, the reactive groups must first be protected as described in Examples 44 through 46.

These derivatized compounds are in turn reduced to the 5-amino compounds as described in Example 36, except when benzyl group(s) are used as the protecting group(s). In this instance, the reductions are carried out in MeOH, THF, or MeOH/THF mixtures using Raney nickel as the catalyst. The 5-amino compounds are then derivatized in the manner of Examples 37, 39, 40, 41, 42, and 47 to provide 7-, 8-, 9-, 10-(methoxy, phenylmethoxy, or p-halo- or p-methoxy-substituted phenylmethoxy)-5-(monoalkylated or acylated)-2-(substituted)-2H[1]-benzothiopyrano[4,3,2-cd]-indazoles.

7-, 8-, 9-, 10-(Methoxy, phenylmethoxy, or p-halo- or p-methoxy-substituted phenylmethoxy)-5-(monoalkylated or acylated-2-(substituted)-2H[1]benzothiopyrano[4,3,2-cd]indazoles may be acylated at $N_5$ in the manner of Example 51 and the acyl derivatives reduced using $LiAlH_4$ in the manner of Example 52 to provide 7-, 8-, 9-, 10-(methoxy, phenylmethoxy, or p-halo- or p-methoxy-substituted phenylmethoxy)-5-(disubstituted amino)-2-(substituted)-2H[1]benzothiopyrano[4,3,2-cd]indazoles.

EXAMPLE 63

2-[[2-[[2-[2-(Diethylamino)ethyl]-9-methoxy-2H[1]benzothiopyrano[4,3,2-cd]indazol-5-yl]amino]ethyl]amino]ethanol A mixture of 8.0 g (0.017 mol) of 3-[2-[[2[2-(diethylamino)ethyl]-9-methoxy-2H[1]benzothiopyrano-[4,3,2-cd]indazol-5-yl]amino]ethyl]-2-oxazolidinone, 70 ml of 2N KOH in MeOH, 35 ml of THF, and 35 ml of $H_2O$ was treated and the product isolated as described in Example 56 to furnish 6.4 g of the product, mp 111°–115° C.

EXAMPLE 64

5-Amino-2-[2-(diethylamino)ethyl]-2H[1]benzothiopyrano[4,3,2-cd]indazol-9-ol

A mixture of 2.0 g (0.0054 mol) of 5-amino-N,N-diethyl-9-methoxy-2H[1]benzothiopyrano[4,3,2-cd]indazole-2-ethanamine and 40 ml of 48% HBr was heated at 130° C. under inert atmosphere ($N_2$) for three hours, allowed to cool to room temperature, and poured into 200 ml of $H_2O$. The mixture was made strongly basic with 50% aqueous NaOH. The pH was then adjusted to 8.5 with 2N HCl and the gum that formed was triturated successively with $CH_2Cl_2$, $Et_2O$, and $H_2O$, and recrystallized from EtOH to give 1.2 g of the product, mp 224°–232° C.

The product (1.2 g) was dissolved in a minimum amount of hot EtOH and treated with i-PrOH saturated with gaseous HCl until precipitation was complete. The solid was collected and recrystallized from EtOH to give 1.2 g of the product as the hydrochloride salt, mp 279° C. dec.

Other 2,5-(disubstituted)-2H[1]benzothiopyrano[4,3,2-cd]indazole-9-ols are prepared from the corresponding 9-methoxy precursors in the manner of Example 64.

EXAMPLE 65

2-[2-(Diethylamino)ethyl]-5-[[2-[(2-hydroxyethyl)-amino]ethyl]amino]-2H[1]benzothiopyrano[4,3,2-cd]-indazol-9-ol, hydrochloride salt A mixture of 5.0 g (0.0094 mol) of 2-[[2-[[2-[2-(diethylamino)ethyl]-9-phenylmethoxy-2H[1]benzothiopyrano[4,3,2-cd]indazol-5-yl]amino]ethyl]amino]ethanol, 0.2 g of 20% Pd/C, and 100 ml of HOAc was hydrogenated in a Parr shaker at 25° C. and an initial pressure of 50 psi. The mixture was filtered and the filtrate was concentrated in vacuo to a small volume, treated with 300 ml of H$_2$O, and the pH was adjusted to 6.5 with 50% aqueous NaOH. The mixture was extracted three times with CHCl$_3$ and the extracts were combined, dried (MgSO$_4$), and concentrated in vacuo to dryness. The residue was dissolved in a minimum amount of EtOH and treated with i-PrOH until precipitation was complete. The solid was collected and recrystallized to give the product.

Other 2,5-(disubstituted)-2H[1]benzothiopyrano[4,3,2-cd]indazol-7,8,9 or 10-ols are prepared from the corresponding 7,8,9 or 10-(phenyl and substituted phenyl)-methoxy precursors in the manner of Example 65.

EXAMPLE 66

3-[2-[[2-[2-(diethylamino)ethyl]-9-hydroxy-2H-[1]-benzothiopyrano[4,3,2-cd]indazol-5-yl]amino]ethyl]-2-oxazolidinone A mixture of 3.5 g (0.0075 mol) of 3-[2-[[2-[2-(diethylamino)ethyl]-9-methoxy-2H[1]benzothiopyrano[4,3,2-cd]indazol-5-yl]amino]ethyl]-2-oxazolidinone and 15 ml of a one molar solution of boron tribromide in dichloromethane was heated at reflux for 15 minutes. The suspension was cooled and poured into saturated aqueous sodium bicarbonate. The aqueous mixture was extracted with a mixture of dichloromethane:methanol (4:1). The organic phase was washed with brine, dried (Na$_2$SO$_4$), and evaporated to a residue that was triturated with 2-propanol to give 2.6 g of product.

0.5 grams of the product was dissolved in a minimum amount of hot EtOH and treated with 2-PrOH saturated with HCl until precipitation was complete. The solid was collected and dried at 65° C. to give 0.7 g of the product as the hydrochloride salt, mp 223°–226° C. (decomposition).

Other 2,5-(disubstituted)-2H[1]benzothiopyrano[4,3,2-cd]indazole-9-ols are prepared from the corresponding 9-methoxy precursors in the manner of Example 66.

EXAMPLE 67

2-[2-(Diethylamino)ethyl]-5-[[2-[(2-hydroxyethyl)-aminoethyl]amino-2H-[1]benzothiopyrano[4,3,2-cd]-indazol-9-ol A solution of 2.0 g (0.0043 mol) of 3-[2-[[2-[2-(diethylamino)ethyl]-9-hydroxy-2H-[1]benzothiopyrano[4,3,2-cd]indazol-5-yl]amino]ethyl]-2-oxazolidinone and 100 ml of 2N KOH in MeOH was heated at reflux for 18 hours and isolated as described in Example 48 to give the crude product. Chromatography over silica gel utilizing 3:1 ethyl acetate:MeOH as eluant gave 0.9 g of pure product. Salt formation as described in Example 66 gave 0.9 g of the product as the hydrochloride salt, mp 224°–234° C. (decomposition).

EXAMPLE 68

N,N-Diethyl-7-methoxy-5-nitro-2H[1]benzothiopyrano[4,3,2-cd]indazole-2-ethanamine Reaction of a mixture of 1.8 g (0.0137 mol) of 2-(diethylaminoethyl)hydrazine, 3.0 g (0.0093 mol) of 1-chloro-5-methoxy-4-nitro-9H-thioxanthen-9-one in 80 ml of DMF as described in Example 53 gave 2.7 g of product.

1-Chloro-5-methoxy-4-nitro-9H-thioxanthen-9-one is prepared from 2-methoxybenzenethiol [L. Gottermann, Ber. 32, 1136 (1899)] in the manner of Example 58.

Other 7-(methoxy, phenylmethoxy, or p-halo- or p-methoxy-substituted phenylmethoxy)-5-nitro-2-(substituted)-2H[1]benzothiopyrano[4,3,2-cd]indazoles are prepared in the manner of Example 33 to 35, 53, 58, and 68.

EXAMPLE 69

5-Amino-N,N-diethyl-7-methoxy-2H[1]benzothiopyrano-[4,3,2-cd]indazole-2-ethanamine Hydrogenation of N,N-diethyl-7-methoxy-5-nitro-2H[1]benzothiopyrano[4,3,2-cd]indazole-2-ethanamine as described in Example 36 gave the product.

Other 5-amino-7-methoxy-2-(substituted)-2H[1]-benzothiopyrano[4,3,2-cd]indazoles are prepared from the appropriate 7-methoxy-2-(substituted)-5-nitro-2H-[1]benzothiopyrano[4,3,2-cd]indazoles in the manner of Example 36.

EXAMPLE 70

N-[2-[2-(Diethylamino)ethyl]-7-methoxy-2H[1]benzothiopyrano[4,3,2-cd]indazol-5-yl]-1,2-ethanediamine, hydrobromide salt Reaction of a solution of 3.5 g (0.0095 mol) of 5-amino-N,N-diethyl-7-methoxy-2H[1]benzothiopyrano-[4,3,2-cd]indazole-2-ethanamine and 5.8 g (0.0283 mol) of 2-bromoethylamine, hyrobromide, in 30 ml of EtOH as described in Example 38 gave 1.6 g of product.

EXAMPLE 71

5-[2-(Aminoethyl)amino]-2-[2-(diethylamino)ethyl]-2H-[1]benzothiopyrano[4,3,2-cd]indazol-7-ol, hydrobromide salt Reaction of a suspension of 2.3 g (0.0047 mol) of N-[2-[2-(diethylamino)ethyl-7-methoxy-2H[1]benzothiopyrano[4,3,2-cd]indazol-5-yl]-1,2-ethanediamine, hydrobromide salt, and excess boron tribromide in ethylene dichloride as described in Example 57 gave 2.4 g of product.

Other 2,5-(disubstituted)-2H[1]benzothiopyrano[4,3,2-cd]indazole-7-ols are prepared from the corresponding 7-methoxy precursors in the manner of Example 57.

EXAMPLE 72

5-Amino-2-[2-(diethylamino)ethyl]-2H[1]benzothiopyrano[4,3,2-cd]indazol-7-ol

Reaction of 5-amino-N,N-diethyl-7-methoxy-2H[1]benzothiopyrano[4,3,2-cd]indazole-2-ethanamine with 48% HBr as described in Example 64 gave the product.

Other 5-amino-2-(substituted)-2H[1]benzothiopyrano[4,3,2-cd]indazol-7-ols are prepared from the

EXAMPLE 73

N,N-Diethyl-8-methoxy-5-nitro-2H[1]benzothi-opyrano-[4,3,2-cd]indazole-2-ethanamine Reaction of a mixture of 2.2 g (0.0169 mol) of 2-(diethylaminoethyl)hydrazine, 3.7 g (0.0115 mol) of 1-chloro-6-methoxy-4-nitro-9H-thioxanthen-9-one in 100 ml of DMF as described in Example 53 gave 3.4 g of product.

1-chloro-6-methoxy-4-nitro-9H-thioxanthen-9-one is prepared from 3-methoxybenzenethiol [L. Szathmary, Ber. 43, 2485 1910)] in the manner of Example 58.

Other 8-(methoxy, phenylmethoxy, or p-halo- or p-methoxy-substituted phenylmethoxy)-5-nitro-2-(substituted)-2H[1]benzothiopyrano[4,3,2-cd]indazoles are prepared in the manner of Examples 33 to 35, 53, 58, and 73.

EXAMPLE 74

5-Amino-N,N-diethyl-8-methoxy-2H[1]benzothi-opyrano-[4,3,2-cd]indazole-2-ethanamine Hydrogenation of N,N-diethyl-8-methoxy-5-nitro-2H[1]benzothiopyrano[4,3,2-cd]indazole-2-ethanamine as described in Example 36 gave the product.

Other 5-amino-8-methoxy-2-(substituted)-2H[1]-benzothiopyrano[4,3,2-cd]indazoles are prepared from the appropriate 8-methoxy-2-(substituted)-5-nitro-2H[1]benzothiopyrano[4,3,2-cd]indazoles in the manner of Example 36.

EXAMPLE 75

N-[2-[2-(Diethylamino)ethyl]-8-methoxy-2H[1]benzo-thiopyrano[4,3,2-cd]indazol-5-yl]-1,2-ethanediamine, hydrobromide salt Reaction of a solution of 4.5 g (0.0122 mol) of 5-amino-N,N-diethyl-8-methoxy-2H[1]benzothiopyrano-[4,3,2-cd]indazole-2-ethanamine and 7.5 g (0.0366 mol) of 2-bromoethylamine, hydrobromide, in 40 ml of EtOH as described in Example 38 gave 2.4 g of product.

EXAMPLE 76

5-[2-(Aminoethyl)amino]-2-[2-(diethylamino)ethyl]-2H[1]benzothiopyrano[4,3,2-cd]indazol-8-ol, hydrobromide salt Reaction of a suspension of 5.0 g (0.0102 mol) of N-[2-[2-(diethylamino)ethyl-7-methoxy-2H[1]benzothi-opyrano[4,3,2-cd]indazol-5-yl]-1,2-ethanediamine, hydrobromide salt, and excess boron tribromide in ethylene dichloride as described in Example 57 gave 4.8 g of product.

Other 2,5-(disubstituted)-2H[1]benzothi-opyrano[4,3,2-cd]indazole-8-ols are prepared from the corresponding 8-methoxy precursors in the manner of Example 57.

EXAMPLE 77

5-Amino-2-[2-(diethylamino)ethyl]-2H[1]benzothi-opyrano[4,3,2-cd]indazol-8-ol

Reaction of 5-amino-N,N-diethyl-8-methoxy-2H-[1]benzothiopyrano[4,3,2-cd]indazole-2-ethanamine with 48% HBr as described in Example 64 gave the product.

Other 5-amino-2-(substituted)-2H[1]benzothi-opyrano[4,3,2-cd]indazol-8-ols are prepared from the appropriate 5-amino-8-methoxy-2-(substituted)-2H[1]benzothiopyrano[4,3,2-cd]indazoles in the manner of Example 64.

EXAMPLE 78

N,N-Diethyl-10-methoxy-5-nitro-2H[1]benzothi-opyrano[4,3,2-cd]indazole-2-ethanamine Reaction of a mixture of 2.5 g (0.0192 mol) of 2-(diethylaminoethyl)hydrazine, 4.2 g (0.0131 mol) of 1-chloro-8-methoxy-4-nitro-9H-thioxanthen-9-one in 110 ml of DMF as described in Example 53 gave 2.7 g of product.

1-Chloro-8-methoxy-4-nitro-9H-thioxanthen-9-one is prepared in the manner of Example 58.

Other 10-(methoxy, phenylmethoxy, or p-halo- or p-methoxy-substituted phenylmethoxy)-5-nitro-2-(substituted)-2H[1]benzothiopyrano[4,3,2-cd]indazoles are prepared in the manner of Examples 33 to 335, 53, 58, and 78.

EXAMPLE 79

5-Amino-N,N-diethyl-10-methoxy-2H[1]benzothi-opyrano[4,3,2-cd]indazole-2-ethanamine Hydrogenation of N,N-diethyl-10-methoxy-5-nitro-2H[1]benzothiopyrano[4,3,2-cd]indazole-2-ethanamine as described in Example 36 gave the product.

Other 5-amino-10-methoxy-2-(substituted)-2H[1]-benzothiopyrano[4,3,2-cd]indazoles are prepared from the appropriate 10-methoxy-2-(substituted)-5-nitro-2H-[1]benzothiopyrano[4,3,2-cd]indazoles in the manner of Example 36.

EXAMPLE 80

N-[2-[2-(Diethylamino)ethyl]-10-methoxy-2H1[1]ben-zothiopyrano[4,3,2-cd]indazol-5-yl]-1,2-ethanediamine, hydrobromide salt Reaction of a solution of 3.2 g (0.0087 mol) of 5-amino-N,N-diethyl-10-methoxy-2H[1]benzothi-opyrano[4,3,2-cd]indazole-2-ethanamine and 5.3 g (0.0259 mol) of 2-bromoethylamine, hydrobromide, in 27 ml of EtOH as described in Example 38 gave 1.3 g of product.

EXAMPLE 81

5-[2-(Aminoethyl)amino]-2-[2-(diethylamino)ethyl]-2H-[1]benzothiopyrano[4,3,2-cd]indazol-10-ol, hydrobromide salt Reaction of a suspension of 1.7 g (0.0035 mol) of N-[2-[2-(diethylamino)ethyl)-10-methoxy-2H[1]-benzo-thiopyrano[4,3,2-cd]indazol-5-yl]-1,2-ethanediamine, hydrobromide salt, and excess boron tribromide in ethylene dichloride as described in Example 57 gave 1.9 g of product.

Other 2,5-(disubstituted)-2H[1]benzothi-opyrano[4,3,2-cd]indazole-10-ols are prepared from the corresponding 10-methoxy precursors in the manner of Example 57.

EXAMPLE 82

5-Amino-2-[2-(diethylamino)ethyl]2H-[1]benzothi-opyrano[4,3,2-cd]indazol-10-ol

Reaction of 5-amino-N,N-diethyl-10-methoxy-2H[1]-benzothiopyrano[4,3,2-cd]indazole-2-ethanamine with 48% HBr as described in Example 64 gave the product.

Other 5-amino-2-(substituted)-2H[1]benzothiopyrano[4,3,2-cd]indazol-10-ols are prepared from the appropriate 5-amino-10-methoxy-2-(substituted)-2H[1]-benzothiopyrano[4,3,2-cd]indazoles in the manner of Example 64.

EXAMPLE 83

N,N-Diethyl-3-methoxy-5-nitro-2H[1]benzothiopyrano[4,3,2-cd]indazole-2-ethanamine Reaction of a mixture of 4.5 g (0.0343 mol) of 2-(diethylaminoethyl)hydrazine, 7.5 g (0.0233 mol) of 1-chloro-2-methoxy-4-nitro-9H-thioxanthen-9-one in 200 ml of DMF as described in Example 53 gave 7.6 g of product. 1-Chloro-2-methoxy-4-nitro-9H-thioxanthen-9-one is prepared from 2-thiobenzoic acid and 2,4-dichloro-5-nitroanisole [C. Bloomfield, A. K. Manglik, R. B. Mootie, K. Schofield, and G. D. Tokin, J. Chem. Soc. Perkin Trans. II, 75 (1983)] in the manner of Example 58.

Other 3-(methoxy, phenylmethoxy, or p-halo- or p-methoxy-substituted phenylmethoxy)-5-nitro-2-(substituted)-2H-[1]benzothiopyrano[4,3,2-cd]indazoles are prepared in the manner of Examples 33 to 35, 53, 58, and 83.

EXAMPLE 84

5-Amino-N,N-diethyl-3-methoxy-2H[1]benzothiopyrano-[4,3,2-cd]indazole-2-ethanamine Hydrogenation of N,N-diethyl-3-methoxy-5-nitro-2H[1]benzothiopyrano[14,3,2-cd]indazole-2-ethanamine as described in Example 36 gave the product.

Other 5-amino-3-methoxy-2-(substituted)-2H[1]benzothiopyrano[4,3,2-cd]indazoles are prepared from the appropriate 3-methoxy-2-(substituted)-5-nitro-2H-[1]benzothiopyrano[4,3,2-cd]indazoles in the manner of Example 36.

EXAMPLE 85

N-[2-[2-(Diethylamino)ethyl]-3-methoxy-2H[1]benzothioapyrano[4,3,2-cd]indazol-5-yl]-1,2-ethanediamine, hydrobromide salt Reaction of a solution of 7.0 g (0.019 mol) of 5-amino-N,N-diethyl-3-methoxy-2H[1]benzothiopyrano[4,3,2-cd]indazole-2-ethanamine and 11.6 g (0.0566 mol) of 2-bromoethylamine, hydrobromide, in 60 ml of EtOH as described in Example 38, gave 3.1 g of product.

EXAMPLE 86

5-[2-(Aminoethyl)amino]-2-[2-(diethylamino)ethyl]-2H[1]benzothiopyrano[4,3,2-cd]indazol-3-ol, hydrobromide salt Reaction of a suspension of 4.2 g (0.0085 mol) of N-[2-[2-(diethylamino)ethyl-3-methoxy-2H[1]benzothiopyrano[4,3,2-cd]indazol-5-yl]-1,2-ethanediamine, hydrobromide salt, and excess boron tribromide in ethylene dichloride as described in Example 57 gave 3.9 g of product.

Other 2,5-(disubstituted)-2H[1]benzothiopyrano[4,3,2-cd]indazole-3-ols are prepared from the corresponding 3-methoxy precursors in the manner of Example 57.

EXAMPLE 87

5-Amino-2-[2-(diethylamino)ethyl]-2H-[1]benzothiopyrano[4,3,2-cd]indazol-3-ol

Reaction of 5-amino-N,N-diethyl-3-methoxy-2H[1]benzothiopyrano[4,3,2-cd]indazole-2-ethanamine with 48% HBr as described in Example 64 gave the product.

Other 5-amino-2-(substituted)-2H[1]benzothiopyrano[4,3,2-cd]indazol-3-ols are prepared from the appropriate 5-amino-3-methoxy-2-(substituted)-2H[1]benzothiopyrano[4,3,2-cd]indazoles in the manner of Example 64.

EXAMPLE 88

N,N-Diethyl-3,9-dimethoxy-5-nitro-2H[1]benzothiopyrano[4,3,2-cd]indazole-2-ethanamine Reaction of a mixture of 1.8 g (0.0137 mol) of 2-(diethylaminoethyl)hydrazine, 3.1 g (0.0093 mol) of 1-chloro-2,7-dimethoxy-4-nitro-9H-thioxanthen-9-one in 80 ml of DMF as described in Example 53 gave 2.4 g of product.

1-Chloro-2,7-dimethoxy-4-nitro-9H-thioxanthen-9-one is prepared from 5-methoxy-2-thiobenzoic acid and 2.4-dichloro-5-nitroanisole in the manner of Example 58.

Other 3.9-di-(methoxy, phenylmethoxy, or p-halo- or p-methoxy-substituted phenylmethoxy)-5-nitro-2-(substituted)-2H[1]benzothiopyrano[4,3,2-cd]indazoles are prepared in the manner of Examples 33 to 35, 53, 58, and 88.

EXAMPLE 89

5-Amino-N,N-diethyl-3,9-dimethoxy-2H[1]benzothiopyrano[4,3,2-cd]indazole-2-ethanamine Hydrogenation of N,N-diethyl-3,9-dimethoxy-5-nitro-2H[1]benzothiopyrano[4,3,2-cd]indazole-2-ethanamine as described in Example 36 gave the product.

Other 5-amino-3,9-dimethoxy-2-(substituted)-2H[1]benzothiopyrano[4,3,2-cd]indazoles are prepared from the appropriate -3,9-dimethoxy-2-(substituted)-5-nitro-2H[1]benzothiopyrano[4,3,2-cd]indazoles in the manner of Example 36.

EXAMPLE 90

N-[2-[2-(Diethylamino)ethyl]-3,9-dimethoxy-2H[1]benzothiopyrano[4,3,2-cd]indazol-5-yl]-1,2-ethanediamine, hydrobromide salt Reaction of a solution of 3.6 g (0.0095 mol) of 5-amino-N,N-diethyl-3,9-dimethoxy-2H[1]benzothiopyrano[4,3,2-cd]indazole-2-ethanamine and 5.8 g (0.0283 mol) of 2-bromoethylamine, hydrobromide, in 30 ml of EtOH as described in Example 38 gave 1.8 g of product.

EXAMPLE 91

5-[2-(Aminoethyl)amino]-2-[2-(diethylamino)ethyl]2H[1]benzothiopyrano[4,3,2-cd]indazol-3,9-diol, hydrobromide salt Reaction of a suspension of 2.4 g (0.0047 mol) of N-[2-[2-(diethylamino)ethyl-3,9-dimethoxy-2H[1]-benzothiopyrano[4,3,2-cd]indazol-5-yl]-1,2-ethanediamine, hydrobromide salt, and excess boron tribromide in ethylene dichloride as described in Example 57 gave 2.2 g of product.

Other 2,5-(disubstituted)-2H[1]benzothiopyrano[4,3,2-cd]indazole-3,9-diols are prepared from the corresponding 3,9-dimethoxy precursors in the manner of Example 57.

EXAMPLE 92

5-Amino-2-[2-(diethylamino)ethyl]-2H[1]benzothiopyrano[4,3,2-cd]indazol-3,9-diol Reaction of 5-amino-N,N-diethyl-3,9-dimethoxy-2H[1]benzothiopyrano[4,3,2-cd]indazole-2-ethanamine with 48% HBr as described in Example 64 gave the product.

Other 5-amino-2-(substituted)-2H[1]benzothiopyrano[4,3,2-cd]indazol-3,9-diols are prepared from the appropriate 5-amino-3,9-dimethoxy-2-(substituted)-2H[1]benzothiopyrano[4,3,2-cd]indazoles in the manner of Example 64.

EXAMPLE 93

1-Chloro-7-hydroxy-4-nitro-9H-thioxanthen-9-one

A mixture of 25 g of 1-chloro-7-methoxy-4-nitro-9H-thioxanthen-9-one, 32.1 g of anhydrous aluminum chloride, and 300 ml of 1,2-dichloroethane is heated under reflux for 1.5 hours. The mixture is concentrated, then treated with 640 ml of concentrated HCl. After 1 hour, the slurry is filtered, and then washed with 500 ml of water followed by 300 ml of 2-propanol, to afford the title compound as a gold solid, mp>300° C.

1-Chloro-7-methoxy-4-nitro-9H-thioxanthen-9-one is prepared according to Example 58.

EXAMPLE 94

2-[2-(Diethylamino)ethyl]-5-nitro-2H-[1]benzothiopyrano[4,3,2-cd]indazol-9-ol, methanesulfonate A mixture of 23.9 g of 1-chloro-7-hydroxy-4-nitro-9H-thioxanthen-9-one, 131.22 g of [2-(diethylamino)ethyl)-hydrazine, 13.6 ml of N,N-diisopropylethylamine and 450 ml of dimethylformamide is stirred at room temperature for 3 hours, and then evaporated to dryness.

The residue is triturated with 2-propanol, then filtered to afford the title compound as the free base, mp 284° C. (dec.). The methanesulfonate salt, mp 152°-155° C., crystallizes from methanolic solution containing the free base and 1.25 equivalents of methanesulfonic acid.

EXAMPLE 95

2-[2-(Diethylamino)ethyl]-5-[[2-(1,3-dihydro-1,3-dioxo-2H-isoindol-2-yl)ethyl]amino]-2H-[1]benzothiopyrano[4,3,2-cd]indazol-9-ol, monohydrobromide A mixture of 4.61 g of 5-amino-2-[2-(diethylamino)-ethyl]-2H-benzothiopyrano[4,3,2-cd]indazol-9-ol and 4.3 g of bromoethylphthalimide is heated at 110° C. for 16 hours, then cooled to room tempaerature. The mixture is combined with 300 ml of chloroform and 10 ml of N,N-diisopropylethylamine and heated under reflux for 2 hours, then washed with three 350-ml portions of water. The solution is evaporated to afford an oily solid which is triturated with 2-propanol. The resulting solid is collected and dried to give the title compound, mp 163°-166° C.

5-Amino-2-[2-(diethylamino)ethyl]-2H-[1]benzothiopyrano[4,3,2-cd]indazol-9-ol is prepared by hydrogenation of the corresponding 5-nitro compound as described in Example 36.

EXAMPLE 96

5-[(2-Aminoethyl)amino]-2-[2-(diethylamino)ethyl]-2H-[1]benzothiopyrano[4,3,2-cd]indazol-9-ol, trihydrochloride A mixture of 2.4 g of 2-[2-(diethylamino)ethyl]-5-[[2-(1,3-dihydro-1,3-dioxo-2H-isoindol-2-yl)ethyl]amino]-2H-[1]benzothiopyrano[4,3,2-cd]-indazol-9-ol, monohydrobromide, 5.25 ml of methylhydrazine, and 100 ml of methanol are stirred for 16 hours and then evaporated to dryness to afford the title compound as the free base.

The trihydrochloride salt, mp 260° C. (dec.), was crystallized from a methanolic solution containing the free base and three equivalents of hydrochloric acid.

EXAMPLE 96A

N-[2-[2-(Diethylamino)ethyl]-2H-[1]benzothiopyrano-[4,3,2-cd]indazol-5-yl]-1,3-dihydro-1,3-dioxo-2H-isoindol-2-acetamide, monohydrochloride A mixture of 5 g of 5-amino-N,N-diethyl-2H[1]benzothiopyrano[4,3,2-cd]indazole-2-ethanamine dihydrochloride, 4.125 g of N-phthaloylglycine acid chloride, 0.180 g of 2,6-dimethylaminopyridine, and 75 ml of pyridine were heated to 55° C. for 24 hours, then poured into 275 ml of saturated aqueous sodium bicarbonate solution. The mixture was filtered, and the resulting solid was washed with 150 ml of 3% aqueous sodium bicarbonate solution, affording the title compound, mp 176°-178° C.

EXAMPLE 96B

2-Amino-N-[2-[2-(diethylamino)ethyl]-2H-[1]benzothiopyrano[4,3,2-cd]indazol-5-yl]acetamide, dihydrochloride A mixture of 3 g of N-[2-[2-(Diethylamino)ethyl]-2H-[1]benzothiopyrano[4,3,2-cd]indazol-5-yl]-1,3-dihydro-1,3-dioxo-2H-isoindol-2-acetamide, monohydrochloride, prepared as described in Example 96A, 0.784 ml of 54% aqueous hydrazine, and 40 ml of methanol was stirred for 2 days. The solution was then evaporated to dryness and the residue was diluted with water and extracted three times with 35-ml portions of ethyl acetate. The combined extracts were washed with 25 ml of saturated aqueous sodium carbonate solution and then dried over anhydrous magnesium sulfate. The ethyl acetate solutions were evaporated to afford the title compound as the free base. The dihydrochloride salt crystallizes from a methanolic solution of the free base upon acidification with 2.25 equivalents of hydrochloric acid.

PREPARATION OF STARTING MATERIALS

EXAMPLE 97

1-Chloro-4-nitro-9H-selenoxanthen-9-one

A stirred solution of 32 g of phosphorus pentoxide and 320 g of methanesulfonic acid at 80° C. is treated with 16 g (0.045 mole) of 2-[(5-chloro-2-nitrophenyl)-seleno]benzoic acid. The mixture is stirred at 80° C. for two hours, cooled to 25° C., and poured into 900 ml of chilled water. The suspension is stirred for 30 minutes and the solids are collected by filtration, then washed sequentially with water, 5% aqueous sodium bicarbonate, and 2-propanol to give 6.2 g of the dried product; mp 189°-190° C.

Alternatively, 1-chloro-4-nitro-9H-selenoxanthen-9-one may be prepared as follows:

A suspension of 140 g of phosphorus pentoxide in 700 ml of dichloromethane is refluxed with 350 ml of hexamethyldisiloxane for two hours. The solution is concentrated in vacuo to a clear colorless syrup.

A mixture of 125 g of the syrup and 15.5 g of additional phosphorus pentoxide is heated at 210° C. To this mechanically stirred suspension is added 4.75 g (0.016 mole) of 2-[(5-chloro-2-nitrophenylseleno]benzoic acid. After 15 minutes, the reaction is cooled to 25° C. and poured into ice cold 6N aqueous hydrochloric acid. After stirring for one hour, the gold solid is collected and dried in vacuo at 70° C. for 13 hours to give 4.47 g of dried product; mp 196°–197° C.

2-[(5-Chloro-2-nitrophenyl)seleno]benzoic acid is prepared as follows:

A stirred mixture of 20 g (0.088 mole) of 2-selenocyanobenzoic acid and 300 ml of ethanol under argon at 0° C. is treated portionwise with 13.5 g (0.36 mole) of sodium borohydride. The mixture is stirred at 25° C. for 40 minutes and treated dropwise with a solution of 17 g (0.089 mole) of 2,4-dichloronitrobenzene in 50 ml of ethanol. The mixture is heated under reflux for 15 hours, cooled to 0° C., treated with 1.7 g (0.045 mole) of additional sodium borohydride, and refluxed another two hours. The cooled mixture is acidified with one normal aqueous hydrochloric acid, then extracted with ethyl acetate. The combined extracts are concentrated to a solid residue whose crystallization from acetonitrile gives 26.3 g of product; mp 226°–228° C.

2-Selenocyanobenzoic acid is prepared as follows:

A mixture of 54.7 g (0.25 mole) of 2-bromobenzoic acid, sodium salt, 105 ml of a 2.36 molar solution of sodium selenocyanate in N,N-dimethylacetamide [*J. Org. Chem.*, 43, 1689 (1978)], 200 mg of copper powder, and 50 ml of N,N-dimethylacetamide is heated under nitrogen at 150° C. for four hours. The hot solution is poured into 450 ml of ice water. The aqueous mixture is acidified with 30 ml of concentrated hydrochloric acid then extracted three times with 100 ml portions of dichloromethane. The combined extracts are clarified with charcoal then stirred for four hours under nitrogen with a solution of 28 g of sodium bicarbonate in 300 ml of water. The aqueous layer is clarified with charcoal, cooled, and acidified with 28 ml of concentrated hydrochloric acid. The solids are collected, washed with ice-cold water, and dried to give 38.6 g of the product; mp 170°–174° C.

EXAMPLE 98

1-Chloro-7-methoxy-4-nitro-9H-selenoxanthen-9-one

A mixture of 200 g of the hexamethyldisiloxane/phosphorus pentoxide syrup and 24 g of additional phosphorus pentoxide is heated to 210° C. To this mechanically stirred suspension is added 6.0 g (0.015 mole) of 2-[(5-chloro-2-nitrophenyl)seleno]-5-methoxybenzoic acid, hydrochloride. After 20 minutes, the reaction is cooled to 25° C. and poured over ice. After stirring for three hours, the orange solid is collected on a Celite ® pad. The product with the Celite ® pad is stirred in ethyl acetate at 25° C. for 13 hours. The mixture is filtered and the Celite ® washed with hot ethyl acetate. The filtrate is concentrated to a bright orange solid whose recrystallization from acetonitrile gives 3.58 g of dried product; mp 222°–224° C.

2-[(5-Chloro-2-nitrophenyl)seleno]-5-methoxy benzoic acid, hydrochloride is prepared as follows:

A stirred mixture of 7.68 g (0.030 mole) of 2-selenocyano-5-methoxybenzoic acid and 6.90 g (0.036 mole) of 2,4-dichloronitrobenzene in 290 ml of ethanol under an argon atmosphere at 0° C. is treated portionwise with 3.42 g (0.090 mole) of sodium borohydride. After the addition is complete, the reaction is warmed to 25° C. The mixture is heated under reflux for 18 hours, cooled, acidified with 1N aqueous hydrochloric acid, and then extracted into ethyl acetate. The extracts are concentrated to 9.8 g of analytically pure product as a salt with 0.10 equivalents of hydrogen chloride and solvated with 0.13 equivalents of water; mp 194°–196° C.

2-Selenocyano-5-methoxybenzoic acid is prepared as follows:

A mixture of 15.0 g (0.059 mole) of 2-bromo-5-methoxybenzoic acid, (*J. Amer. Chem. Soc.* 68, 1599 [1946]) sodium salt, 225 ml of N,N-dimethylacetamide, 11.10 g (0.077 mole) of potassium selenocyanate, and 0.75 g of copper powder is heated under argon at 150° C. for four hours. The reaction is cooled, poured onto crushed ice, and acidified with 25 ml of concentrated hydrochloric acid. the precipitate is collected and slurried with a 5 to 1 (v/v) mixture of dichloromethane and tetrahydrofuran. The mixture is stirred overnight with charcoal. Filtration through a Celite ® pad gives a pale yellow filtrate to which is added a solution of 14 g of sodium bicarbonate in 150 ml of water. After stirring under an argon atmosphere for sevral hours, the organic layer is separated and extracted once with saturated aqueous sodium bicarbonate solution. The combined aqueous solutions are cooled with crushed ice and acidified with concentrated hydrochloric acid. The solids are collected, washed with cold water, and dried to give 7.71 g of the product; mp 183°–186° C. (dec.).

EXAMPLE 99

1-Chloro-6-hydroxy-4-nitro-9H-selenoxanthen-9-one

Aluminium chloride (anhydrous powder, 2.34 g) is added to a suspension of 2.16 g (0.006 mole) 1-chloro-6-methoxy-4-nitro-9H-selenoxanthen-9-one in 25 ml of 1,2-dichloroethane. The mixture is heated at 75° C. for 1.5 hours, then concentrated in vacuo. The residue is treated with 50 ml of concentrated hydrochloric acid at 25° C. for six hours. The solids are collected, washed with water, and dried in vacuo to give 1.73 g of product solvated with 0.74 equivalents of water. The product so obtained is sufficiently pure for further reaction.

1-Chloro-6-methoxy-4-nitro-9H-selenoxanthen-9-one, mp 229-232 (dec) is prepared in a manner analogous to that described for the preparation of 1-chloro-7-methoxy-4-nitro-9H-selenoxanthen-9-one. The requisite 2-[(5-chloro-2-nitrophenyl)seleno-4-methoxy benzoic acid is similarly obtained by coupling 2-selenocyano 4-methoxybenzoic acid and 2,4-dichloronitrobenzene. By treating 30.0 g of 2-iodo-4-methoxybenzoic acid [*Coll. Czech. Chem. Comm.*, 39 3548 (1974)] with potassium selenocyanate there is obtained 21.13 g of 2-selenocyano-4-methoxybenzoic acid, mp 225°–228° C. (decarboxylation).

1-(2-Hydrozinoethyl)pyrrolidine

A mixture of 200 g of 85% hydrazine hydrate, 200 ml of water, 170 g of N-chloroethylpyrrolidine hydrochloride, and 70 g of potassium carbonate was boiled under reflux for seven hours. Sodium hydroxide (390 g) was added and the mixture was extracted with ether. The ethereal extract, dried and distilled, yielded the title compound, bp 107°–111° (18.5 mm).

EXAMPLE 100

N,N-Diethyl-5-nitro-2H-[1]benzoselenino[4,3,2-cd]-indazole-2-ethanamine

An ice-cold solution of 6.2 g (0.018 mole) of 1-chloro-4-nitro-9H-selenoxanthen-9-one, 90 ml of N,N-dimethylformamide and 9.6 ml of diisopropyl ethylamine is treated dropwise during five minutes with 3.3 g (0.032 mole) of 2-(diethylaminoethyl)-hydrazine [J. Med. Chem., 7, 493 (1964)]. The cooling bath is removed after ten minutes and the mixture is stirred at 25° C. for 30 minutes. Concentration of the mixture in vacuo leaves an orange solid that is triturated with hot 2-propanol to give 7.0 g of the dried product as a salt with 0.7 equivalents of hydrogen chloride and solvated with 0.2 equivalent of water; mp 246°-248° C.

EXAMPLE 101

5-Amino-N,N-diethyl-2H-[1]benzoselenino[4,3,2-cd]-indazole-2-ethanamine

A mixture of 1.5 g (0.003 mole) of N,N-diethyl-5-nitro-2H[1]benzoselenino[4,3,2-cd]indazole-2-ethanamine, hydrochloride, 60 mg of 20% palladium on carbon, and 9 ml of acetic acid is hydrogenated at atmospheric pressure for 18 hours. The mixture is filtered and concentrated in vacuo to give a solid residue. Dissolution in a solution of hydrogen chloride in 2-propanol gives 1.4 g of the dried product as a salt with 2.0 equivalents of hydrogen chloride and solvated with 0.4 equivalent of water and 0.6 equivalent of 2-propanol; mp 262°-264° C. (dec.).

EXAMPLE 102

N-[2-[2-(diethylamino)ethyl]-2H-[1]-benzoselenino[4,3,2-cd]indazol-5-yl]-1,2-ethanediamine A mixture of 3.7 g (0.01 mole) of 5-amino-N,N-diethyl-2H[1]benzoselenino[4,3,2-cd]indazole-2-ethanamine, 5.9 g (0.029 mole) of 2-bromoethylamine, hydrobromide, and 25 ml of ethanol is heated under reflux for ten hours. Additional 2-bromoethylamine, hydrobromide (2.0 g) is added and the solution is heated at reflux for 38 hours, then allowed to cool to 25° C. The solids are collected and washed with cold ethanol to give 3.5 g of the dried product as a salt with 2.8 equivalents of hydrogen bromide; mp 268°-270° C. (dec.).

EXAMPLE 103

N,N-diethyl-5-[[2-(diethylamino)ethyl]amino]-2H-[1]-benzoselenino[4,3,2-cd]indazole-2-ethanamine A mixture of 1.47 g (0.004 mole) of 5-amino-N,N-diethyl-2H-[benzoselenino[4,3,2-cd]indazol-2-ethanamine, 3.0 g (0.02 mole) 2-diethylaminethylbromide, hydrobromide, and 25 ml absolute ethanol is heated under reflux for 24 hours. Additional 2-diethylaminoethylbromide, hydrobromide (3.0 g) is added portionwise during the next 64 hours. After 88 hours, the reaction is cooled to 0° C. The solid is collected and washed with cold ethanol to give 1.20 g of the dried crude product. Recrystallization from ethanol/2-propanol (3/1) gives 1.1 grams of dried product as a salt with 1.98 equivalents of hydrogen bromide and solvated with 0.06 equivalent of water; mp 243°-244° C. (dec.).

EXAMPLE 104

N-[2-[2-(diethylamino)ethyl]-2H-[1]-benzoselenino-[4,3,2-cd]indazol-5-yl]-1,3-propanediamine A mixture of 3.08 g (0.008 mole) of 5-amino-N,N-diethyl-2H[1]benzoselenino[4,3,2-cd]indazole-2-ethanamine, 5.26 g (0.02 mole) of 3-bromopropylamine, hydrobromide, and 50 ml of absolute ethanol is heated under reflux for 24 hours. Additional 3-bromopropylamine, hydrobromide, (4.5 g) is added portionwise during the next 40 hours. After 64 hours, the reaction is cooled to 0° C. The solid is collected and washed with cold ethanol to give 1.92 g of the dried crude product. Recrystallization twice from ethanol/methanol (1/1) gives 0.375 g of the dried product as a salt with 2.91 equivalents of hydrogen bromide and solvated with 1.9 equivalents of water that is 87% pure according to high performance liquid chromatography; mp 255°-256° C. (dec.).

EXAMPLE 105

5-Nitro-2-[2-(1-pyrrolidinyl)ethyl]-2H-[1]benzoselenino[4,3,2-cd]indazole,hydrochloride An ice cold solution of 4.47 g (0.013 mole) of 1-chloro-4-nitro-9H-selenoxanthen-9-one in 50 ml of N,N-dimethyl-formamide with 7 ml of diisopropylethylamine is treated dropwise with 3.4 g of 1-(2-hyrazinoethyl)pyrrolidine. The cooling bath is removed after 10 minutes and the reaction is stirred at 25° C. for one hour. Concentration of the reaction in vacuo leaves an orange solid that is triturated with boiling 2-propanol to give 4.78 g of the product as a salt with 1.18 equivalents of water and 0.81 equivalents of hydrogen chloride, mp 258°-262° C.

EXAMPLE 106

5-Amino-2-[2-(1-pyrrolidinyl)ethyl]-2H-[1]benzoselenino[4,3,2-cd]indazole,hydrochloride A suspension of 3.09 g (0.006 mole) of 5-nitro-2-[2-(1-pyrrolidinyl)ethyl]-2H-[1]benzoselenino[4,3,2-cd]indazole,hydrochloride and 0.250 g of 20% palladium on carbon in 100 ml of methanol and 20 ml of glacial acetic acid is hydrogenated at atmospheric pressure for 13 hours. The mixture is filtered through Celite® and concentrated in vacuo to an orange solid. The solid is evaporated several times from n-heptane to remove residual acetic acid. The resulting solid is dissolved in warm 2-propanol and acidified with a solution of hydrogen chloride in 2-propanol to give a fluffy off white precipitate. The solid is collected and dried in vacuo to give 2.99 g of the product as a salt with 1.94 equivalents of hydrogen chloride and solvated with 0.52 equivalents of water; mp>300° C.

EXAMPLE 107

5-[(2-Aminoethyl)amino]-2-[2-(1-[pyrrolidinyl)ethyl]-2H-[1]benzoselenino[4,3,2-cd]indazol,hydrochloride A suspension of 2.10 g (0.003 mole) of 2-[2-[[[2-(1-pyrrolidinyl)ethyl]-2H-[1]benzoselenino[4,3,2-cd]indazol-5-yl]amino]ethyl]-1-H-isoindole-1,3(2H)-dione in 80 ml of methanol with 4.5 ml of methylhydrazine is heated under reflux in an argon atmosphere for 17 hours. The solution is concentrated in vacuo several times from 2-propanol and the residue is dissolved in a 1 to 1 mixture of methanol and 2-propanol. To this solution is added 5 ml of a solution of hydrogen chloride in 2-propanol (1.22 g of hydrogen chloride in 10 ml of 2-propanol). The resulting solid is triturated with boiling 2-propanol to give 1.34 g of the product as a salt with 2.74 equivalents of hydrogen chloride and solvated with 0.61 equivalents of water and 0.14 equivalents of 2-propanol; mp 265°–272° (decomposition).

2-[2-[[[2-(1-Pyrrolidinyl)ethyl]-2H-[1]benzoselenino[4,3,2-cd]indazol-5-yl]amino]ethyl]-1-H-isoindole-1,3(2H)-dione is prepared as follows:

To the resulting solid is added 2.39 g (0.009 mole) of N-(2-bromoethyl)phthalimide and the mixture is heated under an argon atmosphere at 110° C. for 24 hours. An additional 1.2 g portion of N-(2-bromoethyl)phthalimide is added and heating is continued for another six hours. The reaction is cooled to room temperature and dichloromethane is added with 2.5 ml of diisopropylethylamine. The mass is heated under reflux for ten hours under argon. After cooling to 25° C., the reaction is diluted with ethyl acetate and washed twice with a solution of saturated aqueous sodium bicarbonate. The organic portion is separated, dried over sodium sulfate, filtered, and concentrated to a dark oil. Chromatography on silica gel with a solution of 5% methanol in dichloromethane gives 2.10 g of product as a foamy solid sufficiently pure for further reaction.

EXAMPLE 108

2-[2-(Diethylamino)ethyl]-5-nitro-2H-[1]benzoselenino-[4,3,2-cd]indazol-9-ol, hydrochloride 1-Chloro-7-methoxy-4-nitro-9H-selenoxanthen-9-one (3.49 g, 0.010 mole) is suspended in 50 ml of dry 1,2-dichloroethane. To this mixture is added 3.77 g (0.028 mole) of powdered aluminum chloride and the suspension is heated under reflux in an argon atmosphere for 2.5 hours. The reaction is cooled to room temperature and evaporated in vacuo to a dark residue. The residue is stirred with 100 ml of concentrated hydrochloric acid under argon for 15 hours. The solids are collected, rinsed with cold water, triturated with warm 2-propanol, and dried in vacuo at 70° C. to give 4.74 g of crude product. An ice cold solution of 0.536 g (0.015 mole) of crude phenol in 5 ml of N,N-dimethylformamide with 0.525 ml of diisopropylethylamine is treated dropwise with 0.350 ml of 2-(diethylaminoethyl)hydrazine. The cooling bath is removed after ten minutes and the mixture is stirred at 25° C. for two hours. Concentration of the reaction in vacuo leaves an orange solid that is triturated with boiling 2-propanol to give 0.527 g of the dried product as a salt with 0.45 equivalents of hydrogen chloride and solvated with 0.74 equivalents of water; mp 247°–249° C. (decomposition).

EXAMPLE 109

2-[2-(Diethylamino)ethyl]-5-nitro-2H-[1]benzoselenino-[4,3,2-cd]indazol-8-ol, hydrochloride To an ice-cold solution of 1.59 g (0.004 mole) of 1-chloro-6-hydroxy-4-nitro-9H-selenoxanthen-9-one in 12 ml of N,N-dimethylformamide with 0.85 ml of diisopropylethyl amine is added 0.85 ml of 2-(diethylaminoethyl)hydrazine. The cooling bath is removed and the mixture is stirred at 25° C. for 2.5 hours. Concentration of the reaction in vacuo leaves an orange solid. Trituration of the solid with boiling 2-propanol gives an orange powder which is dried in vacuo at 80° C. to afford 1.66 g of the dry product as a salt with 1.0 equivalents of hydrogen chloride; mp 255°–257° C. (dec.).

EXAMPLE 110

5-[(2-Aminoethyl)amino]-2-[2-(diethylamino)ethyl]-2H-[1]benzoselenino[4,3,2-cd]indazol-9-ol, trihydrochloride A suspension of 1.95 g (0.003 mole) of 2-[2-[[[2-(diethylamino)ethyl]-9-hydroxy-2H-[1]benzoselenino[4,3,2-cd]indazol-5-yl]amino]ethyl]-1-H-isoindole-1,3(2H)-dione in 80 ml of methanol with 4.5 ml of methylhydrazine is heated under reflux in an argon atmosphere for 18 hours. The solution is concentrated in vacuo several times from 2-propanol and the residue is dissolved in a 1:1 (v/v) mixture of methanol and 2-propanol. To this solution is added 4 ml of a solution of hydrogen chloride in 2-propanol (1.22 g of hydrogen chloride in 10 ml of 2-propanol). The pale yellow solid is collected and recrystallized from methanol and 2-propanol to give 1.724 g of the dry product as a salt with three equivalents of hydrogen chloride and solvated with 0.30 equivalents of water; mp>260° C.

2-[2-[[[2-(Diethylamino)ethyl]-9-hydroxy-2H-[1]benzoselenino[4,3,2-cd]indazol-5-yl]amino]ethyl]-1-H-isoindole-1,3(2H)dione is prepared as follows:

A suspension of 4.28 g (0.009 mole) of 2-[2-(diethylamino)ethyl]-5-nitro-2H-[1]benzoselenino[4,3,2-cd]indazol-9-ol, hydrochloride and 0.650 g of 20% palladium on carbon in 100 ml N,N-dimethylformamide is hydrogenated at atmospheric pressure for 13 hours. An additional 0.25 g of catalyst is added and the hydrogenation continues for another 24 hours. The mixture is filtered through a Celite pad and the filtrate is concentrated in vacuo to 4.74 g of a dark orange-brown oil. To this oil is added 2.67 g (0.011 mole) of N-(2-bromoethyl)phthalimide and the mixture is heated under argon in a 110° C. oil bath for 20 hours. To the resulting solid is added 200 ml of 1,2-dichloroethane and 3.3 ml of diisopropylethylamine. The mixture is heated under reflux in an argon atmosphere for two hours, diluted further with dichloromethane, and washed once with a saturated solution of aqueous sodium bicarbonate. The organic layer is separated, dried over sodium sulfate, filtered, and concentrated to a crude solid. The solid is dissolved in dichloromethane and filtered through a small column of Florisil with a 1:9 (v/v) solution of methanol and 1,2-dichloroethane. The effluent is concentrated and the resulting solid is triturated with hot 2-propanol to give 1.98 g of the dried product; mp 203°–205° C.

Starting from the appropriately substituted 7,8,9 or 10-hydroxy or methoxy 1-chloro-4-nitro-9H-selenoxanthen-9-ones, the following 2-(aminoalkyl)-5-(aminoalkylamino)-2H-[1]benzoselenino[4,3,2-cd]-indazoles are prepared by methods similar to those detailed in Example 100:

5-[(2-Aminoethyl)amino]-2-[2-(Diethylamino)ethyl]-2H-[1]benzoselenino[4,3,2-cd]indazol-8-ol;
2-[2-(Diethylamino)ethyl]-5-[[2-[(2-hydroxyethyl)amino]ethyl]amino]-2H-[1]benzoselenino[4,3,2cd]-indazol-8-ol;
2-[2-[(2-hydroxyethyl)amino]ethyl]-5-[[2-[(2-hydroxyethyl)amino]ethyl]amino]-2H-[1]benzoselenino[4,3,2-cd]-indazol-8-ol;
5-[(2-aminoethyl)amino]-2-[2-(diethylamino)ethyl]-2H-[1]benzoselenino[4,3,2-cd]indazol-9-ol;
2-[2-(diethylamino)ethyl]-5-[[2-[(2-hydroxyethyl)amino]-ethyl]amino]-2H-[1]benzoselenino[4,3,2-cd]-indazol-9-ol;

2-[2-](2-hydroxyethyl)amino]ethyl]-5-[[2-[(2-hydroxyethyl)amino]ethyl]amino]-2H-[1]benzoselenino[4,3,2-cd]indazol-9-ol;

5-[(3-aminopropyl)amino]-2-[2-(diethylamino)ethyl]-2H-[1]benzoselenino[4,3,2-cd]indazol-9-ol;

5-[(aminoethyl)amino]-2-[2-(diethylamino)ethyl]-2H-[1]benzoselenino[4,3,2-cd]indazol-10-ol;

2-[2-(diethylamino)ethyl]-5-[[2-[(2-hydroxyethyl)amino]ethyl]amino]-2H-[1]benzoselenino[4,3,2-cd]-indazol-10-ol;

2-[2-[(2-hydroxyethyl)amino]ethyl]-5-[[2-(2-hydroxyethyl)amino]ethyl]amino]-2H-[1]benzoselenino-[4,3,2-cd]indazol-10-ol;

5-[(2-aminoethyl)amino]-2-[2-(diethylamino)ethyl]-2H-[1]benzoselenino[4,3,2-cd]indazole-7,8-diol;

2-[2-(diethylamino)ethyl]-5-[[2-[(2-hydroxyethyl)amino]ethyl]amino]-2H-[1]benzoselenino[4,3,2-cd]-indazole-7,8-diol;

2-[2-[(2-hydroxyethyl)amino]ethyl]-5-[[2-[(2-hydroxyethyl)amino]ethyl]amino]-2H-[1]benzoselenino[4,3,2-cd]indazole-7,8-diol;

5-[(2-aminoethyl)amino]-2-[2-(diethylamino)ethyl]-2H-[1]benzoselenino[4,3,2-cd]indazole-8,10-diol;

2-[2-(diethylamino)ethyl]-5-[[2-[(2-hydroxyethyl)amino]ethyl]amino]-2H-[1]benzoselenino[4,3,2-cd]-indazole-8,10-diol; and 2-[2-[(2-hydroxyethyl)amino]ethyl]-5-[[2-[(2-hydroxyethyl)amino]ethyl]amino]-2H-[1]benzoselenino-[4,3,2-cd]indazole-8,10-diol.

We claim:

1. A benzo(chalcogeno)[4,3,2-cd]indazole compound having the structural formula

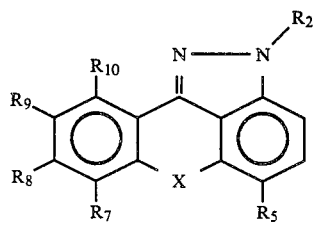

or a pharmaceutically acceptable salt thereof, wherein X is oxygen, sulfur, or selenium; the substituents $R_7$, $R_8$, $R_9$, and $R_{10}$ are independently hydrogen, hydroxy, alkoxy of from 1 to 4 carbon atoms wherein $R_2$ is —ANR'R" wherein A is a straight or branched alkylene chain of from 2 to 5 carbon atoms optionally substituted with hydroxyl; wherein R' and R" are hydrogen or are straight or branched alkyl of from 1 to 4 carbon atoms optionally substituted with hydroxyl, or where R' and R" taken together also represent

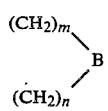

wherein m and n are each 2 and B is a direct bond, or oxygen, sulfur, or NR''' wherein R''' is hydrogen or straight or branched alkyl of from 1 to 4 carbon atoms optionally substituted with hydroxyl; and wherein $R_5$ is nitro, $NH_2$, $NHR_2$, or NHR'''' where R'''' is

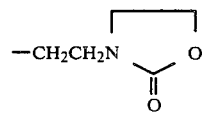

or is

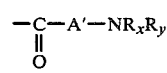

wherein A' is a straight or branched alkylene chain of from 1 to 5 carbon atoms, and $R_x$ and $R_y$ are independently hydrogen or straight or branched alkyl of from 1 to 4 carbon atoms optionally substituted with hydroxyl.

2. A compound as defined by claim 1 wherein X is oxygen.

3. A compound as defined in claim 1 wherein X is sulfur.

4. A compound as defined by claim 1 wherein X is selenium.

5. A compound as defined by claim 2 having the name N-[2-[2-(diethylamino)ethyl]-2H-[1]benzopyrano[4,3,2-cd]-indazol-5-yl]ethanediamine or a pharmaceutically acceptable salt thereof.

6. A compound as defined by claim 2 having the name N-[2-[2-(diethylamino)ethyl]-9-hydroxy-2H-[1]benzopyrano[4,3,2-cd]indazol-5-yl]ethanediamine or a pharmaceutically acceptable salt thereof.

7. A compound as defined by claim 2 having the name 2-[3-(dimethylamino)propyl]-5-nitro-2H-[1]benzopyrano[4,3,2-cd]indazol-9-ol or a pharmaceutically acceptable salt thereof.

8. A compound as defined in claim 2 having the name 5-amino-2-[2-[(2-hydroxyethyl)amino]ethyl]-2H-[1]benzopyrano[4,3,2-cd]indazol-9-ol or a pharmaceutically acceptable salt thereof.

9. A compound as defined by claim 2 having the name N-[2-[2-(diethylamino)ethyl]-9-hydroxy-2H-[1]benzopyrano[4,3,2-cd]indazol-5-yl]-2-[(2-hydroxyethyl)aminoacetamide or a pharmaceutically acceptable salt thereof.

10. A compound as defined by claim 2 having the name 2-[2-[(2-hydroxyethyl)amino]ethyl]-5-nitro-2H-[1]benzopyrano[4,3,2-cd]indazol-9-ol or a pharmaceutically acceptable salt thereof.

11. A compound as defined by claim 2 having the name 2-[2-(diethylamino)ethyl]-5-[[2-[(2-hydroxyethyl)amino]ethyl]amino-2H-[1]benzopyrano[4,3,2-cd]indazol-9-ol or a pharmaceutically acceptable salt thereof.

12. A compound as defined by claim 2 having the name 2-[2-[(2-hydroxyethyl)amino]ethyl]-5-[[2-[(2-hydroxyethyl)amino]ethyl]amino]-2H-[1]benzopyrano[4,3,2-cd]-indazol-9-ol or a pharmaceutically acceptable salt thereof.

13. A compound as defined by claim 2 having the name 5-[(2-aminoethyl)amino]-2-[2-(diethylamino)ethyl]-2H-[1]benzopyrano[4,3,2-cd]indazol-8-ol or a pharmaceutically acceptable salt thereof.

14. A compound as defined by claim 2 selected from the group consisting of:
N,N-diethyl-9-hydroxy-5-nitro-2H-[1]benzopyrano-[4,3,2-cd]indazole-2-ethanamine;
5-amino-2-[2-(diethylamino)ethyl]-2H-[1]benzopyrano-[4,3,2-cd]indazol-9-ol;

2-[2-[(2-hydroxyethyl)amino]ethyl]-9-hydroxy-2H-[1]benzopyrano[4,3,2-cd]indazol-5-yl]-2-(2-hydroxyethyl)-amino]acetamide;
5-nitro-2-[2-(1-pyrrolidinyl)ethyl]-2H-[1]benzopyrano[4,3,2-cd]indazol-9-ol; or a pharmaceutically acceptable salt thereof.

15. A compound as defined by claim 2 selected from the group consisting of:
N,N-diethyl-9-methoxy-5-nitro-2H-[1]benzopyrano[4,3,2-cd]indazole-2-ethanamine;
9-methoxy-N,N-dimethyl-5-nitro-2H-[1]benzopyrano[4,3,2-cd]indazole-2-propanamine;
9-methoxy-2-[2-(1-pyrrolidinyl)ethyl]-2H-[1]benzopyrano[4,3,2-cd]indazol-5-amine;
or a pharmaceutically acceptable salt thereof.

16. A compound as defined by claim 3 having the name 2-[2-(diethylamino)ethyl]-5-[[2-[(2-hydroxyethyl)-amino]ethyl]amino]-2H-[1]benzothiopyrano[4,3,2-cd]indazol-9-ol or a pharmaceutically acceptable salt thereof.

17. A compound as defined by claim 3 having the name 5-[(2-aminoethyl)amino]-2-[2-(diethylamino)ethyl]-2H-[1]benzothiopyrano[4,3,2-cd]indazol-8-ol or a pharmaceutically acceptable salt thereof.

18. A compound as defined by claim 3 having the name 5-[(2-aminoethyl)amino]-2-[2-(diethylamino)ethyl]-2H-[1]benzothiopyrano[4,3,2-cd]indazol-9-ol or a pharmaceutically acceptable salt thereof.

19. A compound as defined by claim 3 selected from the group consisting of:
2-[[2-(5-nitro-2H-[1]benzothiopyrano[4,3,2-cd]-indazol-2-yl)ethyl]amino]ethanol;
2-[[2-(5-amino-2H-[1]benzothiopyrano[4,3,2-cd]indazol-2-yl)ethyl]amino]ethanol;
2-[[2-[5-[[2-[(2-hydroxyethyl)amino]ethyl]amino]-2H-[1]benzothiopyrano[4,3,2-cd]indazol-2-yl]ethyl]amino]ethanol;
2-[[2-[5-[[2-(diethylaminoethyl]amino]-2H-[1]benzothiopyrano[4,3,2-cd]indazol-2-yl]ethyl]amino]ethanol;
or a pharmaceutically acceptable salt thereof.

20. A compound as defined by claim 3 selected from the group consisting of:
2-[[2-[[2-(2-aminoethyl)-2H-[1]benzothiopyrano-[4,3,2-cd]indazol-5-yl]amino]ethyl]amino]ethanol;
2-[[2-[[2-[2-(diethylamino)ethyl]-2H-[1]benzothiopyrano[4,3,2-cd]indazol-5-yl]amino]ethyl]amino]ethanol;
or a pharmaceutically acceptable salt thereof.

21. A compound as defined by claim 3 selected from the group consisting of:
5-nitro-2H-[1]benzothiopyrano[4,3,2-cd]indazole-2-ethanamine;
N,N-diethyl-5-nitro-2H-[1]benzothiopyrano[4,3,2-cd]-indazole-2-ethanamine;
N,N-dimethyl-5-nitro-2H-[1]benzothiopyrano[4,3,2-cd]-indazole-2-propanamine;
5-amino-N,N-diethyl-2H-[1]benzothiopyrano[4,3,2-cd]-indazole-2-ethanamine;
5-amino-N,N-dimethyl-2H-[1]benzothiopyrano[4,3,2-cd]-indazole-2-propanamine;
N-[2-2-(diethylamino)ethyl]-2H-[1]benzothiopyrano[4,3,2-cd]indazol-5-yl]-1,2-ethanediamine;
N-[2-[3-(dimethylamino)propyl]-2H-[1]benzothiopyrano-[4,3,2-cd]indazol-5-yl]-1,2-ethanediamine;
N-[2-[2-(diethylamino)ethyl]-2H-[1]benzothiopyrano-[4,3,2-cd]indazol-5-yl]-1,3-propanediamine;
or a pharmaceutically acceptable salt thereof.

22. A compound as defined by claim 3 selected from the group consisting of:
5-amino-2-[2-(diethylamino)ethyl]-2H-[1]benzothiopyrano[4,3,2-cd]indazol-7-ol;
5-[2-(aminoethyl)amino]-2-[2-(diethylamino)ethyl]-2H-[1]benzothiopyrano[4,3,2-cd]indazol-7-ol;
or a pharmaceutically acceptable salt thereof.

23. A compound as defined by claim 3 selected from the group consisting of:
N,N-diethyl-7-methoxy-5-nitro-2H-[1]benzothiopyrano-[4,3,2-cd]indazol-2-ethanamine;
5-amino-N,N-diethyl-7-methoxy-2H-[1]benzothiopyrano[4,3,2-cd]indazol-2-ethanamine;
or a pharmaceutically acceptable salt thereof.

24. A compound as defined by claim 3 selected from the group consisting of:
5-amino-2-[2-(diethylamino)ethyl]-2H-[1]benzothiopyrano[4,3,2-cd]indazol-8-ol;
5-[2-(aminoethyl)amino]-2-[2-(diethylamino)ethyl]-2H-[1]benzothiopyrano[4,3,2-cd]indazol-8-ol;
or a pharmaceutically acceptable salt thereof.

25. A compound as defined by claim 3 selected from the group consisting of:
N,N-diethyl-8-methoxy-5-nitro-2H-[1]benzothiopyrano-[4,3,2-cd]indazole-2-ethanamine;
5-amino-N,N-diethyl-8-methoxy-2H-[1]benzothiopyrano[4,3,2-cd]indazole-2-ethanamine;
N-[2-[2-(diethylamino)ethyl]-8-methoxy-2H-[1]benzothiopyrano[4,3,2-cd]indazol-5-yl]-1,2-ethanediamine;
or a pharmaceutically acceptable salt thereof.

26. A compound as defined by claim 3 selected from the group consisting of:
2-[2-(diethylamino)ethyl]-5-nitro-2H-[1]benzothiopyrano[4,3,2-cd]indazol-9-ol;
5-amino-2-[2-(diethylamino)ethyl]-2H-[1]benzothiopyrano[4,3,2-cd]indazol-9-ol;
2-amino-N-[2-[2-(diethylamino)ethyl]-2H-[1]benzothiopyrano[4,3,2-cd]indazol-9-ol;
or a pharmaceutically acceptable salt thereof.

27. A compound as defined by claim 3 having the name N,N-diethyl-9-methoxy-5-nitro-2H-[1]benzothiopyrano-[4,3,2-cd]indazole-2-ethanamine; or a pharmaceutically acceptable salt thereof.

28. A compound as defined by claim 3 selected from the group consisting of:
5-amino-2-[2-(diethylamino)ethyl]-2H-[1]benzothiopyrano[4,3,2-cd]indazol-10-ol;
5-[2-(aminoethyl)amino]-2-[2-(diethylamino)ethyl]-2H-[1]benzothiopyrano[4,3,2-cd]indazol-10-ol;
or a pharmaceutically acceptable salt thereof.

29. A compound as defined by claim 3 selected from the group consisting of:
N,N-diethyl-10-methoxy-5-nitro-2H-[1]benzothiopyrano-[4,3,2-cd]indazole-2-ethanamine;
5-amino-N,N-diethyl-10-methoxy-2H-[1]benzothiopyrano[4,3,2-cd]indazole-2-ethanamine;
or a pharmaceutically acceptable salt thereof.

30. A compound as defined by claim 4 having the name N-[2-[2-(diethylamino)ethyl]-2H-[1]benzoselenino-[4,3,2-cd]indazol-5-yl]-1,2-ethanediamine or a pharmaceutically acceptable salt thereof.

31. A compound as defined by claim 4 having the name 2-[[2-[5-[[2-[(2-hydroxyethyl)amino]ethyl]amino]-2H-[1]benzoselenino[4,3,2-cd]indazole-2-yl]ethyl]amino]-ethanol or a pharmaceutically acceptable salt thereof.

32. A compound as defined by claim 4 having the name 5-[(2-aminoethyl)amino]-2-[2-(diethylamino)e- thyl]-2H-[1]benzoselenino[4,3,2-cd]indazol-8-ol or a pharmaceutically acceptable salt thereof.

33. A compound as defined by claim 4 having the name 5-[(2-Aminoethyl)amino]-2-[2-(diethylamino)ethyl]-2H-[1]benzoselenino[4,3,2-cd]indazol-9-ol or a pharmaceutically acceptable salt thereof.

34. A compound as defined by claim 4 having the name 2-[2-(diethylamino)ethyl]-5-[[2-[(2-hydroxyethyl)amino]ethyl]amino]-2H-[1]benzoselenino[4,3,2-cd]indazol-8-ol or a pharmaceutically acceptable salt thereof.

35. A compound as defined by claim 4 having the name 2-[2-(diethylamino)ethyl]-5-[[2-[(2-hydroxyethyl)amino]ethyl]amino]-2H-[1]benzoselenino[4,3,2-cd]indazol-9-ol or a pharmaceutically acceptable salt thereof.

36. A compound as defined by claim 4 having the name 5-[(2-aminoethyl)amino]-2-[2-(diethylamino)ethyl]-2H-[1]benzoselenino[4,3,2-cd]indazol-7,8-diol or a pharmaceutically acceptable salt thereof.

37. A compound as defined by claim 4 having the name 5-[(2-aminoethyl)amino]-2-[2-diethylamino)ethyl]-2H-[1]benzoselenino[4,3,2-cd]indazole-8,10-diol or a pharmaceutically acceptable salt thereof.

38. A compound as defined in claim 4 having the name 5-[(2-aminoethyl)amino]-2-[2-(1-pyrrolidinyl)ethyl]-2H-[1]benzoselenino[4,3,2-cd]indazole or a pharmaceutically acceptable salt thereof.

39. A compound as defined by claim 4 selected from the group consisting of:
N,N-diethyl-5-nitro-2H-[1]benzoselenino[4,3,2-cd]-indazole-2-ethanamine;
5-amino-N,N-diethyl-2H-[1]benzoselenino[4,3,2-cd]indazole-2-ethanamine;
N,N-diethyl-5-[[2-(diethylamino)ethyl]amino]-2H-[1]benzoselenino[4,3,2-cd]indazole-2-ethanamine;
N-[2-[2-(diethylamino)ethyl]-9-methoxy-2H-[1]benzoselenino[4,3,2-cd]indazol-5-yl]ethanediamine;
N-[2-[2-(diethylamino)ethyl]-2H-[1]benzoselenino-[4,3,2-cd]indazol-5-yl]-1,3-propanediamine;
2-[[2-[[2-[2-(diethylamino)ethyl]2H-[1]benzoselenino-[4,3,2-cd]indazol-5-yl]amino]ethyl]amino]ethanol;
or a pharmaceutically acceptable salt thereof.

40. A compound as defined by claim 4 selected from the group consisting of:
2-[2-(diethylamino)ethyl]-5-nitro-2H-[1]benzoselenino[4,3,2-cd]indazole-8-ol;
2-[2-(diethylamino)ethyl]-5-[[2-[2-hydroxyethyl)amino]ethyl]-2H-[1]benzoselenino[4,3,2-cd]indazol-8-ol;
2-[2-[(2-Hydroxyethyl)amino]ethyl]-5-[[2-[(2-hydroxyethyl)amino]ethyl]amino]-2H-[1]benzoselenino[4,3,2-cd]-indazol-8-ol; or a pharmaceutically acceptable salt thereof.

41. A compound as defined by claim 4 selected from the group consisting of:
2-[2-(diethylamino)ethyl]-5-nitro-2H-[1]benzoselenino[4,3,2-cd]indazole-9-ol;
2-[2-[(2-hydroxyethyl)amino]ethyl]-5-[[2-[(2-hydroxyethyl)amino]ethyl]amino]-2H-[1]benzoselenino[4,3,2-cd]-indazol-9-ol;
5-[(3-Aminopropyl)amino]-2-(diethylamino)ethyl]-2H-[1]benzoselenino[4,3,2-cd]indazol-9-ol;
or a pharmaceutically acceptable salt thereof.

42. A compound as defined by claim 4 selected from the group consisting of:
5-[(aminoethyl)amino]-2-[2-(diethylamino)ethyl]-2H-[1]benzoselenino[4,3,2-cd]indazol-10-ol;
2-[2-(diethyamino)ethyl]-5-[[2-[(2-hydroxyethyl)-amino]ethyl]amino]-2H-[1]benzoselenino[4,3,2-cd]indazol-10-ol;
2-[2-[(2-Hydroxyethyl)amino]ethyl-5-[[2-(2-hydroxyethyl)amino]ethyl]amino]-2H-[1]benzoselenino[4,3,2-cd]indazol-10-ol;
or a pharmaceutically acceptable salt thereof.

43. A compound as defined by claim 4 selected from the group consisting of:
2-[2-(diethylamino)ethyl]-5-[[2-[(2-hydroxyethyl)-amino]ethyl]amino]-2H-[1]benzoselenino[4,3,2-cd]indazol-7,8-diol;
2-[2-[(2-hydroxyethyl)amino]ethyl]-5-[[2-[(2-hydroxyethyl)amino]ethyl]amino]-2H-[1]benzoselenino-[4,3,2-cd]indazol-7,8-diol;
or a pharmaceutically acceptable salt thereof.

44. A compound as defined by claim 4 having the name 2-[2-(diethylamino)ethyl]-5-[[2-[(2-hydroxyethyl)-amino]ethyl]amino]-2H-[1]benzoselenino[4,3,2-cd]indazol-8,10-diol or a pharmaceutically acceptable salt thereof.

45. A pharmaceutical composition useful for the treatment of bacterial infections in a mammal comprising an antibacterially effective amount of a compound as defined by claim 1 in combination with a pharmaceutically acceptable carrier.

46. A method of treating bacterial infections in a mammal comprising administering to a mammal in need of such treatment an antibacterially effective amount of a compound as defined by claim 1 in combination with a pharmaceutically acceptable carrier.

* * * * *